(12) United States Patent
Howell et al.

(10) Patent No.: US 10,806,900 B2
(45) Date of Patent: Oct. 20, 2020

(54) INSERTION DEVICE WITH INTERFACE PAD AND METHODS OF MAKING

(71) Applicant: C. R. Bard, Inc., Murray Hill, NJ (US)

(72) Inventors: Glade H. Howell, Draper, UT (US); Anthony S. Elangovan, Salt Lake City, UT (US); Lindsey E. Corum, Cottonwood Heights, UT (US)

(73) Assignee: C. R. Bard. Inc., Franklin Lakes, NJ (US)

( * ) Notice: Subject to any disclaimer, the term of this patent is extended or adjusted under 35 U.S.C. 154(b) by 0 days.

(21) Appl. No.: 16/733,926

(22) Filed: Jan. 3, 2020

(65) Prior Publication Data

US 2020/0139085 A1    May 7, 2020

Related U.S. Application Data

(60) Division of application No. 14/789,341, filed on Jul. 1, 2015, now Pat. No. 10,525,234, which is a
(Continued)

(51) Int. Cl.
*A61M 25/02* (2006.01)
*A61M 5/158* (2006.01)
(Continued)

(52) U.S. Cl.
CPC ............ *A61M 25/02* (2013.01); *A61M 5/158* (2013.01); *B32B 37/12* (2013.01); *B32B 37/142* (2013.01);
(Continued)

(58) Field of Classification Search
CPC .... A61M 25/02; A61M 5/3275; A61M 5/158; A61M 2025/0273; A61M 2025/066;
(Continued)

(56) References Cited

U.S. PATENT DOCUMENTS 2,847,995 A    8/1958 Adams
2,876,770 A    3/1959 White
(Continued)

FOREIGN PATENT DOCUMENTS

CN    1175906 A    3/1998
CN    1451028 A    10/2003
(Continued)

OTHER PUBLICATIONS

CN 201580039156.3 filed Jan. 18, 2017 Office Action dated Apr. 24, 2019.
(Continued)

*Primary Examiner* — Matthew F Desanto
(74) *Attorney, Agent, or Firm* — Rutan & Tucker LLP

(57) ABSTRACT

An insertion assembly and method of manufacturing an insertion assembly. The method includes forming a catheter assembly including a catheter hub and a catheter, inserting a needle into the catheter assembly such that a distal tip of the needle extends distal of a distal end of the catheter, and permanently adhering an interface pad to the catheter hub. The interface pad can include a foam material including a haemostatic agent. The haemostatic agent can include microdispersed oxidized cellulose. The foam material can further include an antimicrobial agent such as chlorhexidine gluconate.

17 Claims, 40 Drawing Sheets

Related U.S. Application Data continuation-in-part of application No. 14/070,246, filed on Nov. 1, 2013, now abandoned, which is a continuation-in-part of application No. 13/229,573, filed on Sep. 9, 2011, now Pat. No. 9,248,234.

(60) Provisional application No. 62/019,807, filed on Jul. 1, 2014, provisional application No. 61/721,412, filed on Nov. 1, 2012, provisional application No. 61/381,762, filed on Sep. 10, 2010.

(51) Int. Cl.
*B32B 37/12* (2006.01)
*B32B 37/14* (2006.01)
*B32B 37/18* (2006.01)
*A61M 5/32* (2006.01)
*A61M 5/00* (2006.01)
*A61M 39/02* (2006.01)

(52) U.S. Cl.
CPC .......... *B32B 37/182* (2013.01); *A61M 5/002* (2013.01); *A61M 5/3273* (2013.01); *A61M 5/3275* (2013.01); *A61M 39/0208* (2013.01); *A61M 2005/1581* (2013.01); *A61M 2005/325* (2013.01); *A61M 2005/3256* (2013.01); *A61M 2025/0273* (2013.01); *A61M 2209/045* (2013.01); *B32B 2535/00* (2013.01)

(58) Field of Classification Search
CPC ............... A61M 5/002; A61M 5/3273; A61M 39/0208; A61M 2005/1581; A61M 2005/325; A61M 2005/3256; A61M 2209/045; B32B 37/12; B32B 37/142; B32B 37/182; B32B 2535/00
See application file for complete search history.

(56) References Cited

U.S. PATENT DOCUMENTS

| | | |
|---|---|---|
| 2,925,083 A | 2/1960 | Craig |
| 3,134,380 A | 5/1964 | Armao |
| 3,306,290 A | 2/1967 | Weltman |
| 4,160,450 A | 7/1979 | Doherty |
| 4,235,234 A | 11/1980 | Whitney et al. |
| 4,352,254 A | 10/1982 | Peter et al. |
| 4,352,354 A | 10/1982 | Ujihara |
| 4,380,234 A | 4/1983 | Kamen |
| 4,435,175 A | 3/1984 | Friden |
| 4,564,054 A | 1/1986 | Gustavsson |
| 4,592,744 A | 6/1986 | Jagger et al. |
| 4,611,382 A | 9/1986 | Clark |
| 4,615,468 A | 10/1986 | Gay |
| 4,627,842 A | 12/1986 | Katz |
| 4,627,843 A | 12/1986 | Raines |
| 4,631,058 A | 12/1986 | Raines |
| 4,632,671 A | 12/1986 | Dalton |
| 4,645,494 A | 2/1987 | Lee et al. |
| 4,645,495 A | 2/1987 | Vaillancourt |
| 4,655,765 A | 4/1987 | Swift |
| 4,676,782 A | 6/1987 | Yamamoto et al. |
| 4,676,783 A | 6/1987 | Jagger et al. |
| 4,676,788 A | 6/1987 | Vincent |
| 4,695,274 A | 9/1987 | Fox |
| 4,710,176 A | 12/1987 | Quick |
| 4,725,267 A | 2/1988 | Vaillancourt |
| 4,755,173 A | 7/1988 | Konopka et al. |
| 4,755,369 A | 7/1988 | Yoshiharu |
| 4,760,847 A | 8/1988 | Vaillancourt |
| 4,775,369 A | 10/1988 | Schwartz |
| 4,795,432 A | 1/1989 | Karczmer |
| 4,813,939 A | 3/1989 | Marcus |
| 4,820,282 A | 4/1989 | Hogan |
| D301,742 S | 6/1989 | Wyzgala et al. |
| 4,846,809 A | 7/1989 | Sims |
| 4,867,172 A | 9/1989 | Haber et al. |
| 4,897,083 A | 1/1990 | Martell |
| 4,935,011 A | 6/1990 | Hogan |
| 4,935,013 A | 6/1990 | Haber et al. |
| 4,941,881 A | 7/1990 | Masters et al. |
| 4,941,882 A | 7/1990 | Ward et al. |
| 4,944,731 A | 7/1990 | Cole |
| 4,950,250 A | 8/1990 | Haber et al. |
| 4,955,890 A * | 9/1990 | Yamamoto ....... A61B 17/32093 604/175 |
| 4,969,876 A | 11/1990 | Patterson |
| 5,002,533 A | 3/1991 | Jullien |
| 5,013,305 A | 5/1991 | Opie et al. |
| 5,053,017 A | 10/1991 | Chamuel |
| 5,061,250 A | 10/1991 | Shields |
| 5,070,884 A | 12/1991 | Columbus et al. |
| 5,085,639 A | 2/1992 | Ryan |
| 5,088,982 A | 2/1992 | Ryan |
| 5,092,852 A | 3/1992 | Poling |
| 5,120,320 A | 6/1992 | Fayngold |
| 5,176,653 A | 1/1993 | Metals |
| 5,176,655 A | 1/1993 | McCormick et al. |
| 5,176,662 A | 1/1993 | Bartholomew et al. |
| 5,192,275 A | 3/1993 | Burns |
| 5,197,954 A | 3/1993 | Cameron |
| 5,236,421 A | 8/1993 | Becher |
| 5,295,972 A | 3/1994 | Mischenko |
| 5,312,366 A | 5/1994 | Vailancourt |
| 5,312,371 A | 5/1994 | Dombrowski et al. |
| 5,322,517 A | 6/1994 | Sircom et al. |
| 5,330,438 A | 7/1994 | Gollobin et al. |
| 5,334,158 A | 8/1994 | McLees |
| 5,336,187 A | 8/1994 | Terry et al. |
| 5,336,199 A | 8/1994 | Castillo et al. |
| 5,342,319 A | 8/1994 | Watson et al. |
| 5,342,320 A | 8/1994 | Cameron |
| 5,350,368 A | 9/1994 | Shields |
| 5,354,281 A | 10/1994 | Chen et al. |
| 5,419,766 A | 5/1995 | Chang et al. |
| 5,431,639 A * | 7/1995 | Shaw .................. A61B 17/0057 604/11 |
| 5,433,703 A | 7/1995 | Utterberg et al. |
| 5,451,522 A | 9/1995 | Queener et al. |
| 5,487,728 A | 1/1996 | Vaillancourt |
| 5,487,733 A | 1/1996 | Caizza et al. |
| 5,490,841 A | 2/1996 | Landis |
| 5,505,711 A | 4/1996 | Arakawa et al. |
| 5,520,654 A | 5/1996 | Wahlberg |
| 5,531,704 A | 7/1996 | Knotek |
| 5,531,713 A | 7/1996 | Mastronardi et al. |
| 5,554,106 A | 9/1996 | Layman-Spillar et al. |
| 5,567,495 A | 10/1996 | Modak et al. |
| 5,569,207 A | 10/1996 | Gisselberg et al. |
| 5,575,773 A | 11/1996 | Song et al. |
| 5,584,813 A | 12/1996 | Livingston et al. |
| 5,584,818 A | 12/1996 | Morrison |
| 5,607,398 A | 3/1997 | Parmigiani |
| 5,620,424 A | 4/1997 | Abramson |
| 5,637,096 A | 6/1997 | Yoon |
| 5,662,913 A | 9/1997 | Capelli |
| 5,674,201 A | 10/1997 | Steinman |
| 5,685,860 A | 11/1997 | Chang et al. |
| 5,686,096 A | 11/1997 | Khan et al. |
| 5,693,022 A | 12/1997 | Haynes |
| 5,695,474 A | 12/1997 | Daugherty |
| 5,706,520 A | 1/1998 | Thornton et al. |
| 5,722,959 A | 3/1998 | Bierman |
| 5,755,694 A | 5/1998 | Camus et al. |
| 5,762,632 A | 6/1998 | Whisson |
| 5,779,679 A | 7/1998 | Shaw |
| 5,817,070 A | 10/1998 | Tamaro |
| 5,833,665 A | 11/1998 | Bootman et al. |
| 5,848,990 A | 12/1998 | Cirelli et al. |
| 5,853,393 A | 12/1998 | Bogert |
| 5,858,004 A | 1/1999 | Shields |
| 5,879,330 A | 3/1999 | Bell |
| 5,885,254 A | 3/1999 | Matyas |
| 5,885,255 A | 3/1999 | Jaeger, Jr. et al. |

(56) References Cited

U.S. PATENT DOCUMENTS

| | | |
|---|---|---|
| 5,951,522 A | 9/1999 | Rosato et al. |
| 5,951,525 A | 9/1999 | Thorne et al. |
| 5,993,426 A | 11/1999 | Hollister |
| 6,042,570 A | 3/2000 | Bell et al. |
| 6,126,637 A | 10/2000 | Kriesel et al. |
| 6,165,156 A | 12/2000 | Cesarczyk et al. |
| 6,210,373 B1 | 4/2001 | Allmon |
| 6,238,375 B1 | 5/2001 | Powell |
| 6,261,264 B1 | 7/2001 | Tamaro |
| 6,451,003 B1 | 9/2002 | Prosl et al. |
| 6,497,669 B1 | 12/2002 | Kensey |
| 6,497,682 B1 | 12/2002 | Quartararo |
| 6,500,155 B2 | 12/2002 | Sasso |
| 6,537,255 B1 | 3/2003 | Raines |
| 6,579,539 B2 | 6/2003 | Lawson et al. |
| 6,613,015 B2 | 9/2003 | Sandstrom et al. |
| 6,620,136 B1 | 9/2003 | Pressly, Sr. et al. |
| 6,623,462 B2 | 9/2003 | Guzzo et al. |
| 6,629,959 B2 | 10/2003 | Kuracina et al. |
| 6,659,984 B2 | 12/2003 | Maclean Crawford et al. |
| 6,663,604 B1 | 12/2003 | Huet |
| 6,676,633 B2 | 1/2004 | Smith et al. |
| 6,689,102 B2 | 2/2004 | Greene |
| 6,699,217 B2 | 3/2004 | Bennett et al. |
| 6,719,727 B2 | 4/2004 | Brimhall et al. |
| 6,749,588 B1 | 6/2004 | Howell et al. |
| 6,755,805 B1 | 6/2004 | Reid |
| 6,783,002 B1 | 8/2004 | Pavlo |
| 6,808,509 B1 | 10/2004 | Davey |
| 6,823,617 B2 | 11/2004 | Schweikert |
| 6,824,530 B2 | 11/2004 | Wagner et al. |
| 6,911,020 B2 | 6/2005 | Raines |
| 6,916,310 B2 | 7/2005 | Sommerich |
| 6,918,894 B2 | 7/2005 | Fleury et al. |
| 6,921,388 B2 | 7/2005 | Swenson |
| 6,926,693 B2 | 8/2005 | Enns |
| 6,932,803 B2 | 8/2005 | Newby |
| 6,969,372 B1 | 11/2005 | Halseth |
| 6,972,002 B2 | 12/2005 | Thorne |
| 6,997,902 B2 | 2/2006 | Thorne et al. |
| 7,083,600 B2 | 8/2006 | Meloul |
| 7,147,623 B2 | 12/2006 | Mathiasen |
| 7,150,725 B2 | 12/2006 | Wilkinson |
| 7,214,208 B2 | 5/2007 | Vaillancourt et al. |
| 7,361,159 B2 | 4/2008 | Fiser et al. |
| 7,407,493 B2 | 8/2008 | Cane' |
| 7,438,703 B2 | 10/2008 | Barrus et al. |
| 7,569,044 B2 | 8/2009 | Triplett et al. |
| 7,601,139 B2 | 10/2009 | Woehr et al. |
| 7,604,616 B2 | 10/2009 | Thoresen et al. |
| 7,637,893 B2 | 12/2009 | Christensen et al. |
| 7,662,159 B2 | 2/2010 | Brandigi |
| 7,717,888 B2 | 5/2010 | Vaillancourt et al. |
| 7,776,016 B1 | 8/2010 | Halseth et al. |
| 7,947,021 B2 | 5/2011 | Bourne et al. |
| 7,967,797 B2 | 6/2011 | Winsor et al. |
| 8,066,678 B2 | 11/2011 | Vaillancourt et al. |
| 8,152,768 B2 | 4/2012 | Halseth et al. |
| 8,263,100 B2 | 9/2012 | Areskoug et al. |
| 8,293,965 B2 | 10/2012 | McMaken et al. |
| 8,486,004 B1 | 7/2013 | Propp |
| 8,569,567 B2 | 10/2013 | Ovington |
| 8,574,197 B2 | 11/2013 | Halseth et al. |
| 8,579,863 B2 | 11/2013 | Scherr |
| 8,597,253 B2 | 12/2013 | Vaillancourt |
| 8,708,969 B2 | 4/2014 | Carlyon |
| 8,728,029 B2 | 5/2014 | Vaillancourt et al. |
| 8,852,154 B2 | 10/2014 | Halseth et al. |
| 9,248,234 B2 | 2/2016 | Barron |
| 9,566,417 B1 | 2/2017 | Propp |
| 9,579,451 B2 | 2/2017 | Stumpp |
| 9,713,673 B2 | 7/2017 | Vaillancourt |
| 10,143,799 B2 | 12/2018 | Barron et al. |
| 10,525,234 B2 | 1/2020 | Howell et al. |
| 2001/0025168 A1 | 9/2001 | Gross et al. |
| 2001/0039401 A1 | 11/2001 | Ferguson et al. |
| 2002/0055711 A1 | 5/2002 | Lavi et al. |
| 2002/0072716 A1 | 6/2002 | Barrus et al. |
| 2002/0099340 A1 | 7/2002 | Crawford et al. |
| 2002/0151852 A1 | 10/2002 | Crawford et al. |
| 2002/0165497 A1 | 11/2002 | Greene |
| 2002/0173749 A1 | 11/2002 | Wagner et al. |
| 2002/0177816 A1 | 11/2002 | Brimhall et al. |
| 2002/0177818 A1 | 11/2002 | Vaillancourt |
| 2002/0183652 A1 | 12/2002 | Kensey |
| 2003/0060774 A1 | 3/2003 | Woehr et al. |
| 2003/0069546 A1 | 4/2003 | Sandstrom et al. |
| 2003/0093101 A1 | 5/2003 | O'Heeron et al. |
| 2003/0097098 A1 | 5/2003 | Lavi et al. |
| 2003/0105430 A1 | 6/2003 | Lavi et al. |
| 2003/0114797 A1 | 6/2003 | Vaillancourt et al. |
| 2003/0144627 A1 | 7/2003 | Woehr et al. |
| 2003/0148994 A1 | 8/2003 | Levinson |
| 2003/0181872 A1 | 9/2003 | Newby |
| 2003/0199827 A1 | 10/2003 | Thorne |
| 2004/0044318 A1 | 3/2004 | Fiser et al. |
| 2004/0049159 A1* | 3/2004 | Barrus ............ A61B 5/150732 604/174 |
| 2004/0156908 A1 | 8/2004 | Polaschegg |
| 2004/0225264 A1 | 11/2004 | Bourne et al. |
| 2004/0236288 A1 | 11/2004 | Howell et al. |
| 2005/0027263 A1 | 2/2005 | Woehr et al. |
| 2005/0090784 A1 | 4/2005 | Nielsen et al. |
| 2005/0107743 A1 | 5/2005 | Fangrow |
| 2005/0107748 A1 | 5/2005 | Thorne et al. |
| 2005/0107749 A1 | 5/2005 | Smith et al. |
| 2005/0107826 A1* | 5/2005 | Zhu .................. A61B 17/0057 606/213 |
| 2005/0124938 A1 | 6/2005 | Yang |
| 2005/0137528 A1 | 6/2005 | Wilkinson |
| 2005/0191355 A1 | 9/2005 | Foss |
| 2006/0064061 A1 | 3/2006 | Solomon et al. |
| 2006/0074387 A1 | 4/2006 | Thorne et al. |
| 2006/0155245 A1 | 7/2006 | Woehr |
| 2006/0161116 A1 | 7/2006 | Willis et al. |
| 2006/0182787 A1 | 8/2006 | Jaenichen et al. |
| 2006/0253076 A1 | 11/2006 | Butts et al. |
| 2006/0276836 A1 | 12/2006 | Bergin et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0073221 A1 | 3/2007 | Bialecki et al. |
| 2007/0073222 A1 | 3/2007 | Lilley et al. |
| 2007/0078432 A1 | 4/2007 | Halseth et al. |
| 2007/0191771 A1 | 8/2007 | Moyer |
| 2007/0191772 A1 | 8/2007 | Wojcik |
| 2008/0015481 A1 | 1/2008 | Bergin et al. |
| 2008/0063693 A1 | 3/2008 | Cook et al. |
| 2008/0147003 A1 | 6/2008 | Menzi et al. |
| 2008/0243082 A1 | 10/2008 | Goodman |
| 2008/0262434 A1 | 10/2008 | Vaillancourt |
| 2009/0005743 A1 | 1/2009 | Vaillancourt et al. |
| 2009/0143737 A1 | 6/2009 | Kobayashi et al. |
| 2009/0157000 A1 | 6/2009 | Waller |
| 2009/0254050 A1 | 10/2009 | Bottcher |
| 2009/0281499 A1 | 11/2009 | Harding et al. |
| 2010/0076362 A1 | 3/2010 | Utterberg et al. |
| 2010/0100049 A1 | 4/2010 | Godfrey |
| 2010/0152677 A1 | 6/2010 | Vaillancourt et al. |
| 2010/0179473 A1 | 7/2010 | Genosar |
| 2010/0312183 A1 | 12/2010 | Halseth et al. |
| 2011/0009831 A1* | 1/2011 | Burkholz ................ A61P 31/00 604/265 |
| 2011/0021997 A1 | 1/2011 | Kyvik et al. |
| 2011/0106014 A1 | 5/2011 | Helm, Jr. |
| 2011/0111012 A1 | 5/2011 | Pepper et al. |
| 2011/0295207 A1* | 12/2011 | Brugger ................ A61M 5/158 604/164.04 |
| 2011/0301619 A1 | 12/2011 | Walters |
| 2012/0046612 A1 | 2/2012 | Scheremet et al. |
| 2012/0046621 A1 | 2/2012 | Vaillancourt et al. |
| 2012/0065587 A1 | 3/2012 | Barron et al. |
| 2012/0089069 A1 | 4/2012 | Patel |

(56) References Cited

U.S. PATENT DOCUMENTS

| | | | |
|---|---|---|---|
| 2012/0130315 A1 | 5/2012 | Weadock et al. | |
| 2012/0184922 A1 | 7/2012 | Halseth et al. | |
| 2013/0110025 A1 | 5/2013 | Donnellan et al. | |
| 2013/0150791 A1 | 6/2013 | Peterson et al. | |
| 2013/0150796 A1 | 6/2013 | Souza et al. | |
| 2013/0172260 A1 | 7/2013 | Polaschegg | |
| 2013/0190724 A1 | 7/2013 | Polaschegg | |
| 2013/0274667 A1* | 10/2013 | Conrad-Vlasak | A61F 13/025 604/117 |
| 2013/0310764 A1 | 11/2013 | Burkholz et al. | |
| 2014/0039416 A1 | 2/2014 | Vaillancourt | |
| 2014/0058354 A1 | 2/2014 | Halseth et al. | |
| 2014/0066894 A1 | 3/2014 | Pearce et al. | |
| 2014/0330221 A1* | 11/2014 | Hen | A61L 24/06 604/290 |
| 2015/0297867 A1 | 10/2015 | Howell et al. | |
| 2019/0160261 A1 | 5/2019 | VanderStek | |

FOREIGN PATENT DOCUMENTS

| | | |
|---|---|---|
| CN | 101309714 A | 11/2008 |
| CN | 103497278 A | 1/2014 |
| DE | 3808688 A1 | 1/1989 |
| DE | 3802353 A1 | 8/1989 |
| DE | 20210394 U1 | 9/2002 |
| EP | 0344606 A2 | 12/1989 |
| EP | 451040 A1 | 10/1991 |
| EP | 0747082 A2 | 12/1996 |
| EP | 0763369 A1 | 3/1997 |
| EP | 1350537 A1 | 10/2003 |
| EP | 1430921 A2 | 6/2004 |
| EP | 2436421 A1 | 4/2012 |
| EP | 2613824 A1 | 7/2013 |
| FR | 2684006 A1 | 5/1993 |
| JP | H03-000077 A | 1/1991 |
| JP | 61-25558 A | 5/1994 |
| JP | 6226919 A | 8/1994 |
| JP | H06-304254 A | 11/1994 |
| JP | 7-148270 A | 6/1995 |
| JP | H07-299142 A | 11/1995 |
| JP | 9099071 A | 4/1997 |
| JP | 2001-218844 A | 8/2001 |
| JP | 2002345955 A | 12/2002 |
| JP | 2003-305128 A | 10/2003 |
| JP | 2004-195227 A | 7/2004 |
| JP | 2007-521918 A | 8/2007 |
| JP | 4355567 | 8/2009 |
| JP | 2010-000300 A | 1/2010 |
| WO | 1988007387 A1 | 10/1988 |
| WO | 1994000172 A1 | 1/1994 |
| WO | 1998006642 | 2/1998 |
| WO | 1999059660 A1 | 11/1999 |
| WO | 2004020033 A1 | 3/2004 |
| WO | 2005049116 A1 | 6/2005 |
| WO | 2006134100 A1 | 12/2006 |
| WO | 2007094898 A2 | 8/2007 |
| WO | 2012034085 A1 | 3/2012 |
| WO | 2012/132774 A1 | 10/2012 |

OTHER PUBLICATIONS

EP 03257490 filed Nov. 27, 2003 Office Action dated Aug. 9, 2007.
EP 03257490 filed Nov. 27, 2003 Search Report dated Jul. 23, 2004.
EP 15814436.0 filed Jan. 11, 2017 Extended European Search Report dated Feb. 1, 2018.
JP 2003-416415 filed Dec. 15, 2003 Office Action dated Feb. 23, 2007.
JP 2003-416415 filed Dec. 15, 2003 Office Action dated May 30, 2006.
JP 2016-185696 filed Sep. 23, 2016 Office Action dated Jul. 3, 2017.
JP 2016-185696 filed Sep. 23, 2016 Office Action dated Mar. 27, 2018.
JP2013-528355 filed Jan. 25, 2013, First Office Action dated Jun. 23, 2015.
JP2013-528355 filed Jan. 25, 2013, Second Office Action dated May 31, 2016.
PCT/US11/51102 International Preliminary Report on Patentabillity dated Mar. 21, 2013.
PCT/US11/51102 International Search Report and Written Opinion dated Dec. 23, 2011.
PCT/US2015/038853 filed Jul. 1, 2015 International Search Report and Written Opinion dated Oct. 6, 2015.
U.S. Appl. No. 10/320,168, filed Dec. 16, 2002 Advisory Action dated Aug. 22, 2005.
U.S. Appl. No. 10/320,168, filed Dec. 16, 2002 Advisory Action dated Nov. 16, 2005.
U.S. Appl. No. 10/320,168, filed Dec. 16, 2002 Final Office Action dated Jul. 13, 2005.
U.S. Appl. No. 10/320,168, filed Dec. 16, 2002 Non-Final Office Action dated Sep. 3, 2004.
U.S. Appl. No. 10/320,168, filed Dec. 16, 2002 Notice of Allowance dated Aug. 29, 2011.
U.S. Appl. No. 10/320,168, filed Dec. 16, 2002 Notice of Allowance dated May 13, 2011.
U.S. Appl. No. 10/787,605, filed Feb. 26, 2004 Advisory Action dated Jul. 16, 2007.
U.S. Appl. No. 10/787,605, filed Feb. 26, 2004 Final Office Action dated Apr. 4, 2008.
U.S. Appl. No. 10/787,605, filed Feb. 26, 2004 Final Office Action dated Jan. 20, 2010.
U.S. Appl. No. 10/787,605, filed Feb. 26, 2004 Final Office Action dated Jan. 25, 2007.
U.S. Appl. No. 10/787,605, filed Feb. 26, 2004 Non-Final Office Action dated Jul. 28, 2006.
U.S. Appl. No. 10/787,605, filed Feb. 26, 2004 Non-Final Office Action dated Oct. 2, 2008.
U.S. Appl. No. 10/787,605, filed Feb. 26, 2004 Non-Final Office Action dated Sep. 10, 2007.
U.S. Appl. No. 11/788,542, filed Apr. 20, 2007 Decision on Appeal dated Oct. 24, 2012.
U.S. Appl. No. 11/788,542, filed Apr. 20, 2007 Examiner's Answer dated Jun. 3, 2010.
U.S. Appl. No. 11/788,542, filed Apr. 20, 2007 Final Office Action dated Dec. 16, 2009.
U.S. Appl. No. 11/788,542, filed Apr. 20, 2007 Non-Final Office Action dated Aug. 27, 2008.
U.S. Appl. No. 11/788,542, filed Apr. 20, 2007 Non-Final Office Action dated Jan. 8, 2009.
U.S. Appl. No. 11/788,542, filed Apr. 20, 2007 Non-Final Office Action dated Jul. 10, 2009.
U.S. Appl. No. 12/221,034, filed Jul. 30, 2008 Final Office Action dated Dec. 8, 2009.
U.S. Appl. No. 12/221,034, filed Jul. 30, 2008 Non-Final Office Action dated Jan. 30, 2009.
U.S. Appl. No. 12/221,034, filed Jul. 30, 2008 Non-Final Office Action dated Jun. 26, 2009.
U.S. Appl. No. 12/221,034, filed Jul. 30, 2008 Notice of Allowance dated Feb. 25, 2010.
U.S. Appl. No. 12/855,605, filed Aug. 12, 2010 Final Office Action dated Oct. 4, 2011.
U.S. Appl. No. 12/855,605, filed Aug. 12, 2010 Non-Final Office Action dated Apr. 27, 2011.
U.S. Appl. No. 12/855,605, filed Aug. 12, 2010 Notice of Allowance dated Dec. 12, 2011.
U.S. Appl. No. 13/229,573, filed Sep. 9, 2011 Advisory Action dated Aug. 5, 2014.
U.S. Appl. No. 13/229,573, filed Sep. 9, 2011 Final Office Action dated Jun. 20, 2014.
U.S. Appl. No. 13/229,573, filed Sep. 9, 2011 Final Office Action dated May 6, 2015.
U.S. Appl. No. 13/229,573, filed Sep. 9, 2011 Non-Final Office Action dated Nov. 27, 2013.
U.S. Appl. No. 13/229,573, filed Sep. 9, 2011 Non-Final Office Action dated Oct. 24, 2014.

(56) References Cited

OTHER PUBLICATIONS

U.S. Appl. No. 13/229,573, filed Sep. 9, 2011, Notice of Allowance dated Jul. 15, 2015.
U.S. Appl. No. 13/285,774, filed Oct. 31, 2011 Final Office Action dated Oct. 28, 2013.
U.S. Appl. No. 13/285,774, filed Oct. 31, 2011 Non-Final Office Action dated Dec. 13, 2012.
U.S. Appl. No. 13/285,774, filed Oct. 31, 2011 Non-Final Office Action dated Jul. 3, 2012.
U.S. Appl. No. 13/285,774, filed Oct. 31, 2011 Non-Final Office Action dated Jun. 3, 2013.
U.S. Appl. No. 13/434,368, filed Mar. 29, 2012 Non-Final Office Action dated Mar. 20, 2013.
EP 15814436.0 filed Jan. 11, 2017 Communication Pursuant to Article 94(3) dated May 6, 2020.
Lochman et al. "Nanofiber Micro-Dispersed Oxidized Cellulose as a Carver for Topical Antimicrobials: First Experience", vol. 11, No. 1, 2010 (Year: 2010).
U.S. Appl. No. 16/142,928, filed Sep. 26, 2018 Notice of Allowance dated Apr. 30, 2020.
U.S. Appl. No. 16/264,375, filed Jan. 31, 2019 Non-Final Office Action dated May 1, 2020.
U.S. Appl. No. 14/045,663, filed Oct. 3, 2013 Advisory Action dated May 12, 2016.
U.S. Appl. No. 14/045,663, filed Oct. 3, 2013 Final Office Action dated Dec. 12, 2016.
U.S. Appl. No. 14/045,663, filed Oct. 3, 2013 Final Office Action dated Feb. 25, 2016.
U.S. Appl. No. 14/045,663, filed Oct. 3, 2013 Non-Final Office Action dated Aug. 13, 2015.
U.S. Appl. No. 14/045,663, filed Oct. 3, 2013 Non-Final Office Action dated Jun. 15, 2016.
U.S. Appl. No. 14/045,663, filed Oct. 3, 2013 Notice of Allowance dated Mar. 15, 2017.
U.S. Appl. No. 14/070,246, filed Nov. 1, 2013 Advisory Action dated Nov. 29, 2016.
U.S. Appl. No. 14/070,246, filed Nov. 1, 2013 Examiner's Answer dated Jun. 23, 2017.
U.S. Appl. No. 14/070,246, filed Nov. 1, 2013 Final Office Action dated Oct. 21, 2015.
U.S. Appl. No. 14/070,246, filed Nov. 1, 2013 Final Office Action dated Sep. 22, 2016.
U.S. Appl. No. 14/070,246, filed Nov. 1, 2013 Non-Final Office Action dated Apr. 8, 2015.
U.S. Appl. No. 14/070,246, filed Nov. 1, 2013 Non-Final Office Action dated Mar. 14, 2016.
U.S. Appl. No. 14/070,319, filed Nov. 1, 2013 Notice of Allowance dated Jun. 23, 2014.
U.S. Appl. No. 14/789,341, filed Jul. 1, 2015 Advisory Action dated Feb. 7, 2019.
U.S. Appl. No. 14/789,341, filed Jul. 1, 2015 Final Office Action dated Dec. 31, 2018.
U.S. Appl. No. 14/789,341, filed Jul. 1, 2015 Non-Final Office Action dated Apr. 20, 2018.
U.S. Appl. No. 14/789,341, filed Jul. 1, 2015 Notice of Allowance dated Aug. 21, 2019.
U.S. Appl. No. 14/789,341, filed Jul. 1, 2015 Restriction Requirement dated Nov. 16, 2017.
U.S. Appl. No. 15/012,800, filed Feb. 1, 2016 Notice of Allowance dated Aug. 1, 2018.

* cited by examiner

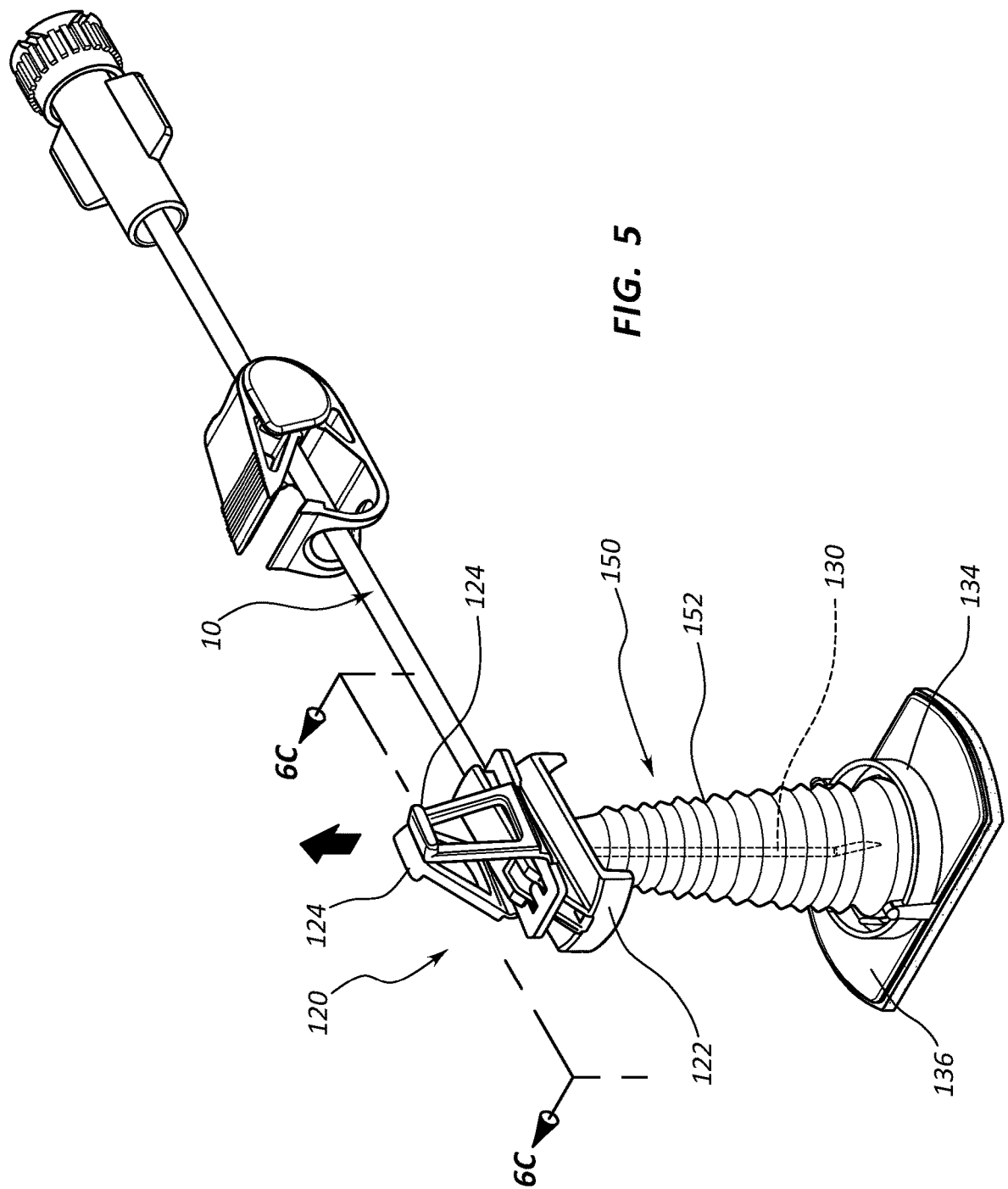

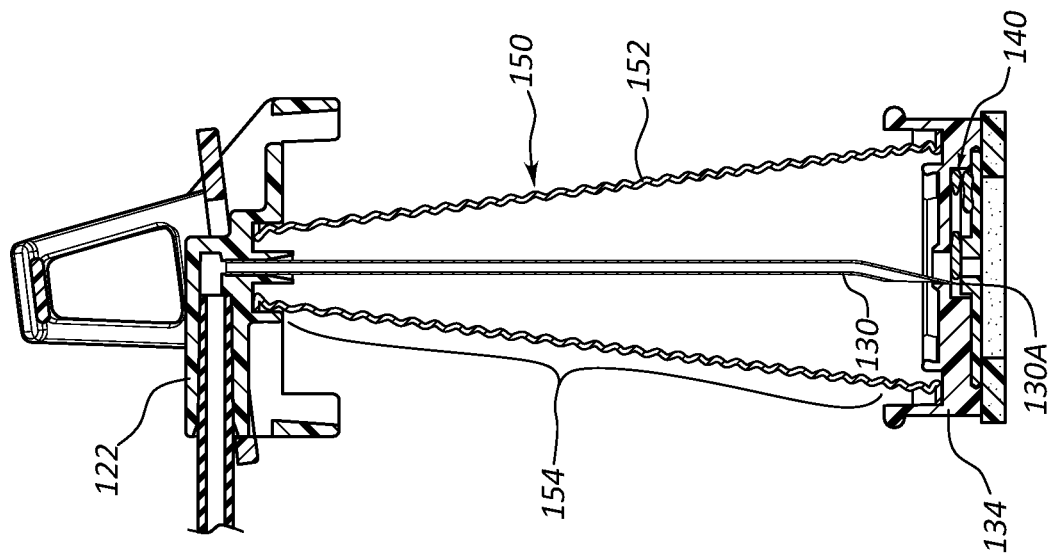
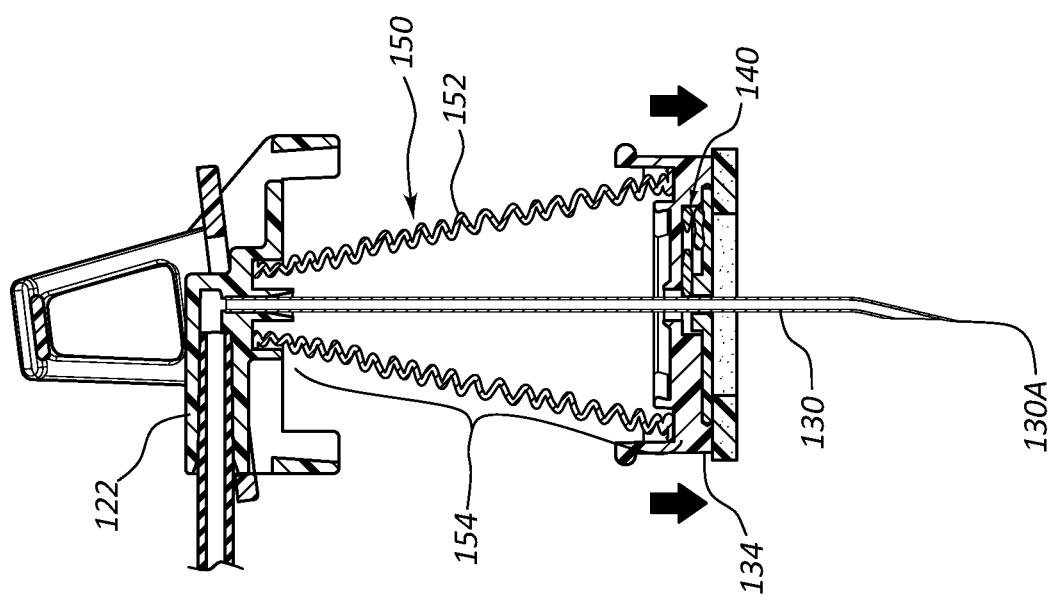
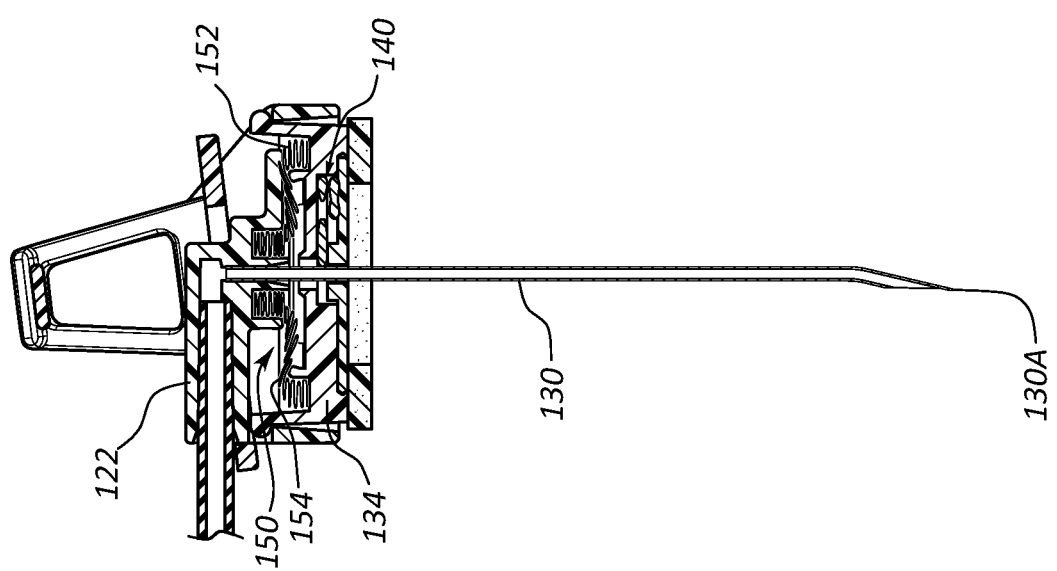

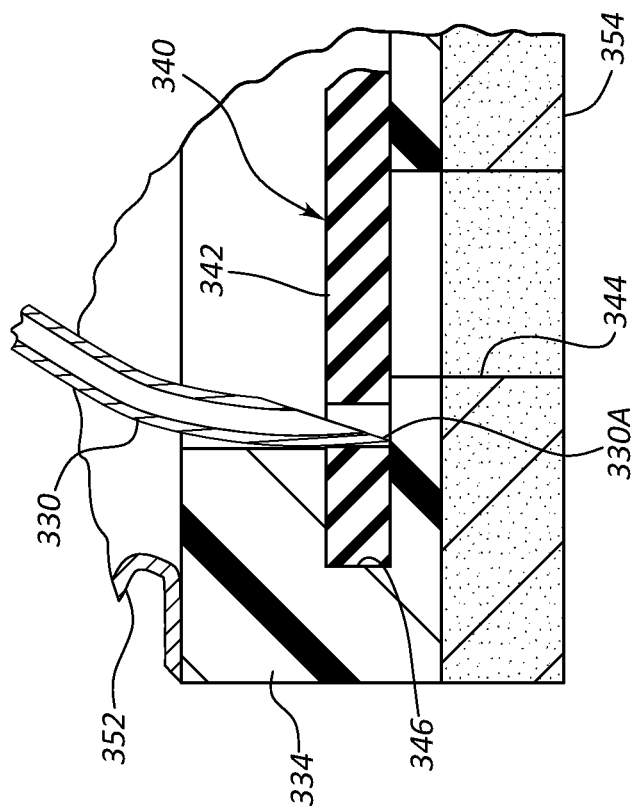
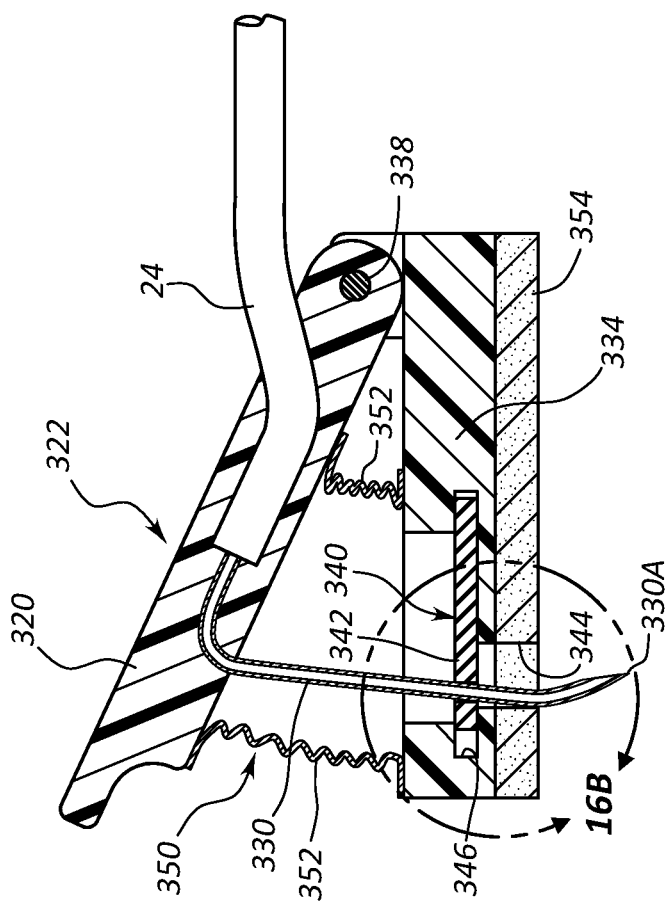
FIG. 16B
FIG. 16A

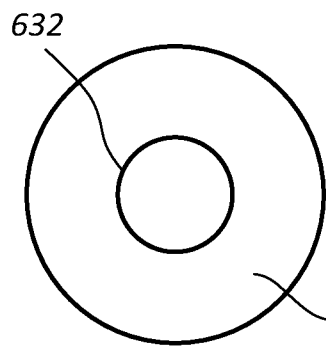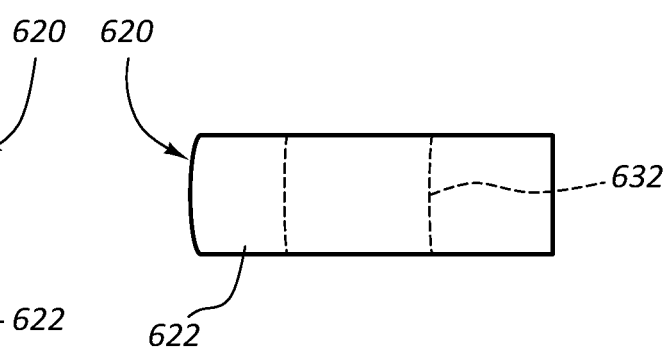
FIG. 27A  FIG. 27B
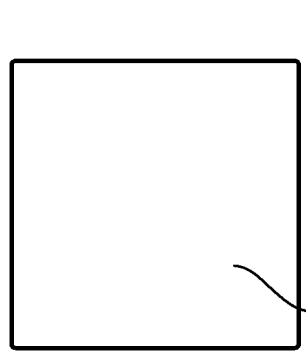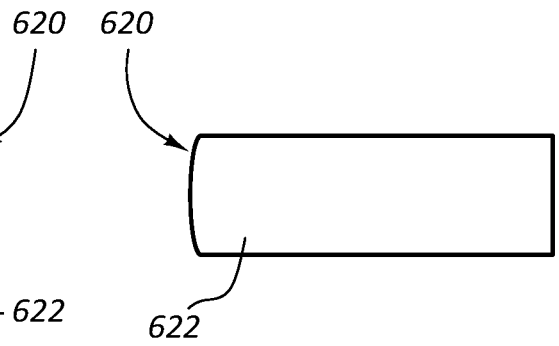
FIG. 28A  FIG. 28B
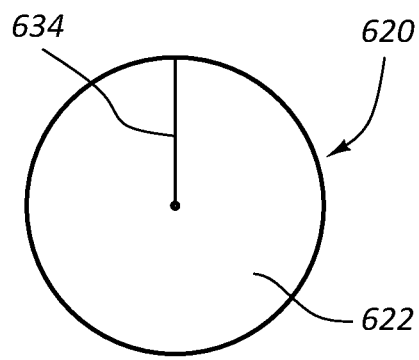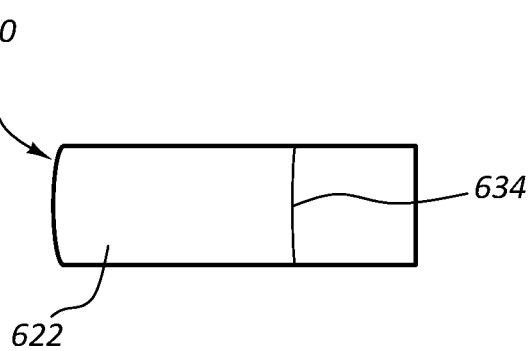
FIG. 29A  FIG. 29B

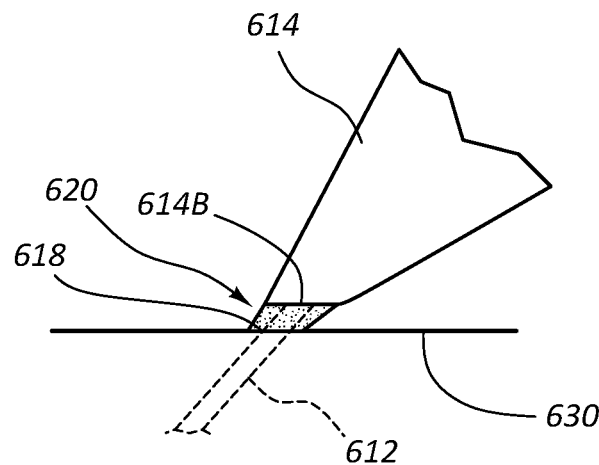
FIG. 33
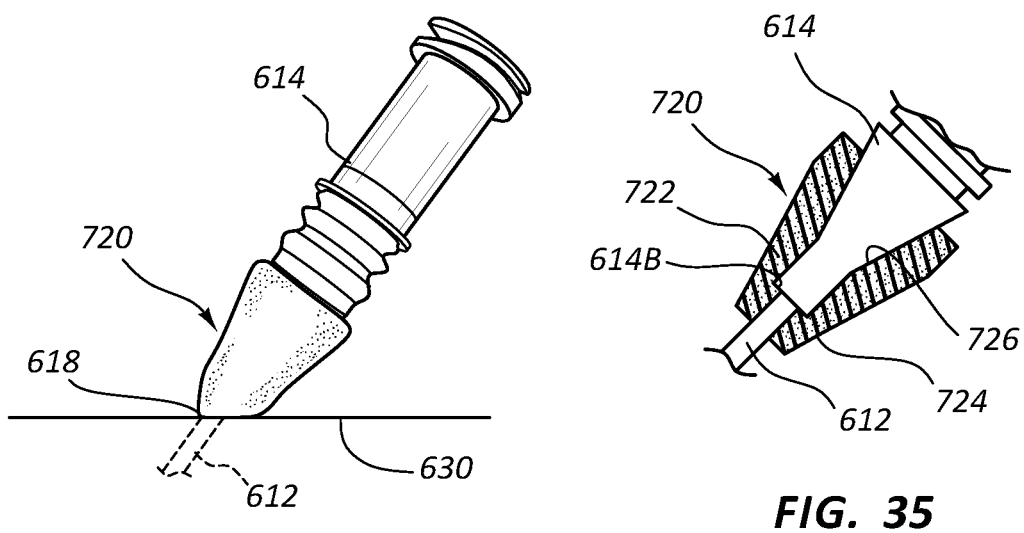
FIG. 34
FIG. 35

INSERTION DEVICE WITH INTERFACE PAD AND METHODS OF MAKING

CROSS-REFERENCE TO RELATED APPLICATIONS

This application is a division of U.S. patent application Ser. No. 14/789,341, filed Jul. 1, 2015, now U.S. Pat. No. 10,525,234, which claims priority to U.S. Provisional Application No. 62/019,807, filed Jul. 1, 2014, and which is a continuation-in-part of U.S. patent application Ser. No. 14/070,246, filed Nov. 1, 2013, which claims priority to U.S. Provisional Application No. 61/721,412, filed Nov. 1, 2012, and which is a continuation-in-part of U.S. patent application Ser. No. 13/229,573, filed Sep. 9, 2011, now U.S. Pat. No. 9,248,234, which claims priority to U.S. Provisional Application No. 61/381,762, filed Sep. 10, 2010. Each of the foregoing applications is incorporated herein by reference in its entirety.

BRIEF SUMMARY

Briefly summarized, embodiments of the present invention are directed to a safety needle assembly of an infusion set for infusing fluids into a subcutaneously implanted access port. The needle assembly is configured to prevent fluid escape therefrom so as to reduce or prevent fluid exposure to a clinician using the needle assembly.

In one embodiment, the needle assembly comprises a handle portion including a needle extending therefrom, the needle defining a lumen for passage of a fluid therethrough. The needle assembly also includes a safety assembly defining a needle hole through which the needle initially extends. The safety assembly is axially slidable along the needle in order to shield a distal tip of the needle and prevent user contact therewith. A fluid isolation component is included in the safety assembly for isolating fluid escape from the needle to prevent exposure to a clinician.

In one embodiment, a self-sealing pad is included on the safety assembly base through which the needle initially penetrates. When it is later shielded by the safety assembly after use, the needle is also retracted back through the self-sealing pad. The pad prevents any fluids that may have leaked from the distal opening of the needle from passing through the pad and escaping the needle assembly, thus preventing unintended exposure to the clinician.

In another embodiment, an interface pad is included on a bottom portion of the needle assembly and includes an antimicrobial and/or haemostatic agent to protect the needle insertion site. In yet another embodiment, the interface pad is included on a hub of a catheter assembly, or on a suitable portion of other medical devices, to protect the needle insertion site.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 5 shows a perspective view of the infusion set of FIG. 4 with the safety needle assembly in a second configuration;

FIGS. 6A-6C show actuation of the safety needle assembly of FIGS. 4 and 5;

FIGS. 16A and 16B are various views of a safety needle assembly according to one embodiment;

FIGS. 27A and 27B are various views of an interface pad according to one embodiment;

FIGS. 28A and 28B are various views of an interface pad according to one embodiment;

FIGS. 29A and 29B are various views of an interface pad according to one embodiment;

FIG. 33 is a side view of a catheter including an interface pad according to one embodiment;

FIG. 34 is a side view of a catheter including an interface pad according to one embodiment;

FIG. 35 is a cross sectional side view of the catheter and interface pad of FIG. 34;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. Also, the words "including," "has," and "having," as used herein, including the claims, shall have the same meaning as the word "comprising."

Embodiments of the present invention are generally directed to a safety infusion set and accompanying needle assembly for infusing fluids, such as chemotherapy agents or other medicaments for example, into an access port or other medical device subcutaneously implanted into the body of a patient. The infusion set and/or needle assembly includes one or more components for isolation of the fluid, including vapors thereof, which may otherwise leak from a needle or other portion of the infusion set. This in turn reduces or prevents possible clinician exposure to the fluid/vapors, which in some cases may be hazardous. Potential harm to the clinician is therefore reduced.

Figure 1:
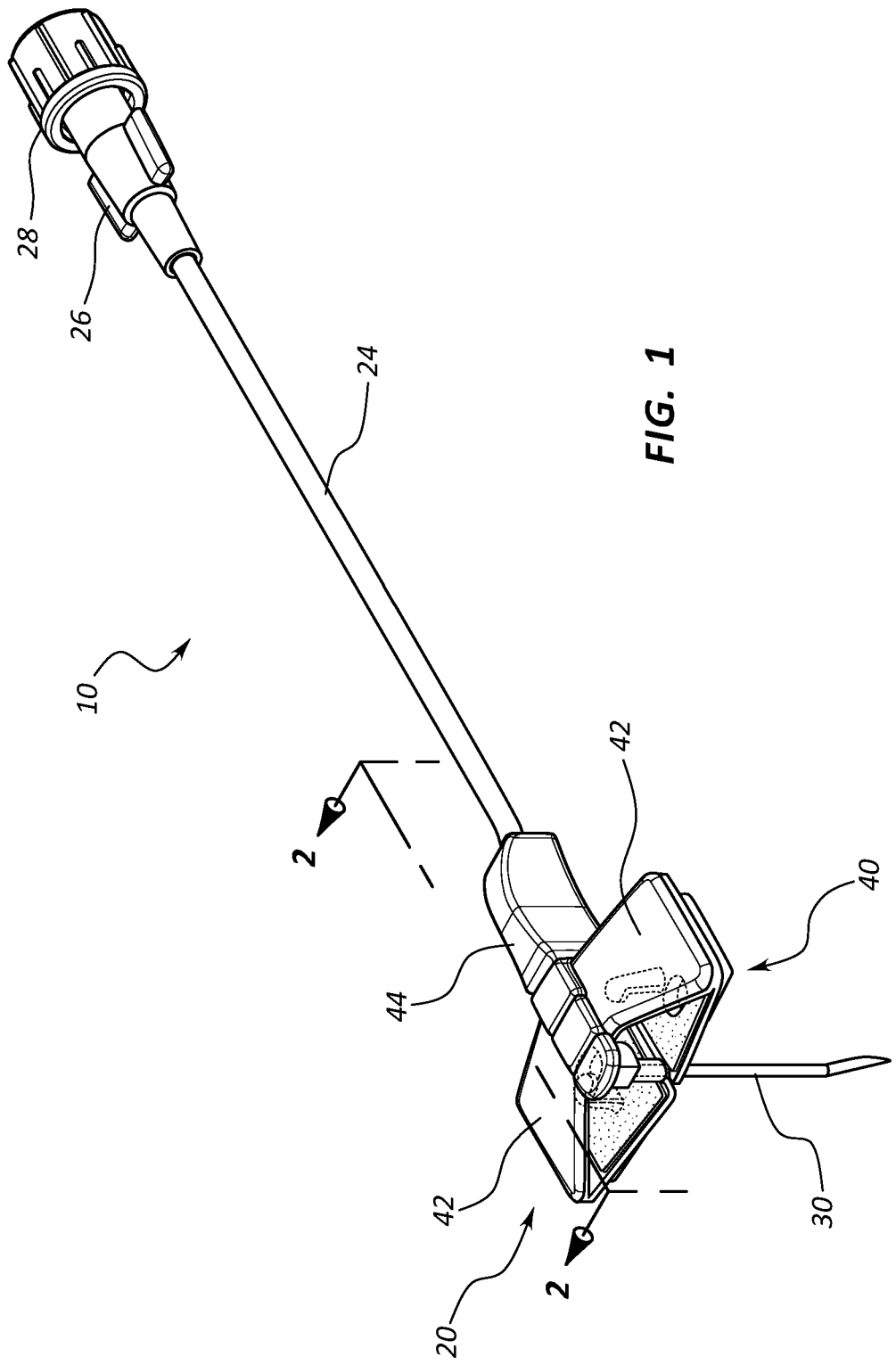
FIG. 1 is a perspective view of an infusion set including a safety needle assembly according to one embodiment.

Reference is first made to FIG. 1, which depicts an infusion set generally designated at 10, including a safety needle assembly ("needle assembly") 20 and one or more extension legs 24. The infusion set 10 is employed to gain access to a subcutaneously implanted access port or other device disposed below the skin of a patient in order to infuse medicaments or other fluids into the patient, and to withdraw fluids therefrom. A luer connector 26 is included on a proximal end of the extension leg 24 so as to enable the infusion set 10 to be placed into fluid communication with a fluid delivery device or system. A cap 28 can be disposed in the luer connector 26 to cover the opening thereof.

FIG. 1 shows that the needle assembly 20 includes a needle 30 extending from a handle 44 and in fluid communication with the tubing of the extension leg 24. A needle safety component 40 is also included in the needle assembly 20, including dual extensible wings that are hinged so as to be selectively extended to substantially cover the length of the needle 30 and isolate a distal end 30A thereof after use of the needle assembly 20 in order to prevent an unintended needle stick of the clinician by the needle tip. Examples of such a hinged safety assembly can be found in U.S. Pat. No. 5,951,522, which is incorporated herein by reference in its entirety.

Figure 2:
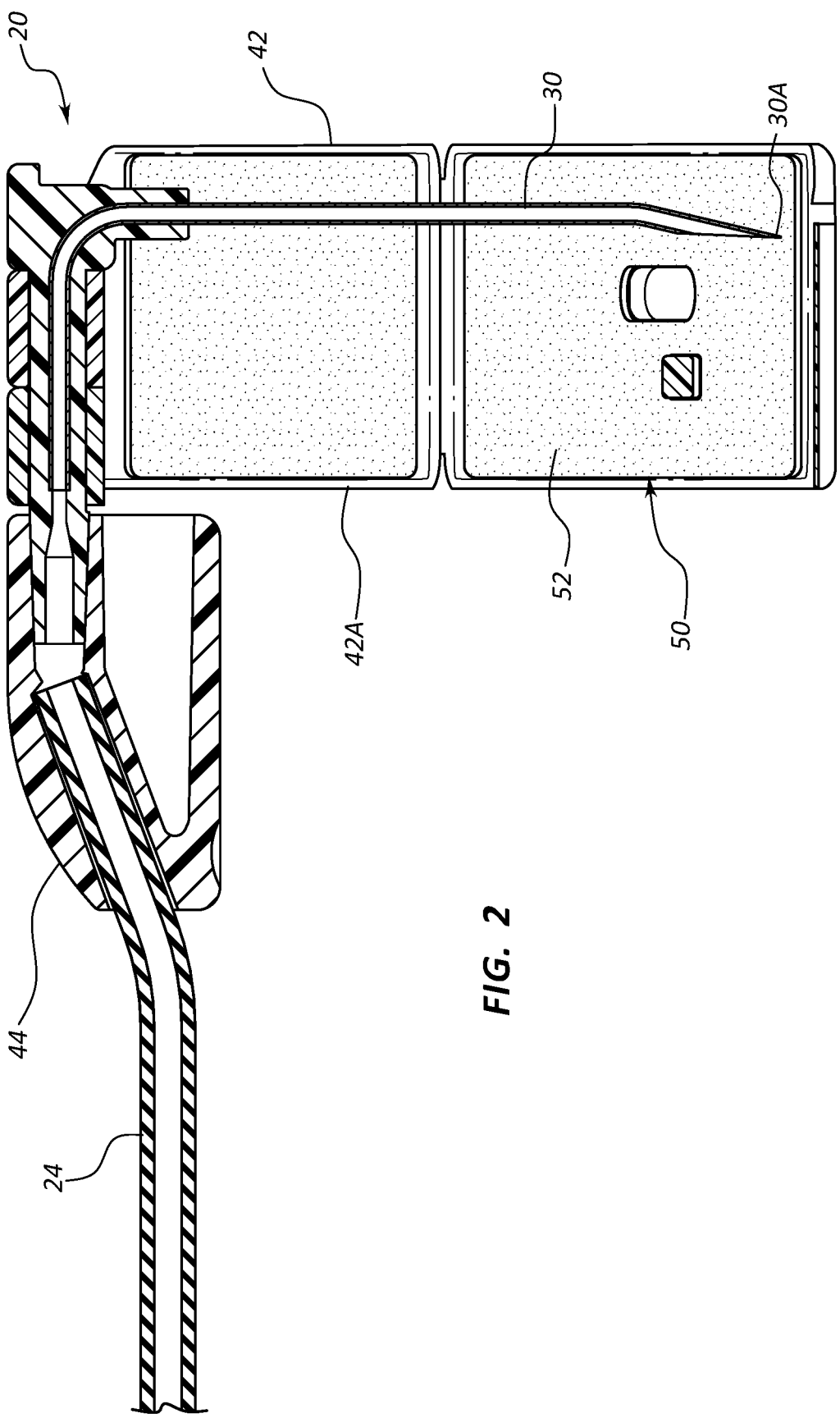
FIG. 2 is a side view of the needle assembly of FIG. 1.

As best seen in FIG. 2, the needle assembly 20 further includes a fluid isolation component 50 for isolating any fluid or vapor that may unintentionally escape from the needle 30 during use of the needle assembly. Specifically, the fluid isolation component 50 in the present embodiment includes absorbent pads 52 disposed on an inner surface 42A of each wing 42 of the needle safety component 40. The pads 52 are disposed such that when the wings 42 of the needle safety component 40 are deployed to cover the distal tip 30A of the needle 30 (FIG. 2), the pads sandwich the body and distal tip of the needle therebetween. Any fluid present on an external surface of the needle or any fluid/vapor leaking from the distal end thereof is captured and absorbed by the pads 52, thus preventing escape of the fluid, which as mentioned above may contain hazardous substances. This in turn protects the clinician from fluid exposure.

Figure 3C:
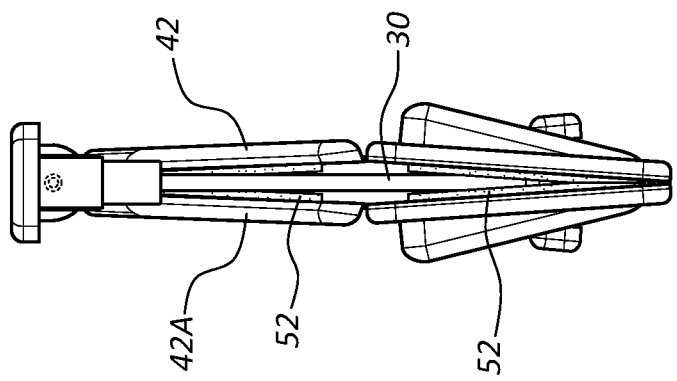
FIGS. 3A-3C show actuation of needle assembly of FIG. 1.
Figure 3B:
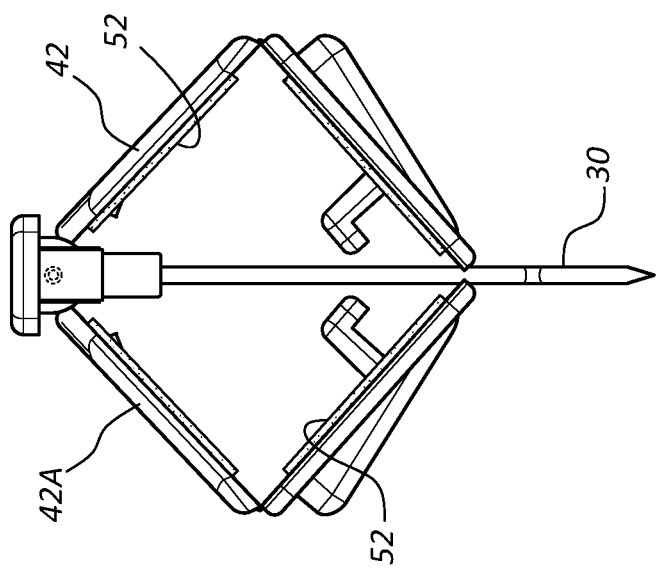
Figure 3A:
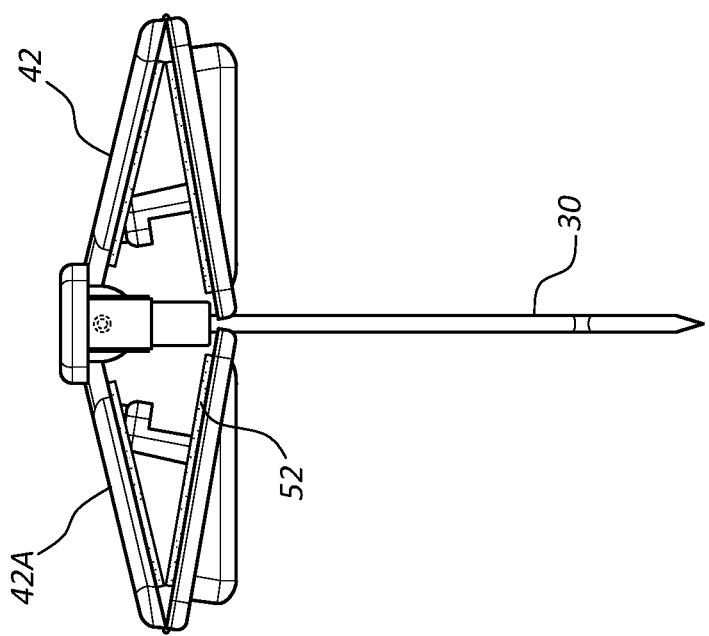

FIGS. 3A-3C show the manner in which the wings 42 of the needle safety component 40 extend to cover the needle 30 and its distal tip 30A, and additionally the manner in which the pads 52 sandwich and partially encapsulate the needle 30, including its external surfaces and its distal tip 30A, to prevent fluid/vapor escape. In one embodiment, the pads 52 can include an absorbent foam and/or rubber material, though many other suitable materials can be employed, including activated charcoal, etc.

Figure 4:
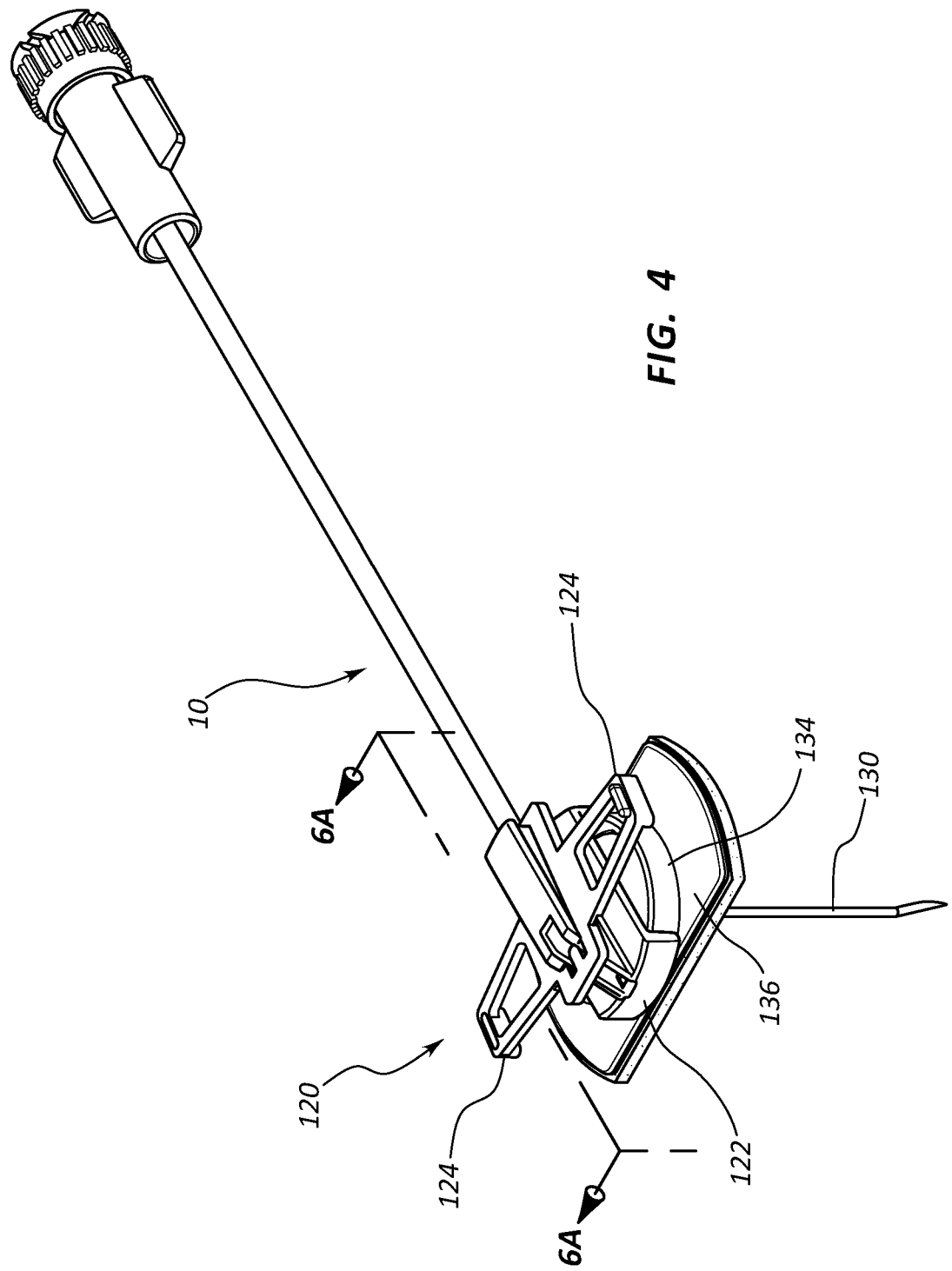
FIG. 4 shows a perspective view of an infusion set including a safety needle assembly in a first configuration according to one embodiment.

FIGS. 4 and 5 show the infusion set 10 including a needle assembly 120 according to another embodiment, wherein the needle assembly includes a handle portion 122 with handles 124 extending therefrom. A needle 130 extends from the handle portion 122 and initially through a safety assembly 134 that is slidably disposed with respect to the needle 130 so as to be axially slidable therewith. The safety assembly 134 includes a base 136 that houses a needle safety component 140 (FIGS. 8A, 8B) for shielding a distal tip 130A of the needle 130 when use of the needle assembly is complete.

The needle assembly 120 further includes a fluid isolation component 150 for isolating any fluid or vapor that may unintentionally escape from the needle 130 during use of the needle assembly. Specifically, the fluid isolation component 150 in the present embodiment includes a conically shaped, extensible shroud 152 disposed about the body of the needle 130 and extending between the handle portion 122 and the axially slidable safety assembly 134. Including plastic such as PET or other substantially impermeable, collapsible, and suitable durable material, the shroud 152 forms a hollow cone about the needle 130 and is corrugated with corrugations 154 in a bellows-like manner to enable it to fold up compactly when the safety assembly 134 is undeployed (FIG. 4) and to extend to cover and substantially encompass the needle 30 when the safety assembly 134 is deployed (FIG. 5), i.e., the safety assembly is axially slid down the needle 130 toward the distal tip 130A such that the needle safety component 140 shields the distal tip. FIGS. 6A-6C depict the manner of deployment of the safety assembly 134 and the extension of the corrugated shroud 152. In the extended state shown in FIGS. 5 and 6C, the shroud 152 assists in isolating fluids/vapors present on the needle 130 or emitted from the needle distal tip 130A from contact with the clinician.

Note that examples of safety needles that can utilize principles discussed here and in other embodiments herein can be found in the following United States patents: U.S. Pat. Nos. 7,717,888; 8,066,678; 8,597,253; and 8,231,582. Each of the afore-mentioned patents is incorporated herein by reference in their entirety.

Figure 7C:
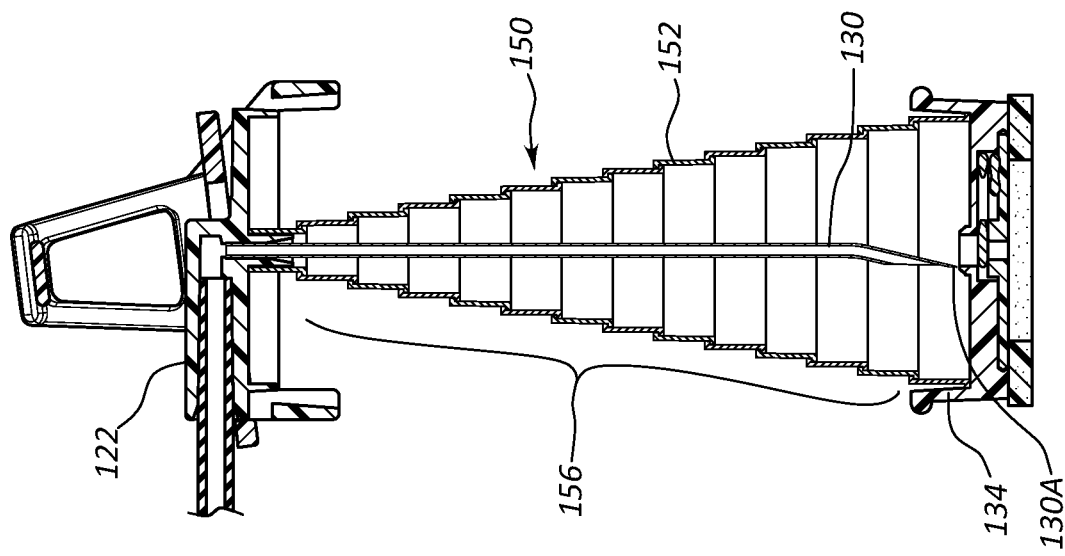
FIGS. 7A-7C shows actuation of a safety needle assembly according to another embodiment.
Figure 7B:
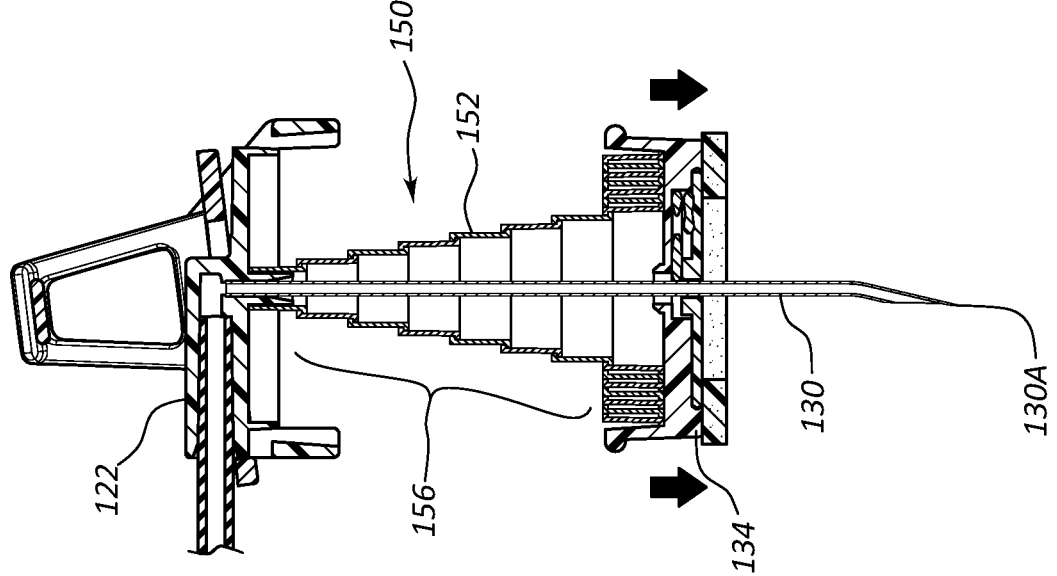
Figure 7A:
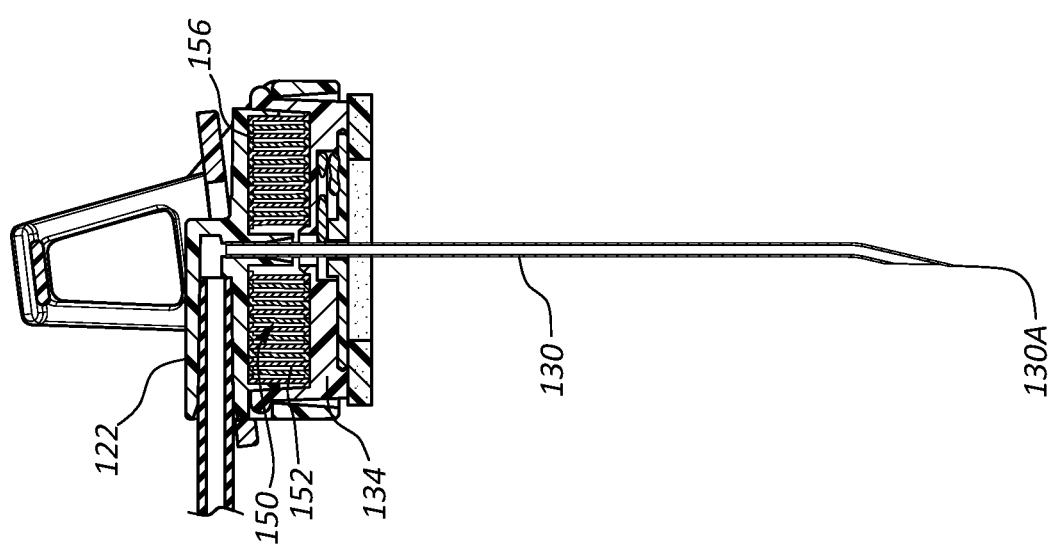

The shroud 152 as the fluid isolation component 150 can include other configurations. One such configuration is shown in FIGS. 7A-7C, wherein the shroud includes a plurality of interlocked, telescoping segments that are extendible to cover and encompass the needle body when the safety assembly 134 is deployed (FIG. 7C). When the safety assembly 134 is undeployed, the telescoping segments 156 are stacked together, as shown in FIG. 7A. Again, these and other configurations for encompassing the needle body illustrate manners by which a fluid isolation component can isolate the needle body and tip in order to prevent fluid exposure to clinician.

Figure 8A:
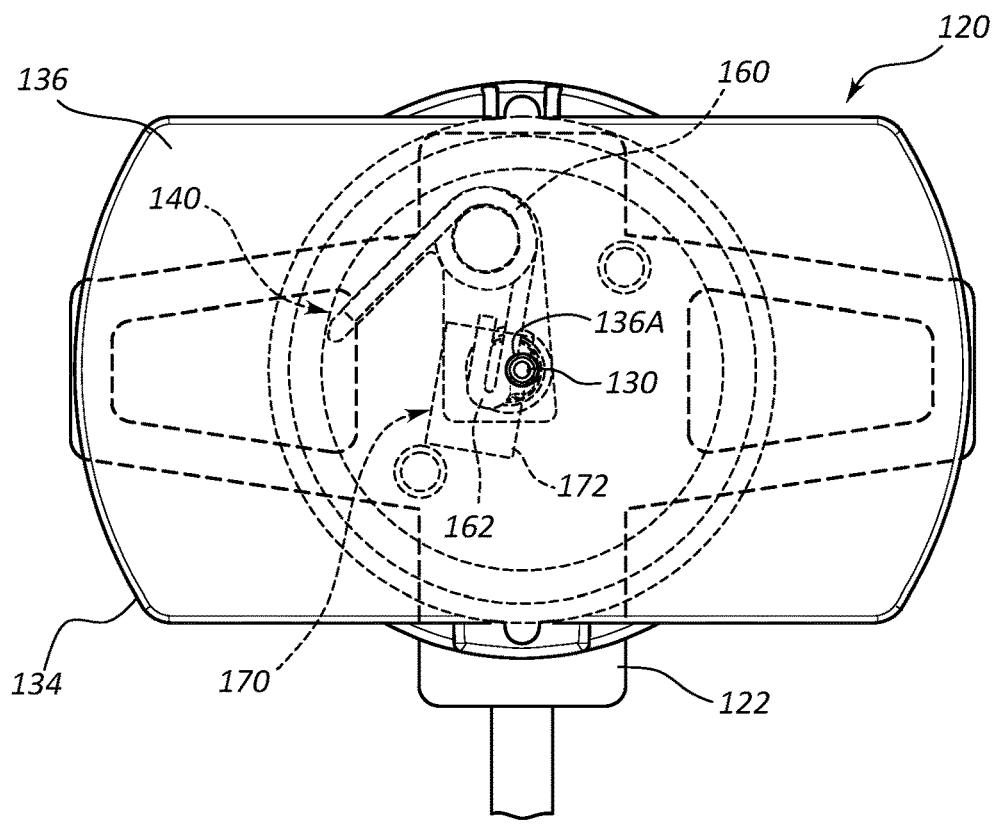
FIGS. 8A and 8B show a bottom view of a safety needle assembly including a fluid isolation component according to one embodiment.
Figure 8B:
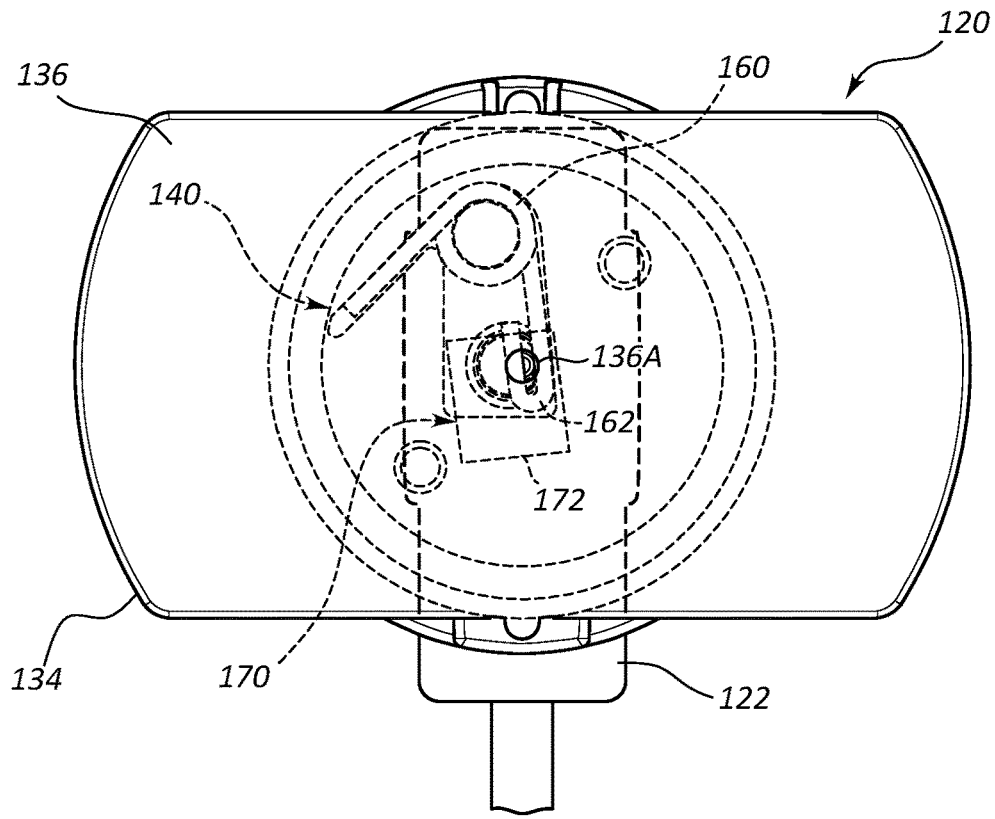

FIGS. 8A and 8B depict details of the needle safety component 140 of the needle assembly 120 of FIGS. 4-7C. Particularly, FIGS. 8A and 8B depict bottom views of the needle assembly 120. The needle safety component 140 is shown, including a coiled wire torsion spring 160 included within the base 136 of the safety assembly 134. The spring includes at one end thereof an obstruction component, i.e., a looped portion 162 that is biased to lie against the needle 130 when the needle extends through a hole 136A defined in the base 136 of the safety assembly 134, as shown in FIG. 8A. As shown in FIG. 8B, once the distal tip of the needle 130 is withdrawn into the base 136 in connection with extension of the safety assembly 134 (e.g., FIGS. 5, 6C, 7C), the spring 160 expands such that the looped portion 162 slides over the needle hole 136A to prevent re-emergence of the needle distal tip.

In addition, a fluid isolation component 170 is included with the spring 160 for isolating any fluid or vapor that may unintentionally escape from the needle 130 during use of the needle assembly. Specifically, the fluid isolation component 170 includes a shield 172, shown in FIGS. 8A and 8B, which is attached proximate the looped portion 162 of the spring 160. Thus, when the looped portion 162 slides over to prevent re-emergence of the distal tip 130A of the needle 130 through the hole 136A (FIG. 8B), the shield fully covers and occludes the hole so as to prevent any fluid/vapor leaking from the distal tip of the needle from exiting through the hole and potentially contaminating the environment or clinician. The shield 172 thus serves to occlude the hole 136A and isolate any fluids/vapors from the clinician. Note that the particular size, shape, and configuration of the shield can vary from what is shown and described herein, as can the particular configuration of the needle assembly. In one embodiment, it is appreciated that the shield can include an absorbent material so as to absorb any leaked fluid.

Figures 9A, 9B:
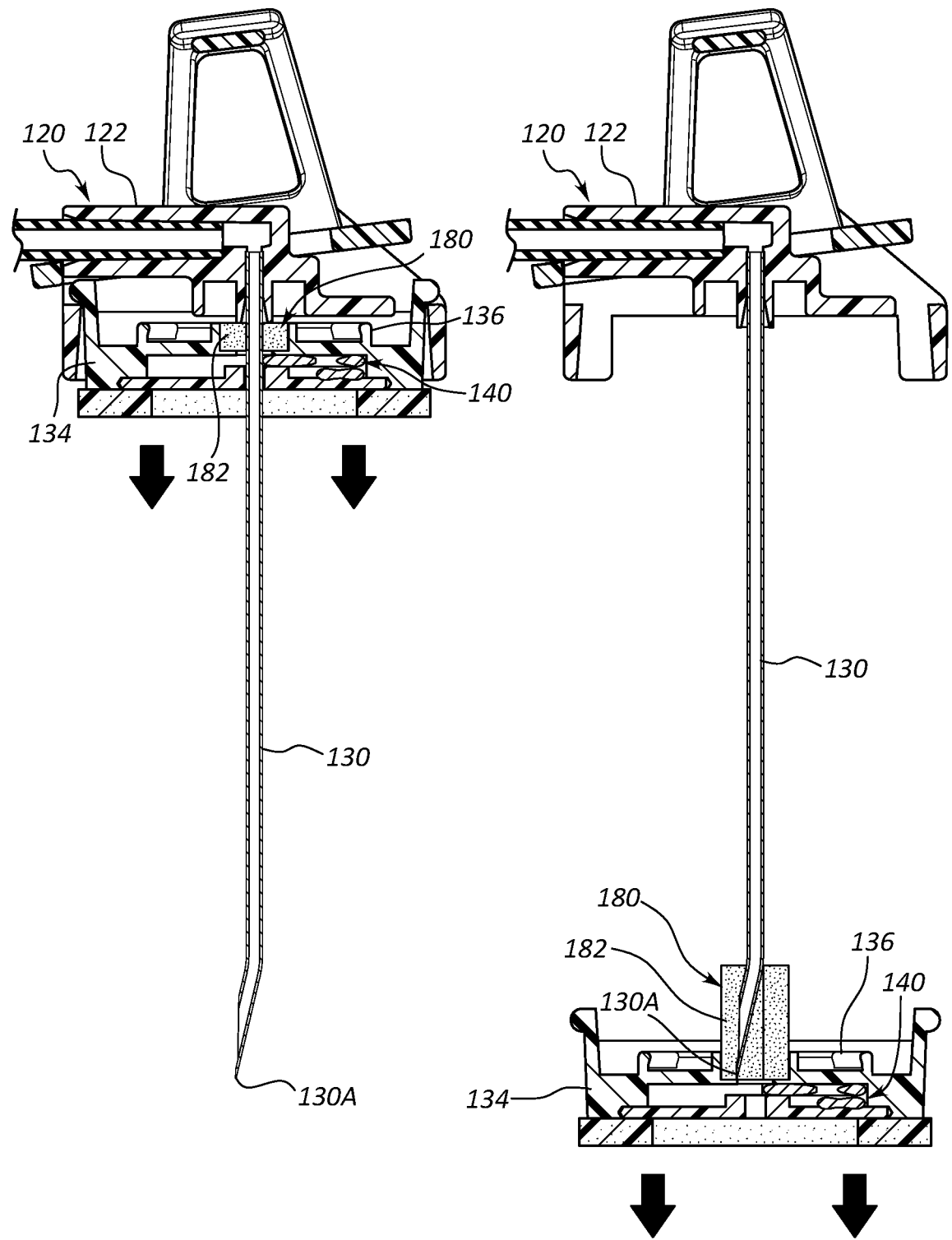
FIGS. 9A and 9B are cross sectional side views of a safety needle assembly including a fluid isolation component according to one embodiment.

FIGS. 9A and 9B depict details of the needle assembly 120 according to another embodiment, including a fluid isolation component 180 for isolating any fluid or vapor that may unintentionally escape from the needle 130 during use of the needle assembly. As shown, the fluid isolation component 180 in the present embodiment includes a cylindrical absorption plug 182 included with the axially slidable safety assembly 134 of the needle assembly 120 and including a central cavity so as to be positioned about a portion of the body of the needle 130 (FIG. 9A). The central cavity of the plug 182 is sized such that the plug is able to wipe the outer surface of the body of the needle 130 as the safety assembly 134 is axially slid down the needle toward the distal tip 130A thereof, thus removing fluid from the outer needle surface and capturing it in the plug itself. In addition, once the safety assembly 134 has fully shielded the needle distal tip 130A (FIG. 9B), the plug 182 is positioned about the distal opening of the lumen of the needle 130 so as to catch and absorb any fluids/vapors emanating therefrom.

It is appreciated that the absorption plug can include a variety of size, type, and material configurations, and can be employed on a variety of needle-based devices where residual fluid/vapor capture is desired. In one embodiment, for instance, the absorption member includes activated charcoal. In other embodiments, other materials and membranes can be employed, including silica gel, clays, activated alumina, zeolites, 0.2 micron or other filtration material, etc. The description included herein is therefore not intended to limit the present disclosure in any way.

Figure 10:
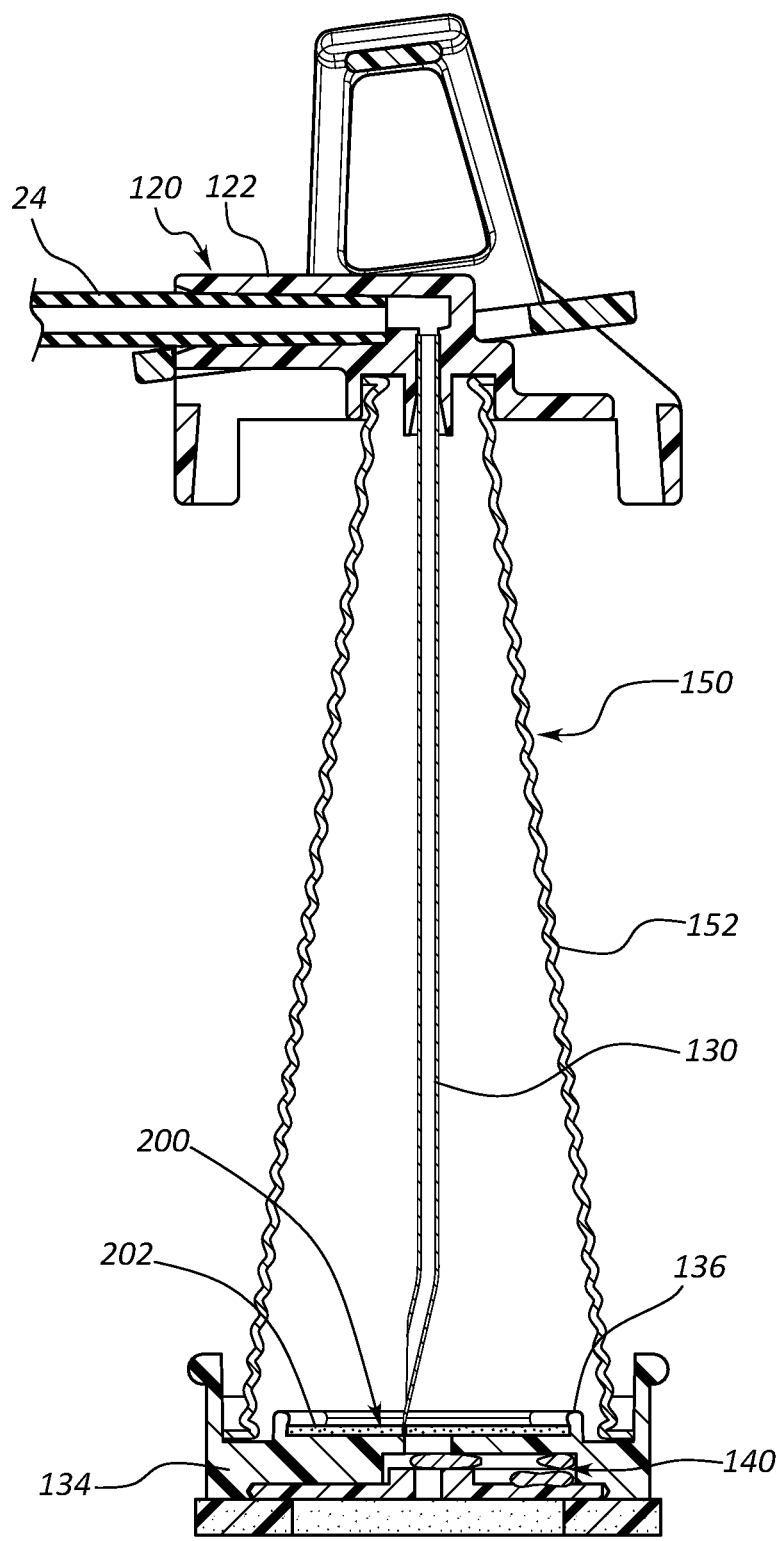
FIG. 10 is a cross sectional side view of a safety needle assembly including a fluid isolation component according to one embodiment.

FIG. 10 shows details of a fluid isolation component 200 according to another embodiment, including an absorption disk 202 included with the safety assembly 134. The absorption disk 202 is disposed above the needle safety component 140 in the safety assembly base 136 and is slit to enable the needle 130 to pass therethrough. Extension of the safety assembly 134 down the length of the needle 130 enables the absorption disk 202 to wipe the outer needle surface so as to remove any fluid present thereon. In addition, once the safety assembly 134 is fully extended to shield the needle 130 (FIG. 10), the absorption disk 202 is positioned so as to absorb any fluid/vapor leaking from the distal lumen opening at the needle distal tip 130A. As with the previous embodiment, the absorption disk 202 in one embodiment includes activated charcoal or other suitable, absorbent material as outlined above in connection with the absorption plug 182 shown in FIGS. 9A and 9B. The position, shape, thickness or other configuration of the absorption disk can vary from what is shown and described herein.

Figure 11:
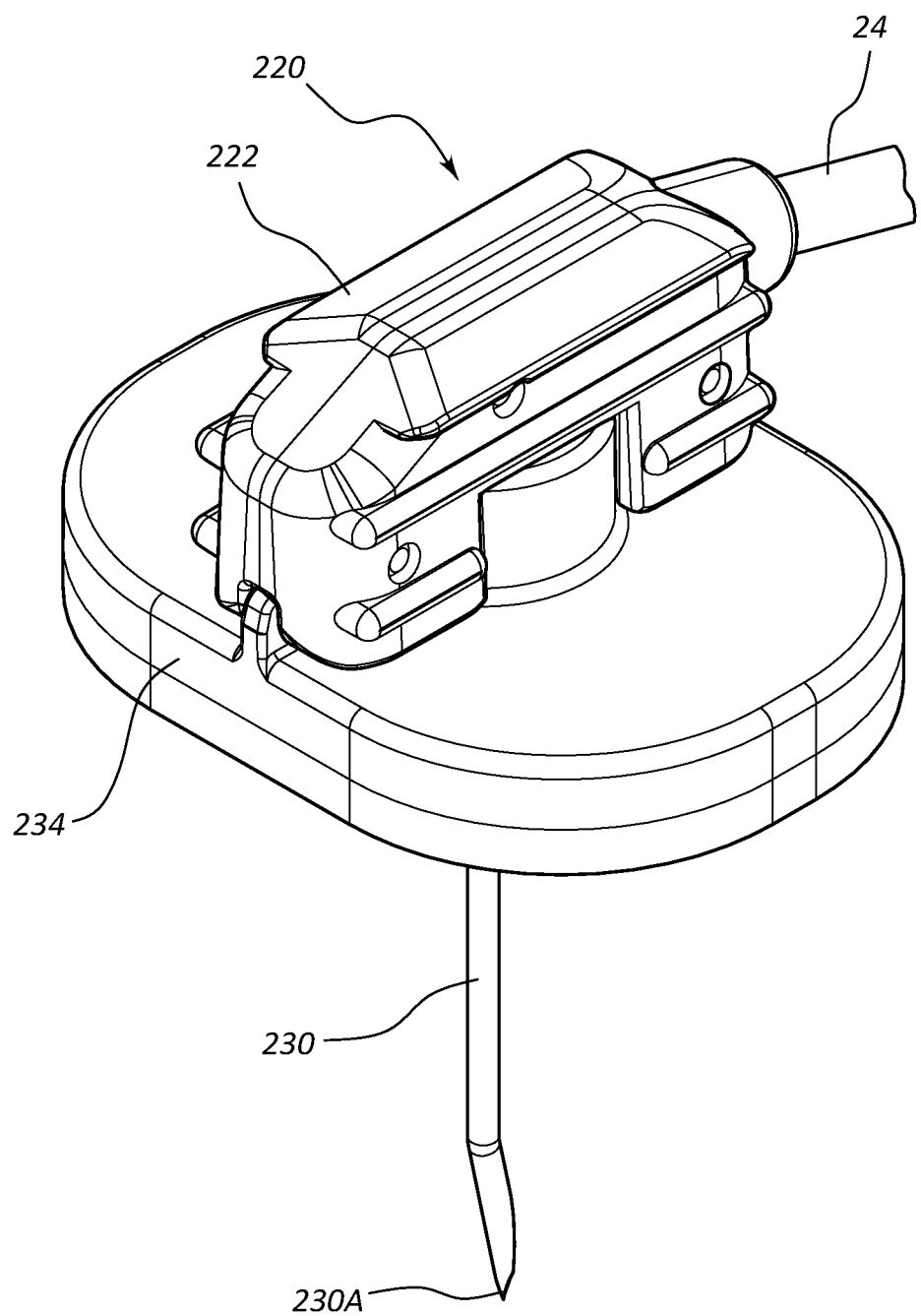
FIG. 11 is a perspective view of a safety needle assembly according to one embodiment.
Figure 12A:
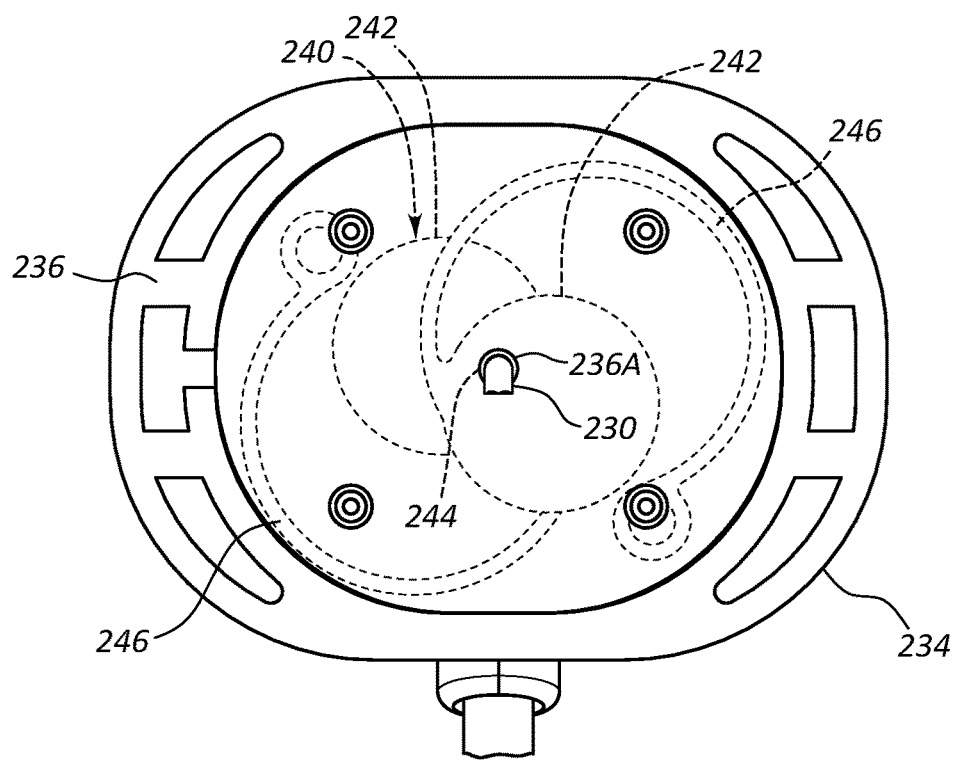
FIGS. 12A and 12B are bottom views of the safety needle assembly of FIG. 11.
Figure 12B:
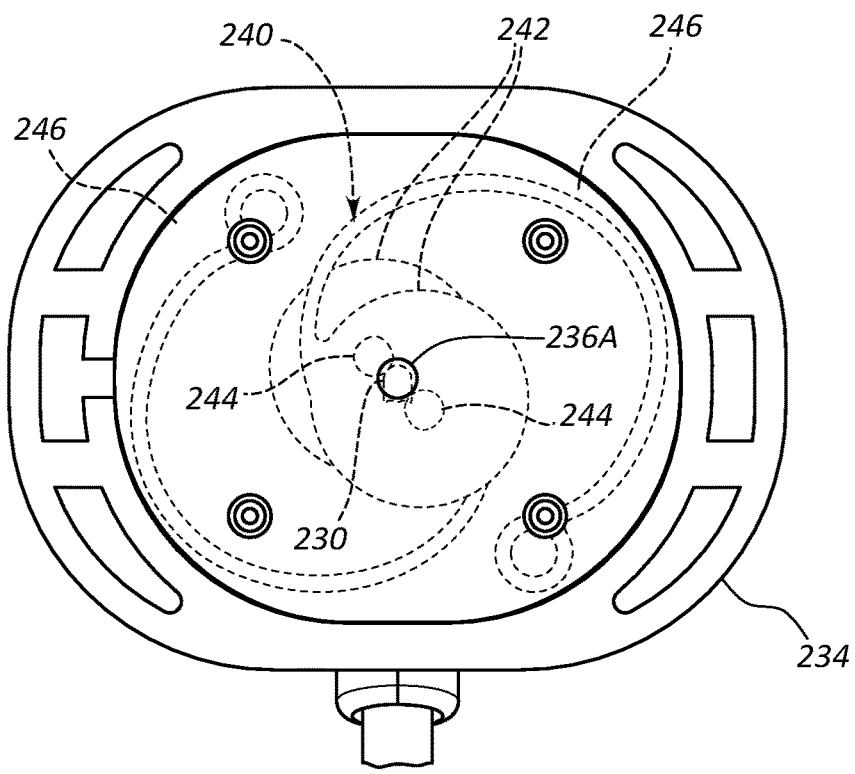

FIGS. 11-12B depict various details of a needle assembly 220 that can include a fluid isolation component, according to one embodiment. As shown, the needle assembly 220 includes a handle portion 222 from which extends a needle 230. The needle 230 initially extends through a safety assembly 234 that is slidably disposed with respect to the needle so as to be axially slidable therewith. The safety assembly 234 includes a base 236 that houses a needle safety component 240 (FIGS. 12A, 12B) for shielding a distal tip 230A of the needle 230 when use of the needle assembly is complete.

In greater detail, FIGS. 12A and 12B show that the needle safety component 234 includes two spring-based shutters 242 that each define a hole 244 through which the needle 230 passes when the needle extends through the safety assembly 234 and out a hole 236A defined in the base 236, such as in the configuration shown in FIG. 11. The shutters 242 each further include a spring arm 246. As seen in FIG. 12A, when the safety assembly 234 is undeployed (FIG. 11), the holes 244 of the shutters 242 are aligned so that the needle 230 passes therethrough. This constrains the shutters 242 and spring arms 246 into the configuration shown in FIG. 12A.

When the safety assembly 234 is actuated, however, it is slid down the length of the needle 230 so as to cause the needle distal tip 230A to recede from the hole 236A and the shutter holes 244 so as to be shielded within the safety assembly base 236. As shown in FIG. 12B, this causes the shutters 242 to no longer be constrained by the needle 230 and enables the shutter spring arms 246 to slide the shutters laterally within the base 236 so as to cover and occlude the hole 236A defined in the base, thus preventing reemergence of the needle distal tip 230A. Note that further information regarding this and other related needle safety assemblies can be found in U.S. Pat. No. 6,585,704 to Luther et al., titled "Method of Retaining a Tip Protector on a Needle with a Curved Tip."

Figure 13:
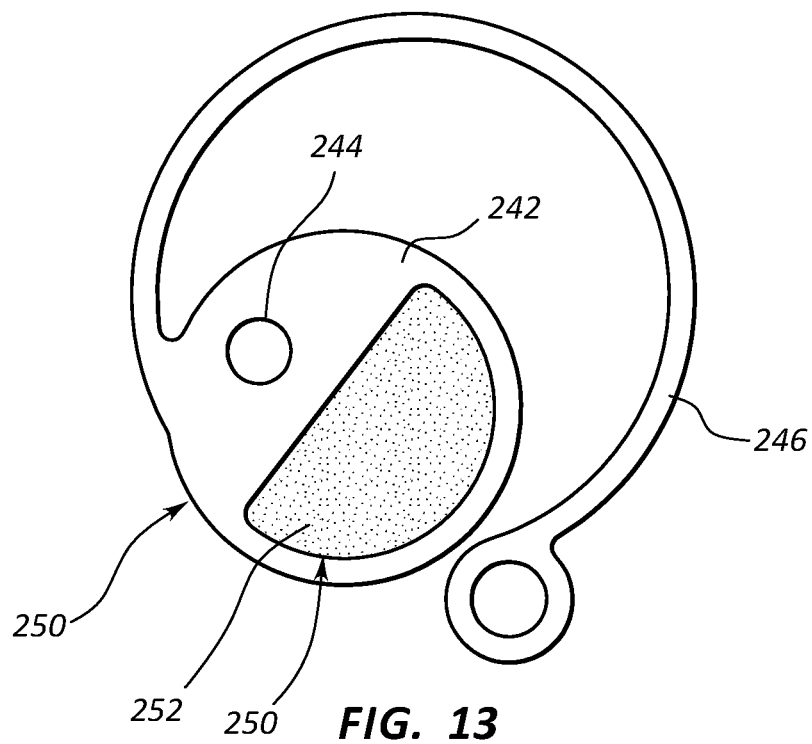
FIG. 13 is a top view of a shutter of the safety needle assembly of FIG. 10, including a fluid isolation component according to one embodiment.
Figure 14:
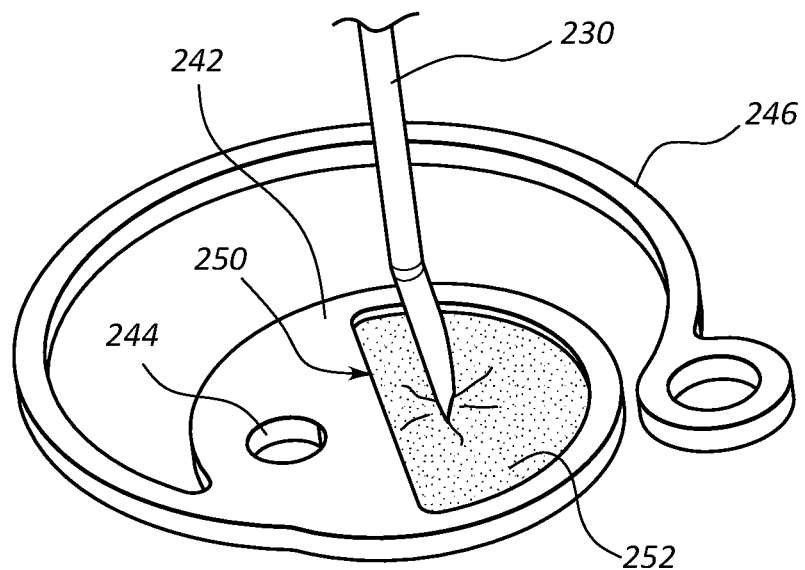
FIG. 14 is a perspective view of the shutter of FIG. 13 including the fluid isolation component.

In accordance with one embodiment the needle assembly 220 includes a fluid isolation component 250 for isolating any fluid or vapor that may unintentionally escape from the needle 130 during use of the needle assembly. Specifically, the fluid isolation component 250 in the present embodiment includes an absorption pad 252 disposed on a backside of one or both of the shutters 242 of the safety assembly 234. As shown in FIGS. 13 and 14, the pad 252 is disposed on the shutter 242 so that the distal tip 230A of the needle 230 rests against it after the distal tip has been withdrawn and shielded by the base 236 of the safety assembly 234. Should any fluid leak from the distal opening of the lumen of the needle 230, it can be readily captured by the pad 252, thus preventing its escape outside of the safety assembly 234. The pad can include one or more of suitable materials including those listed above in connection with the embodiment of FIGS. 9A and 9B, silicone, rubber, etc. As shown, the pad can also be recessed within the shutter 242 so as to provide a basin for capture of the fluid, in one embodiment. Note that the pad and shutters can vary in size, number, shape, design, etc.

Figure 15:
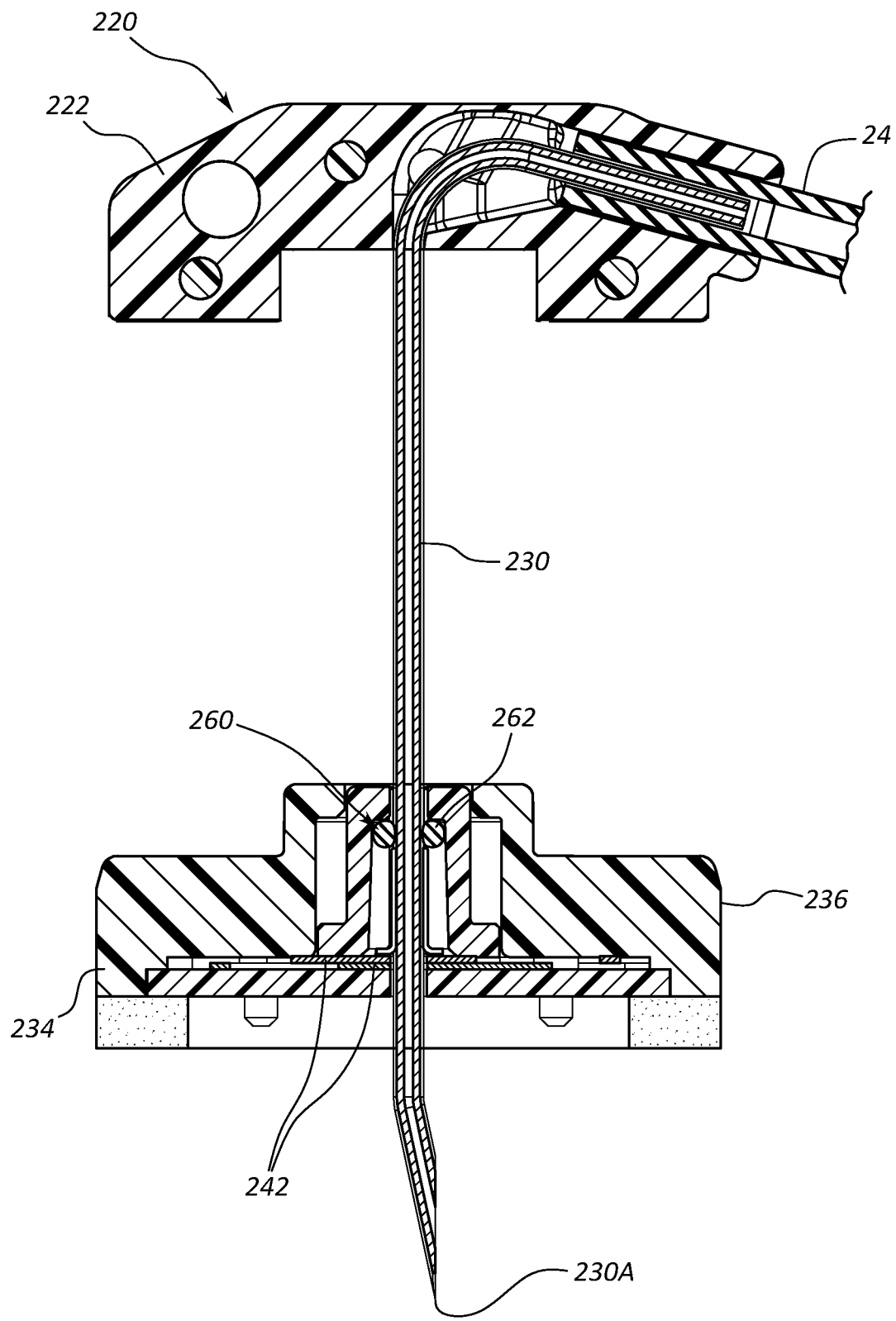
FIG. 15 is a cross sectional side view of a safety needle assembly according to one embodiment.

FIG. 15 shows the needle assembly 220 including a fluid isolation component 260 according to one embodiment, wherein the fluid isolation component includes an O-ring 262 that is disposed within the safety assembly 234 about a portion of the needle 230. So positioned, the O-ring 262 wipes the length of the needle 230 when the safety assembly 234 is axially slid down the needle in order to shield the needle distal tip 230A. The O-ring 262 is sized such that its wiping action cleans the outer needle surface of any fluids that might otherwise be exposed to the clinician and prevents their escape from the safety assembly base 236. In one embodiment, the O-ring can be configured to be absorbent so as to soak up any fluid it comes into contact with during wiping of the needle. Note that the O-ring can be placed in other locations with respect to the needle safety assembly and that the needle housing and safety assembly can vary in configuration from what is shown.

FIGS. 16A and 16B depict various details of a needle assembly 320 including a fluid isolation component, according to one embodiment. The needle assembly 320 includes a handle portion 322 from which extends a needle 330. The needle 330 initially extends through a hole 344 defined in a safety assembly 334 that is pivotally movable with respect to the handle portion 322 and the needle 330 via a hinge point 338. The safety assembly 334 houses a needle safety component 340 including a laterally slidable shutter 342, disposed in a shutter cavity 346, for shielding a distal tip 330A of the needle 230 when use of the needle assembly is complete. A foam pad 354 is disposed on the bottom of the safety assembly 334.

As shown in FIG. 16B, the needle 330 is biased while residing in the hole 344 of the safety assembly 334 such that when the distal tip 330A is withdrawn from the hole, the needle 330 urges the shutter 342 to laterally slide within the shutter cavity 346, thus covering the hole and preventing re-emergence of the needle distal tip. In another embodiment, the shutter itself can be biased to urge the needle distal tip laterally.

The needle assembly 320 further includes a fluid isolation component, here configured as an extensible shroud 352 that extends about the needle 330 between the handle portion 322 and the safety assembly 334 to isolate the body of the needle and any vapors present therewith. Thus, the shroud 352 provides isolation of fluids present on the needle 330. In addition, the shutter 342 provides some fluid isolation as well.

Figure 17:
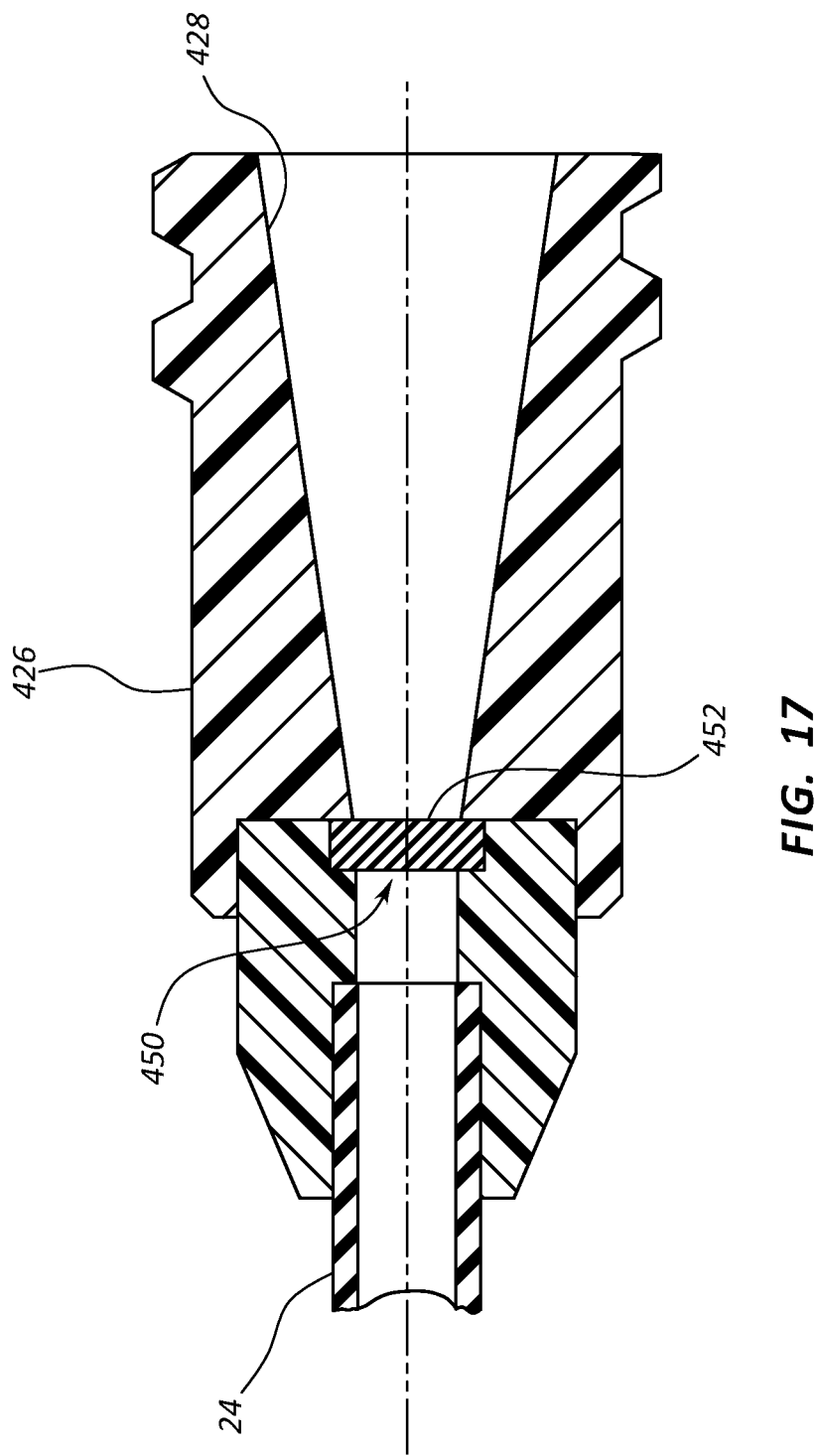
FIG. 17 is a cross sectional side view of a luer connector including a fluid isolation component according to one embodiment.
Figure 18B:
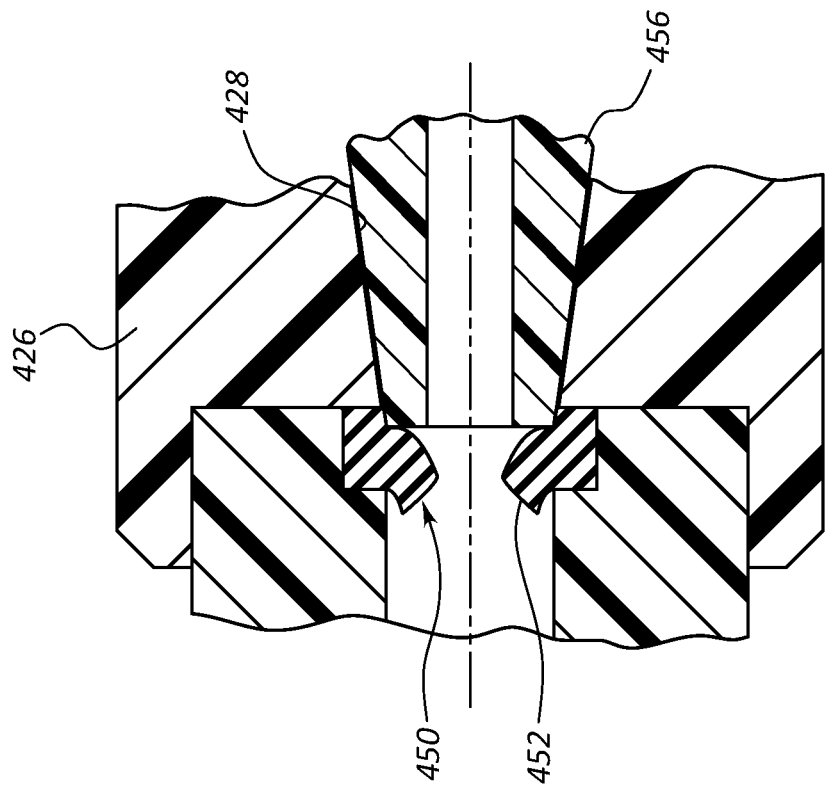
FIGS. 18A-18B are cross sectional side views of the luer connector of FIG. 17 during use.
Figure 18A:
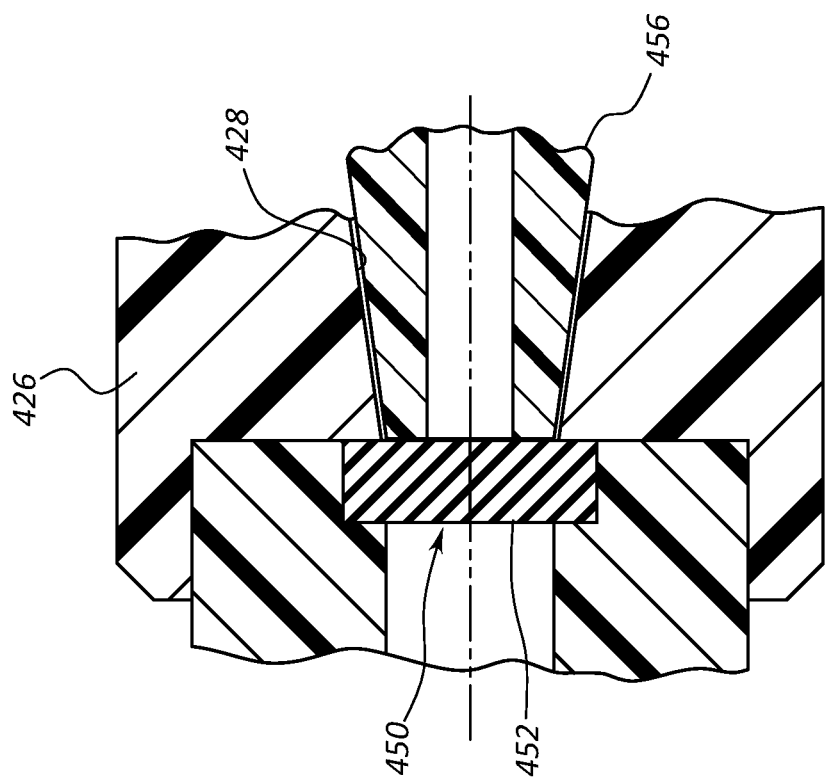

FIGS. 17-18B disclose a luer connector 426 including a fluid isolation component, according to one embodiment. As shown, the connector 426 is a female-type luer connector, though the principles described here can be extended to other connective or fluid-carrying components of an infusion set or other suitable fluid delivery medical device. Connected to the extension leg tubing 24, the connector 426 includes a body that defines a cavity 428 suitable for receiving a male-type connector 456 (FIGS. 18A, 18B) therein. The connector 426 can include threads to enable the male connector 456 to threadably connect therewith. The cavity 428 defines a portion of a fluid pathway through the connector body.

A fluid isolation component 450 is included in the connector 426. In particular, the fluid isolation component 450 in the present embodiment includes a slit valve 452 that is disposed in the fluid pathway defined by the connector 426. Other suitable types of valves may also be employed.

As seen in FIGS. 18A and 18B, when the male connector 456 is received but not fully seated within the cavity 428 of the female connector 426, the valve 452 remains closed, thus isolating any fluid contained in the extension leg tubing 24 attached thereto. When the male connector 456 is fully inserted into the female connector 426, the distal end of the male connector engages and opens the valve 452, thus allowing fluid flow therethrough. This configuration of the connector 426 thus serves as one example a connector-based fluid isolation component; other configurations of this principle are contemplated.

Figure 19A:
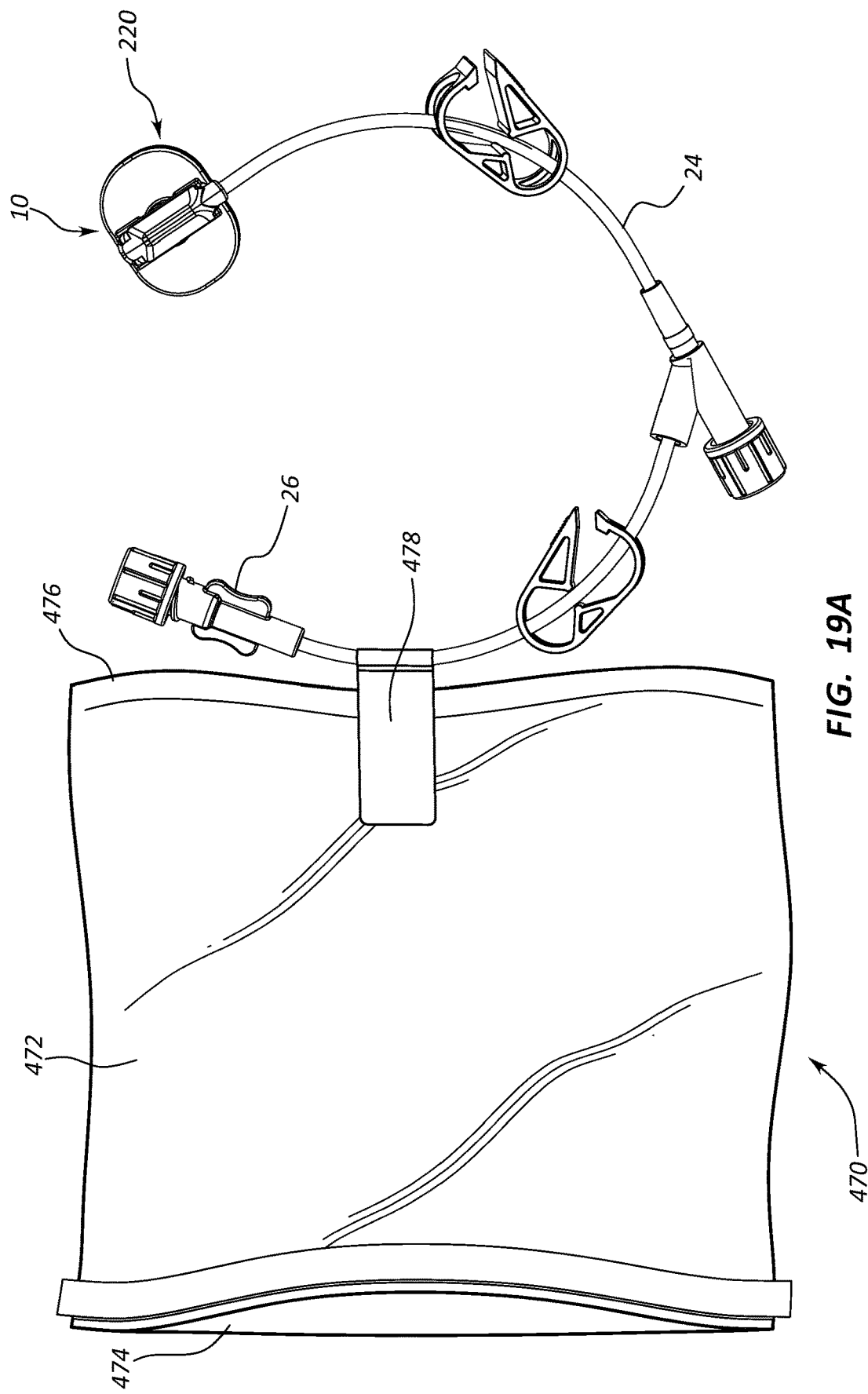
FIGS. 19A and 19B show various views of a fluid isolation component together with an infusion set, according to one embodiment.
Figure 19B:
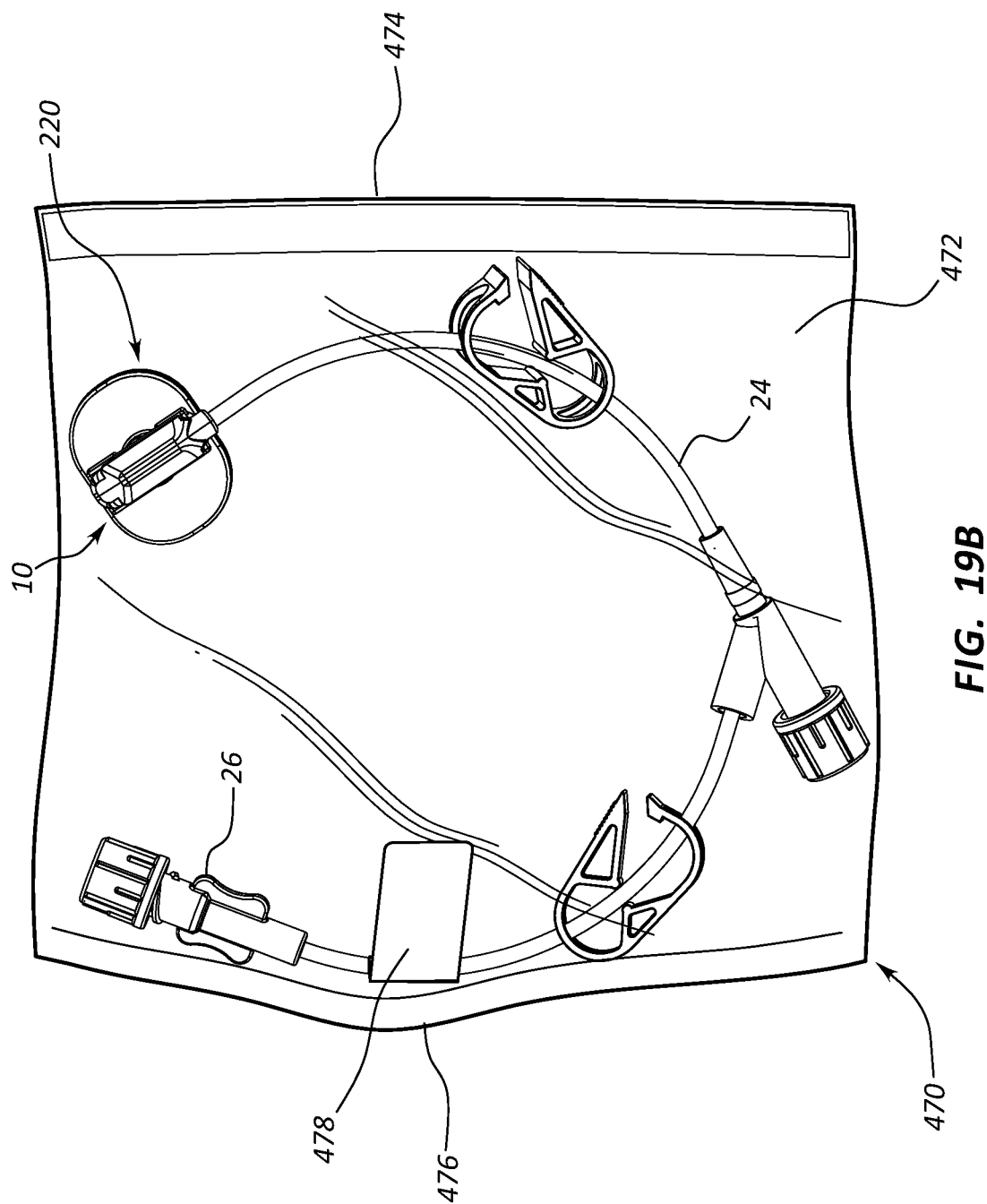

FIGS. 19A and 19B depict another example of a fluid isolation component for preventing unintended contact with fluid or vapors resulting from use of an infusion set. In particular, an infusion set 10 is shown, including a needle assembly 220, extension leg tubing 24, and luer connector 26. Also shown is a fluid isolation component 470, which in the present embodiment includes a bag 472 of plastic or other substantially fluid-impermeable material. The bag includes a sealable open end 474 and a closed end 476. The bag 472 is attached to the tubing 24 of the infusion set 10 or other suitable component thereof via and adhesive strip 478 or other suitable connective apparatus.

The bag 472 is initially inside-out before use of the infusion set 10. Once use of the infusion set 10 has ended, the user reaches a hand through the open end 474 of the bag 472 and pulls the infusion set into the bag, turning the bag right side-out in the process. Once the infusion set 10 is fully within the bag 472, the open end 474 of the bag 472 is sealed, as seen in FIG. 19B, thus isolating the user from any fluids or vapors included on the needle assembly 220 or any other portion of the infusion set 10. Note that the bag can be configured in one or more sizes and shapes, can include one-time, resealable, or other suitable type of sealing mechanism, and can be included with the infusion set in a variety of ways, both attached and detached thereto. The bag in the present embodiment is transparent, though in other embodiments it need not be.

Figure 20:
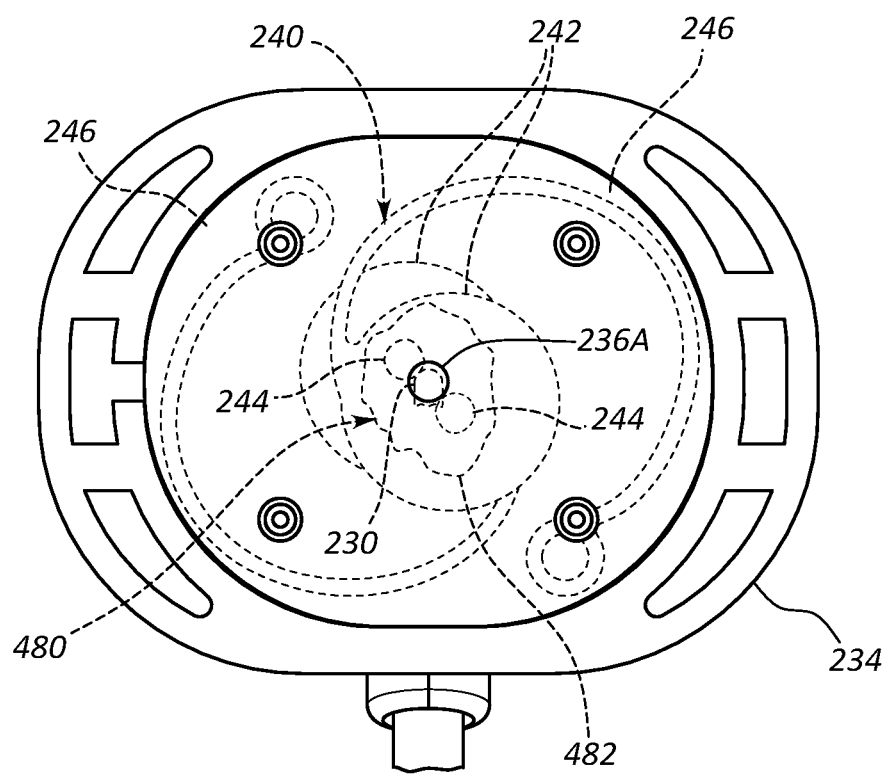
FIG. 20 is a bottom view of a safety needle assembly including a fluid isolation component according to one embodiment.

FIG. 20 depicts details of another possible fluid isolation component for use with the needle assembly 220 (shown in FIGS. 11-12B), or another suitable needle assembly. In particular, a fluid isolation component 480 is disclosed, including an amount of suitable viscous oil 482, such as silicone oil, interposed as a film between the shutters 242. When the needle 230 is retracted from the hole 236A in the needle assembly base 236, which retraction causes the shutters 242 to slide over and cover the hole, the oil 482 produces a fluid impermeable barrier layer between the shutters, thus preventing any fluid/vapor escaping the needle from escaping past the shutters. In other embodiments, other barriers can be employed between the shutters, including a gasket, O-ring, other compliant/elastomeric member, etc.

FIGS. 21A-24 depict various details regarding a fluid isolation component according to yet another embodiment, for use with a safety needle assembly. As will be described, the fluid isolation component in the present embodiment includes a self-sealing pad that prevents unintended leakage of fluids (e.g., liquids, gases) from the needle after use of the needle assembly. The self-sealing pad thus prevents undesired exposure to clinicians of potentially hazardous substances.

Figure 21A:
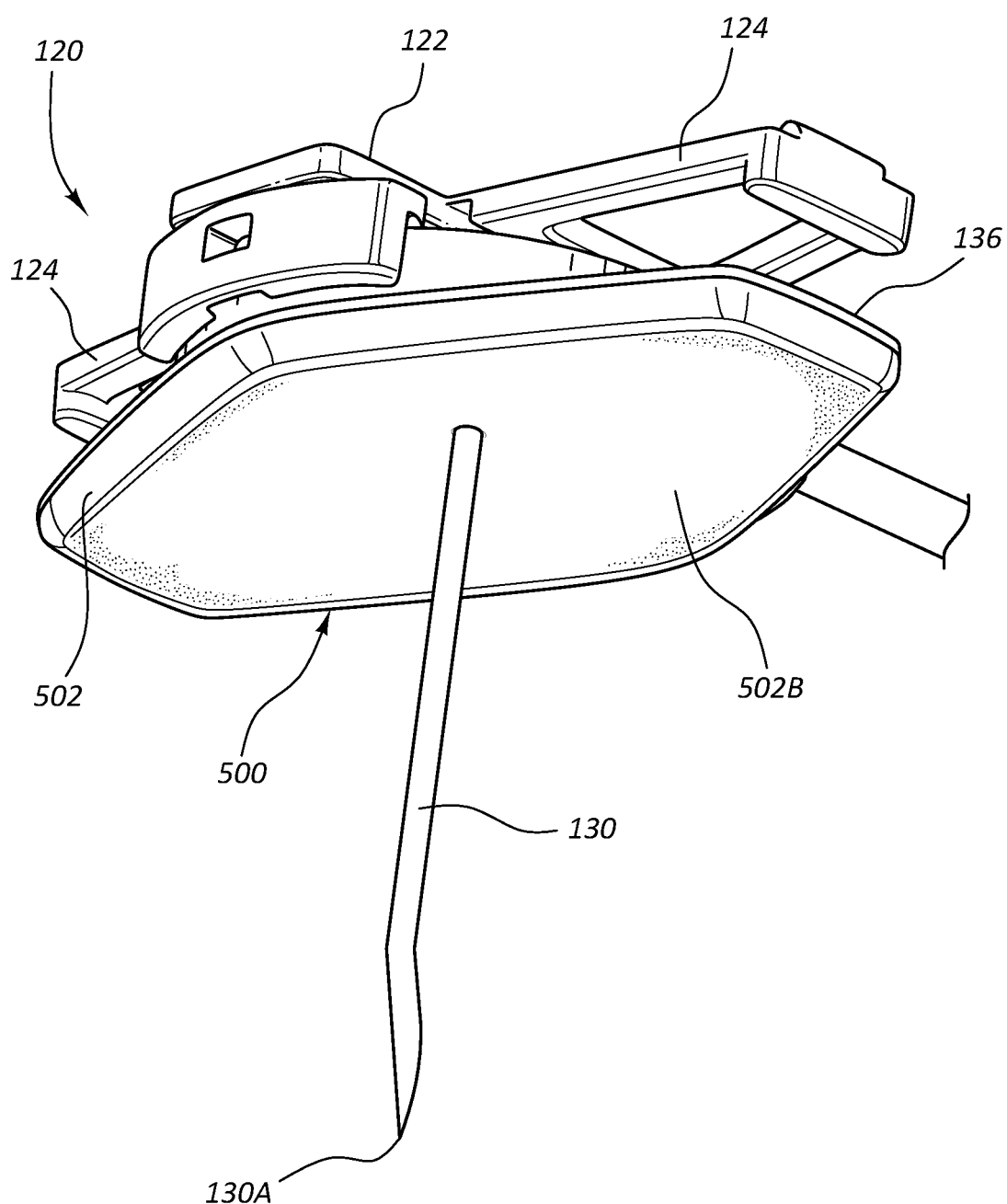
FIGS. 21A and 21B are various views of a needle assembly including a self-sealing pad according to one embodiment.
Figure 21B:
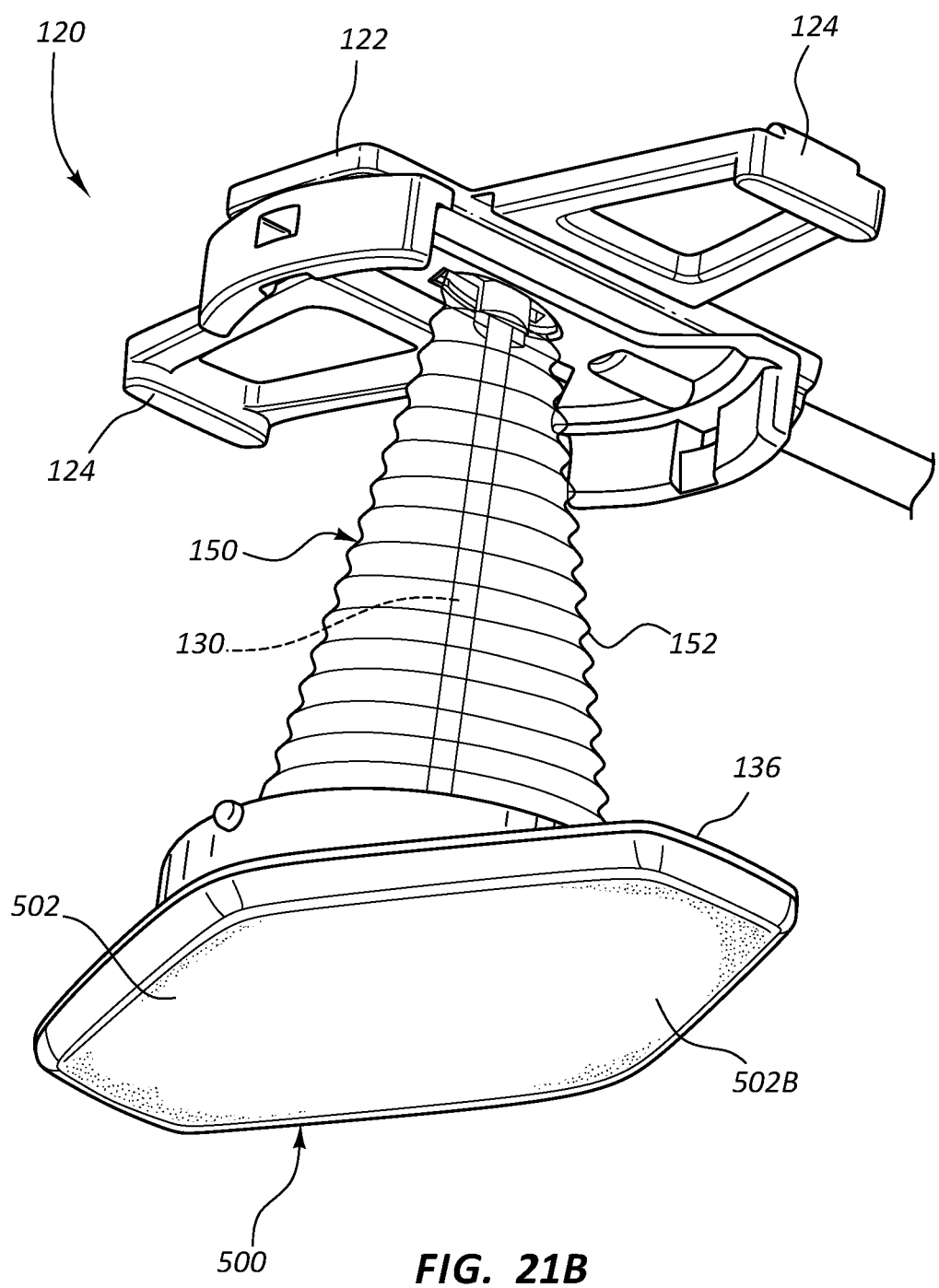

FIGS. 21A and 21B show the needle assembly 120 in similar configuration to that described further above in connection with FIGS. 5-6C. As before, the needle assembly 120 includes a first needle assembly portion, i.e., the handle portion 122, with handles 124 extending therefrom. The hollow needle 130 extends from the handle portion 122 and initially through the safety assembly 134 that is slidably disposed with respect to the needle 130 so as to be axially slidable therewith. The safety assembly 134 includes the base, also referred to herein as a second needle assembly portion or the base portion 136, which houses the needle safety component 140 (FIGS. 8A, 8B) for shielding the distal tip 130A of the needle 130 when use of the needle assembly is complete.

As already described further above, the needle assembly 120 further includes a first fluid isolation component 150 for isolating any fluid or vapor that may unintentionally escape from the needle 130 during use of the needle assembly. Specifically, the first fluid isolation component 150 includes the conically shaped, extensible shroud 152 disposed about the body of the needle 130 and extending between the handle portion 122 and the axially slidable safety assembly 134 of the base portion 136. The shroud 152 forms a hollow cone about the needle 130 and is corrugated with corrugations 154 in a bellows-like manner to enable it to fold up compactly when the safety assembly 134 is undeployed (FIG. 4) and to extend to cover and substantially encompass the needle 30 when the safety assembly 134 is deployed (FIG. 5). As already discussed, in the extended state shown in FIGS. 5 and 6C, the shroud 152 assists in isolating fluids/vapors present on the needle 130 or emitted from the needle distal tip 130A from contact with the clinician.

FIGS. 21A-21B further show a self-sealing pad 500 disposed on a bottom external surface of the base portion 136. The pad 500 includes a self-sealing material that enables the needle 130 to extend therethrough, as seen in FIG. 21A (also referred to as the first needle position), but seals when the needle is retracted back through the pad via separation of the base portion 136 from the handle portion 122, as seen in FIG. 21B (also referred to as the second needle position). In particular, and as shown in FIG. 21B, the full extension of the base portion 136 from the handle portion 122 causes the distal tip 130A of the needle 130 to be drawn through the pad 500 such that the distal tip is shielded within the base portion, in particular, shielded by the needle safety component 140. Because of its self-sealing characteristics, the pad 500 substantially seals the hole through which the needle 130 was disposed during needle assembly use, thus preventing any fluid leakage from the distal opening of the needle 130 to escape the base portion 136, as desired. Note that, though shown and described herein in connection with the needle assembly 120, the self-sealing pad 500 can be included with needle assemblies and infusion sets of a variety of configurations in addition to those discussed herein.

Figure 22A:
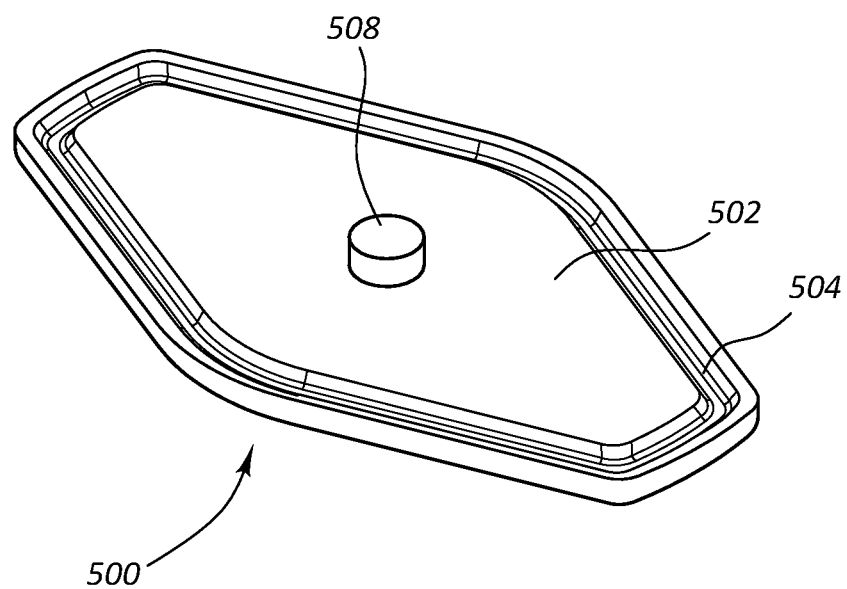
FIGS. 22A and 22B are various views of the self-sealing pad of FIGS. 21A and 21B.
Figure 22B:
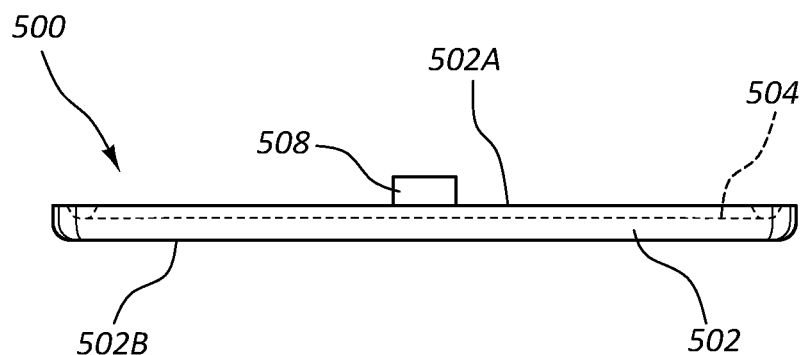

FIGS. 22A and 22B depict various features of the self-sealing pad 500 according to the present embodiment. As shown, the pad 500 includes a body 502 shaped to conform to the shape of the base 136, though in other embodiments the pad could include other shaped configurations. The body 502 defines an upper surface 502A that is configured to mate with the base portion 136 and a bottom surface 502B that serves as a skin-contacting surface for the needle assembly 120.

A groove 504 is defined about the perimeter and configured in the present embodiment to receive therein a corresponding protruded surface 506 defined on a bottom surface of the base portion 136. The receipt of the protruded surface 506 by the groove 504 assists in maintaining engagement of the pad 500 with the base portion 136, in one embodiment. The pad 500 can be affixed to the base portion 136 via a suitable adhesive or by other suitable methods, including mechanical fixation.

In one embodiment, the pad 500 includes silicone, though other self-sealing materials, plastics, and elastomers can be employed. In one embodiment, a liquid silicone rubber ("LSR") that is injection molded then cured is employed to form the pad 500. So configured, the skin-contacting bottom surface 502B of the pad 500 provides a compliant surface to rest against the skin of the patient during use of the needle assembly 120.

Figure 23B:
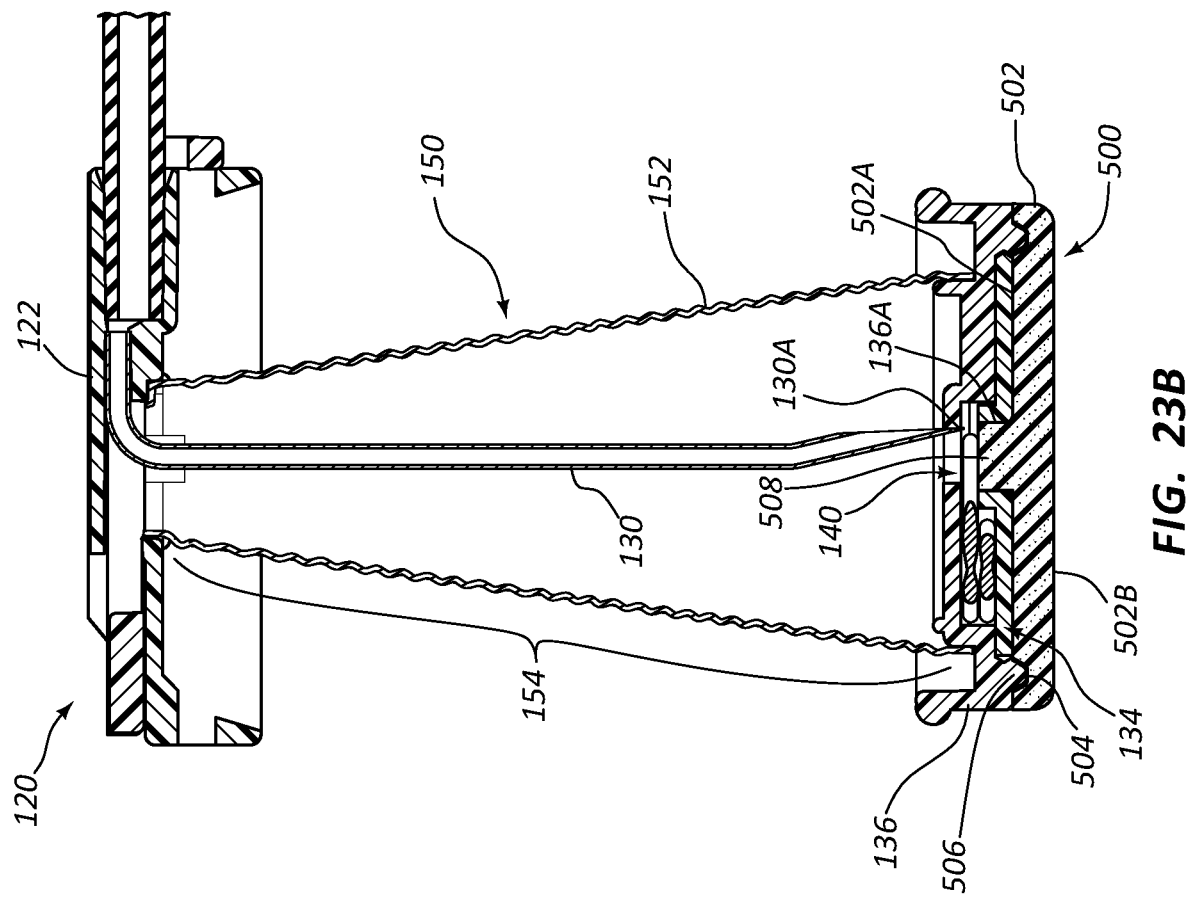
FIGS. 23A and 23B are various views of the needle assembly of FIGS. 21A and 21B.
Figure 23A:
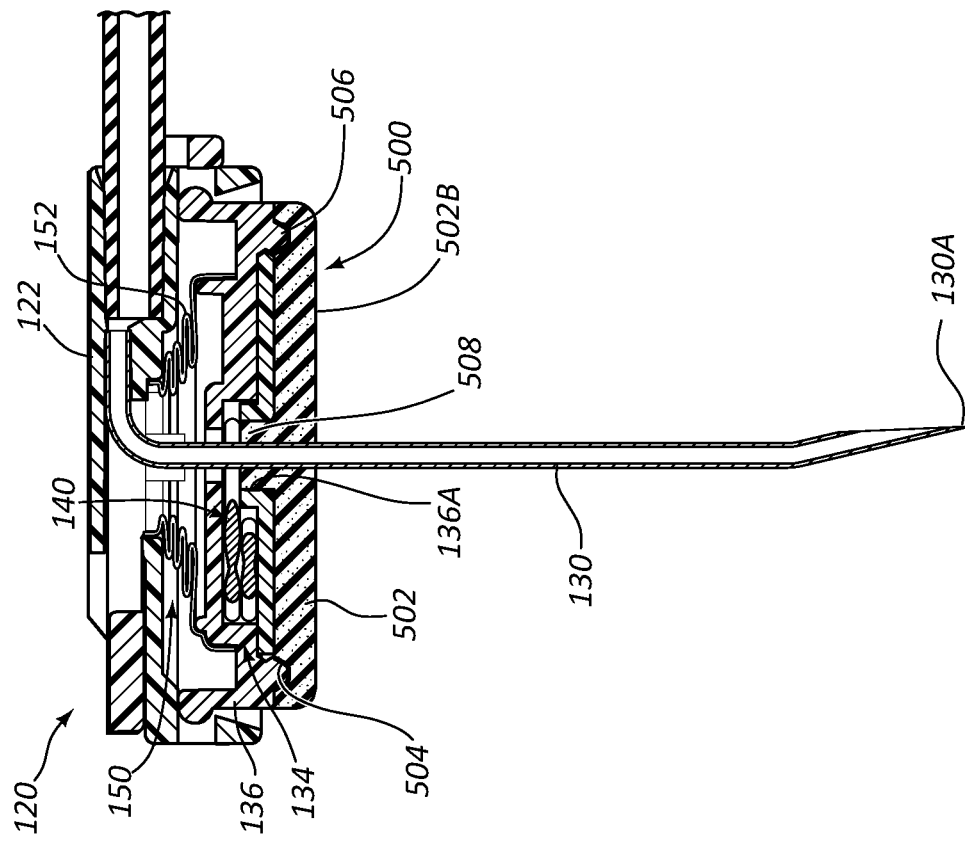

The pad body 502 further defines a centrally disposed raised portion 508, best seen in FIGS. 22A and 22B, which is shaped so as to compressively fit within an opening 136A that is defined in the base portion 136. As shown in FIGS. 23A and 23B, the raised portion 508 of the pad 500 is disposed within the opening 136A and is partially maintained in place via a compressive fit with the opening. So configured, the raised portion 508 acts as a septum to provide a robust fluid barrier when the needle 130 is withdrawn therethrough and shielded by the safety assembly 134, which occurs when the base portion 136 is selectively extended from the handle portion 122, as shown in FIG. 23B. Indeed, compression of the raised portion 508 by the opening 136A assists in the self-sealing characteristics of the pad 500 when the needle 130 is retracted, in one embodiment. Thus, the self-sealing pad 500 serves as a second fluid isolation component, together with the shroud 152, for preventing fluid/vapor escape from the needle assembly. The shape and size of both the raised portion and the opening can vary from what is shown and described herein. In the present embodiment, the distal tip 130A of the needle 130 fully withdraws from the raised portion 508, though in other embodiments the distal tip can remain in the raised portion 508 after shielding thereof by the safety assembly. An example of the latter configuration would include the distal tip of the needle retracting fully from the lower surface 502B of the pad body while still residing within raised portion 508 of the pad.

Figure 24:
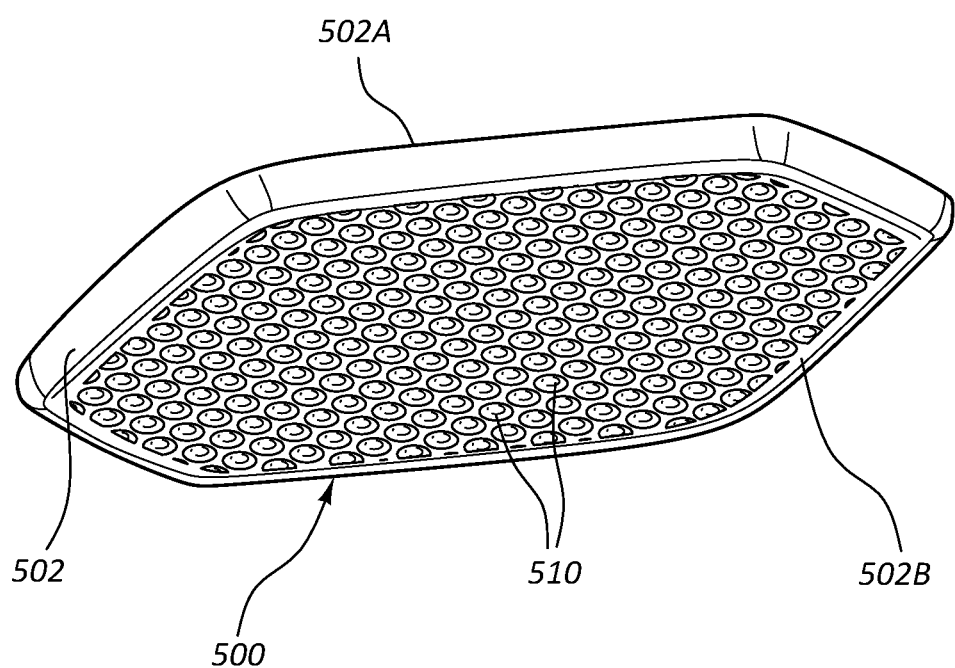
FIG. 24 is a perspective view of a self-sealing pad according to one embodiment.

The self-sealing pad can be configured in other ways. For instance, FIG. 24 shows the bottom surface 502B as including a plurality of texture features 510 for increasing patient comfort while the needle assembly 120 is disposed on the skin of the patient. Also, in one embodiment, it is appreciated that the self-sealing pad can be treated so as to offer antimicrobial/antibacterial properties. Further, in one embodiment, the bottom surface of the self-sealing pad can include an adhesive material to enable the pad to act as a securement device in maintaining the infusion set in place at a desired position on the patient's skin during use of the needle assembly. It is further appreciated that the needle assembly and accompanying infusion set can include one of many possible shapes, sizes, and configurations in addition to those shown and discussed herein.

FIGS. 25-41 depict various features of an interface pad or other structure for inclusion on a medical device, such as a needle assembly or catheter assembly, so as to provide an interface between the medical device and the skin surface of the patient after the device has been percutaneously inserted into the patient via an insertion site. Particularly, the interface pad is positioned on the medical device so as to rest against the insertion site on the patient's skin once the device has been inserted into the patient.

Further, the interface pad includes one or more components that provide desirable effects at the insertion site. In accordance with one embodiment, for instance, an antimicrobial agent and/or haemostatic agent are impregnated into the interface pad so as to provide antimicrobial and/or haemostatic properties to the insertion site via contact of the agents from the pad with the insertion site. In this way, infection, undesired bleeding, etc. can be controlled via use of the interface pad. In addition to the above-mentioned agents, other substances can be included in the interface pad to impart other desirable characteristics, such as antithrombogenic agents, for instance.

Figure 25:
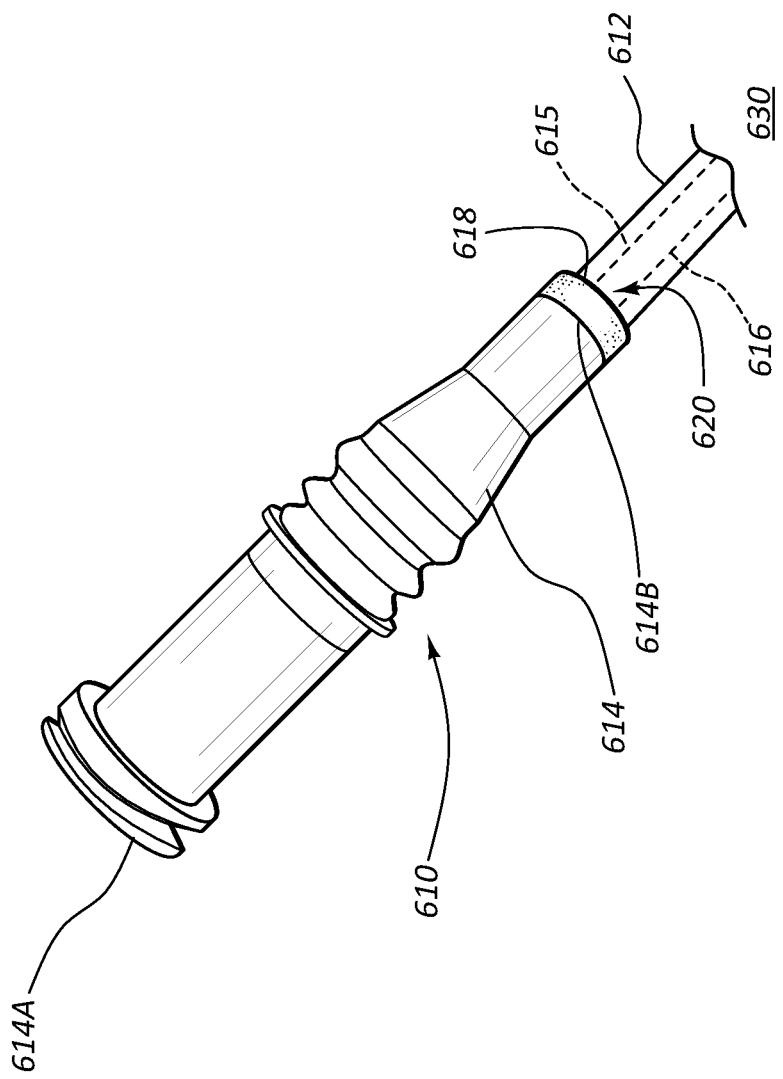
FIG. 25 is a perspective view of a plurality of catheters including an interface pad according to one embodiment.

Reference is first made to FIG. 25, which shows a catheter assembly ("catheter"), generally designated at 610, according to one embodiment. As shown, the catheter includes a hub 614 to which is connected at a distal end thereof an elongate, hollow catheter tube 612 defining a lumen 615. The catheter 610 includes a needle 616 inserted through the hub 614 so as to extend into the lumen 615 of the catheter tube 612. The needle 616 is used to assist with percutaneous insertion of the catheter tube 612 into the body of the patient via an insertion site 618 (FIG. 26B). Once the catheter 10 is percutaneously inserted within the patient, the hub 614 rests above a skin surface 630 of the patient, as seen in FIG. 26B. Note that, though shown here as defining a single lumen 615, the catheter tube 612 can define more than one lumen, such as two, three, or more lumens, in one embodiment. Also note that, though describing a catheter assembly herein, the present disclosure contemplates that other types of catheters including PICCs, PIVs, midline and intermediate dwell catheters, Foley and balloon catheters, epidural catheters, feeding catheters, drainage catheters, infusion sets, needle assemblies, and other medical devices can benefit from the teachings herein. The discussion to follow, therefore, is not intended to be limiting of the present disclosure.

FIG. 1 further shows an interface pad ("pad") 620, configured according to one embodiment, attached to catheter 610. As shown, the pad 620 is interposed between the distal end 614B of the hub 614 and the skin surface 630 so as to rest adjacent to and substantially cover the insertion site 618 (FIG. 26B) when the catheter 610 is percutaneously inserted into the patient.

Figure 26A:
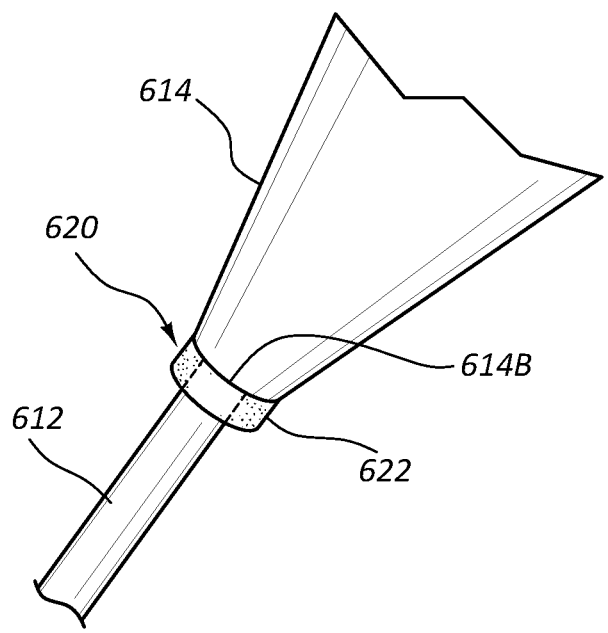
FIGS. 26A and 26B are side views of a catheter including an interface pad according to one embodiment.
Figure 26B:
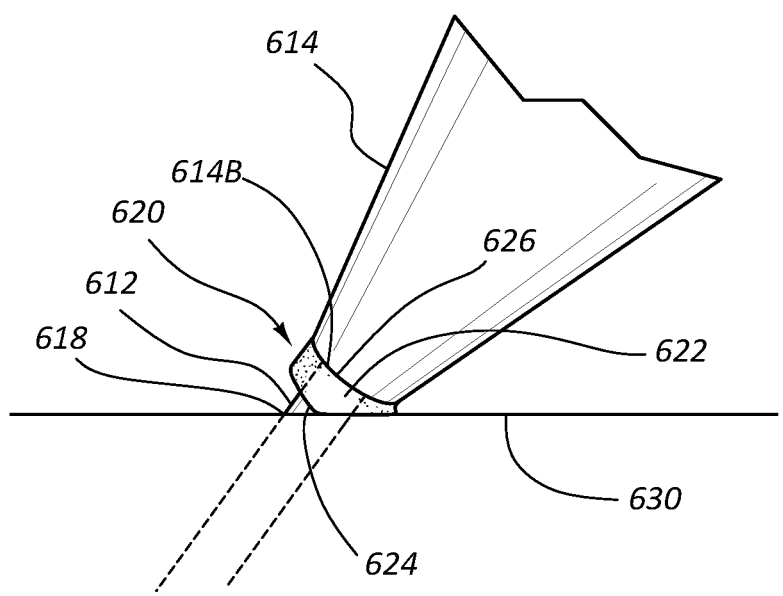

FIGS. 26A and 26B depict further details of the pad 620, according to one embodiment. As shown in FIG. 26A, the pad 620 includes a compliant body 622 that can be permanently or temporarily attached to the distal end 614B of the hub 14, though other attachment locations to the medical device are possible. As will be seen, the pad body 622 can be configured in any one of a variety of shapes, sizes, etc. In the present embodiment, the pad body 622 defines a disk-shaped configuration and is adhered by an adhering surface 626 to the hub distal end 614B via a biocompatible adhesive, though other modes of attachment, including chemical, mechanical, frictional, etc., can be employed. Example adhesives in one embodiment include cyanoacrylate, UV- or heat-cured adhesives, epoxies, solvent bonding adhesives, acrylic-based, silicone-based, rubber-based, urethane-based, and hydrocolloid adhesives. In other embodiments, the interface pad is not compliant or compressible, but substantially rigid. For instance, an incompressible polymeric material that includes the ability to leach one or more agents (discussed below) for treating the insertion site 618 could be employed for the pad body 622. These and other variations of the pad are therefore contemplated.

Though a variety of suitable, biocompatible materials can be employed, in the present embodiment the pad body 622 includes a compressible polyurethane foam that is capable of absorbing and holding agents (discussed below) that may be impregnated into the foam. Manufacture of the pad body 622 from a compressible/compliant material enables the pad to conform to the skin surface 630 about the insertion site 618 when the catheter tube 612 is percutaneously inserted into the patient's body. As such, one or more portions of an outer surface of the pad body 622 serve as a deformable contact surface 624 so as to provide a cushioning interface between the catheter hub 614 and the patient skin 630, as seen in FIGS. 25 and 26B. The cushioning effect of the pad body 622 serves to increase patient comfort when the catheter is disposed in the patient.

Specifically, in one embodiment, the pad body 622 includes an aromatic polyether polyurethane foam, including a TDI or MDI hard segment and a PTMEG (polytetramethylene ether glycol) soft segment. Other suitable polymer-based foam materials as well as non-foam materials can also be employed for the pad body 622. In one embodiment, desired characteristics for a foam material used for the pad body 622 include hydrophilicity (absorptive), a suitably large surface area to volume ratio for the foam, and a suitable diffusion coefficient. These desired characteristics are useful when one or more agents for treating the insertion site 618 are included with the pad body 622, as will be described below. In addition, other materials can be employed, including polyethylene, woven and non-woven fabrics including felt and cotton, gels, and hydrogels. In one embodiment, the pad body includes a compressed foam that expands in size upon activation with blood or other body fluid/liquid. In such an embodiment, a dry antimicrobial or other agent can be included with the pad body.

As mentioned above, the pad 620 is configured in one embodiment to include one or more agents for treating the insertion site 618 of the catheter 610 or other medical device. In one embodiment, a liquid solution (or other suitable medium) including an antimicrobial agent, a haemostatic agent, an antithrombogenic agent, or other substance to protect, heal, or otherwise assist care of the insertion site 618 is included in the pad body 622. In the present embodiment, the pad 620 includes a liquid antimicrobial agent that is infused during manufacture into the polyurethane foam material from which the pad body 622 is formed. Once the catheter 610 has been placed percutaneously into the patient and the pad 620 is positioned adjacent the patient skin 630 as shown in FIG. 26B, the antimicrobial agent previously infused into the foam pad body 622 contacts the insertion site 618 via the contact surface 624 of the pad body 622 and provides antimicrobial effect, thus desirably protecting the insertion site from infection.

In the present embodiment, a liquid haemostatic agent is also infused during manufacture into the polyurethane foam material from which the pad body 622 is formed. When the pad 620 is positioned adjacent to the insertion site 618 as just described and as shown in FIG. 26B, the haemostatic agent previously infused into the foam pad body 622 contacts the insertion site via the contact surface 624 of the pad body 622 and provides haemostatic effect, thus desirably preventing excessive bleeding from the insertion site. Note that the pad body 622 in one embodiment is absorptive so as to take up effusion of blood and other fluids from the insertion site 618, in one embodiment.

In one embodiment, the antimicrobial agent can include silver, copper (and other biocompatible antimicrobial metals, silver sulfadiazine, chlorhexidine, chlorhexidine gluconate ("CHG"), chlorhexidine acetate ("CHA"), other suitable chlorhexidine-based antimicrobial agents, isopropyl alcohol ("IPA"), etc. In one embodiment, the haemostatic agent includes microdispersed oxidized cellulose, other suitable hydrocolloids, etc. In one example embodiment, a solution included in the pad 620 includes an antimicrobial agent of about 11% by weight CHG and a haemostatic agent of about 8% by weight microdispersed oxidized cellulose, though these percentages can vary in other formulations. For example, in one embodiment, the amount of CHG by weight in the solution can vary between about 11% to about 25%, though other ranges are possible, depending on various factors, including the type of pad material employed, processing parameters during pad manufacture, etc. In another embodiment, it is appreciated that the antimicrobial agent, haemostatic agent, or other agent included with the interface pad can be in a dry state, such as a solid or powder, for instance.

In yet another embodiment, the foam itself of the interface pad body can be configured to impart haemostatic properties and therefore act as the haemostatic agent. Indeed, in one embodiment, negatively charged sulfonate groups can be incorporated into the soft segment (e.g., polytetramethylene ether glycol) of a polyurethane foam so as to impart haemostatic properties thereto. In such a case, no other haemostatic agent need be added, though an additional agent could be, if desired.

Further details regarding antimicrobial and haemostatic agents that may be used according to one embodiment are found in U.S. Patent Publication No. 2013/0110025, filed Jul. 4, 2011, and titled "Dressing Device for Use with a Cannula or a Catheter," which is incorporated herein by reference in its entirety. In yet another embodiment, the antimicrobial agent (such as CHG) is incorporated into the material from which the interface pad body is composed, such as a solvent acrylic adhesive. Details regarding such a configuration can be found in U.S. Pat. No. 9,346,981, issued May 24, 2016, and titled "Chlorhexidine Gluconate Containing Solvent Adhesive," which is incorporated herein by reference in its entirety. In yet another embodiment, an antimicrobial silicone adhesive, such as that produced by Covalon Technologies Ltd., Mississauga, Ontario, can be used to form the interface pad body and antimicrobial agent. In yet another embodiment, a hydrogel or other hydrocolloid in which the antimicrobial and/or haemostatic agent is incorporated can be used to form the interface pad body.

It is appreciated that one or more of a variety of agents can be included with the pad 620 to render to it desirable qualities or characteristics. For instance, the pad body can include an antithrombotic agent. Note also that in one embodiment, the antimicrobial/haemostatic agent can be incident on the insertion site 618 via liquid dispersion.

It is further appreciated that, in one embodiment, the afore-mentioned desirable qualities of the pad body material—including hydrophilicity/absorptiveness and sufficiently large surface area to volume ratio—assist in enabling the microdispersed oxidized cellulose haemostatic agent to be present in the pad body and to contact and interact with the insertion site, as desired. Additionally, in one embodiment the afore-mentioned desirable quality of suitable diffusion coefficient for the pad body material assists in enabling the antimicrobial agent to contact and interact with the insertion site so as to provide desired antimicrobial properties.

In addition to agent-based protection, the pad 620 also physically protects the insertion site 618 by providing a physical barrier and cushion for the insertion site, which provide patient comfort when the catheter 610 or other medical device is resting against the skin, as seen in FIG. 26B. As such, it is appreciated that the pad can be manufactured using one or more of a variety of materials and in a variety of shapes, sizes, and configurations. In one embodiment, as mentioned, the pad body includes a gel or hydrogel material.

In light of the above, FIGS. 27A-29B depict various examples of possible shapes for the body 622 of the pad 620, according to example embodiments. FIGS. 27A and 27B show the pad body 622 defining a central hole 632 for passage therethrough of the needle 616 (FIG. 25), similar to the pad configuration of FIGS. 25-26B. In one embodiment, the thickness of the pad body 622 of FIGS. 27A and 27B is about 0.0625 inch, though other thicknesses are possible. Generally, the thickness of the pad body should be such that sufficient absorption of the antimicrobial and/or haemostatic agents is possible, while not becoming too thick so as to decrease the useful length of the catheter tube.

FIGS. 28A and 28B show a rectangular pad body 622, wherein a hole therethrough for passage of the catheter 610 may be made by piercing the pad body with the needle 616 during the catheter insertion procedure or during manufacture.

FIGS. 29A and 29B show a disk-like pad body 622 with a slit 634 defined from an edge of the disk to the center thereof to enable its attachment to or removal from the catheter 610. As such, it is appreciated that the pad 620 can be permanently or removably attached to the catheter hub 614, such as is seen in FIG. 26A or in another suitable location, as appreciated by one skilled in the art. These and other suitable pad body shapes and configurations are therefore contemplated.

Figure 30:
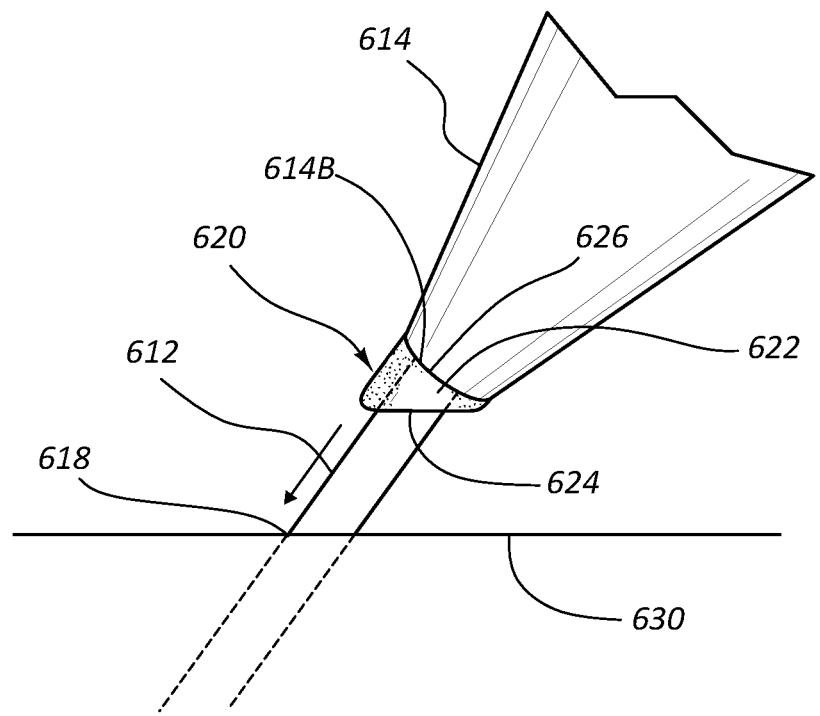
FIG. 30 is a side view of a catheter including an interface pad according to one embodiment.

FIG. 30 depicts details of another possible shape configuration for the pad 620, wherein the pad body 622 defines an angular shape, from the perspective shown in FIG. 30, such that the contact surface 624 thereof is substantially parallel to the skin surface 30 when the catheter tube 12 is percutaneously inserted into the patient, as shown. Such a configuration distributes the contact load of the pad 620 with the patient skin 630 across the relatively parallel and flat contact surface 624, thus diminishing contact force at any given point on the contact surface, which increases patient comfort, and increases the relative surface area of the contact surface about the insertion site to enhance the effectiveness of the antimicrobial and/or haemostatic agents.

FIG. 33 depicts yet another possible pad configuration to maximize skin contact, wherein the pad body 622 approximately defines a parallelogram shape, from the perspective shown in FIG. 33, which also desirably produces a relatively parallel pad contact surface with respect to the skin surface 30. FIG. 33 further shows that, in one embodiment, the distal end 614B of the hub 614 can be angled to be substantially parallel with the skin surface 630 after percutaneous catheter insertion is completed.

Figure 32:
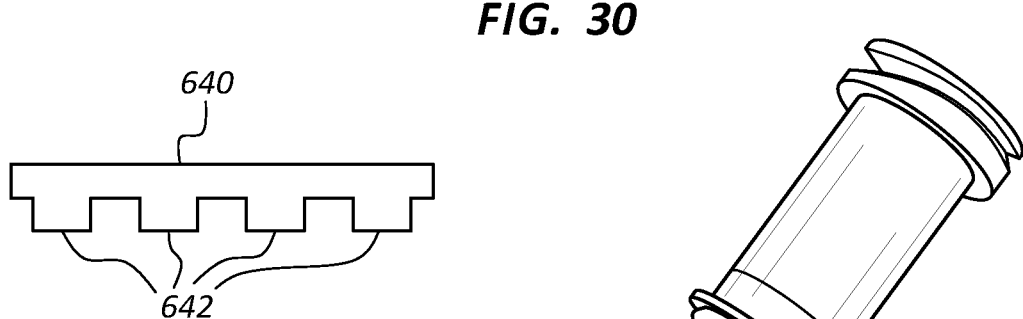
FIG. 32 is a side view of a strip of antimicrobial foam for use as an interface pad according to one embodiment.
Figure 31:
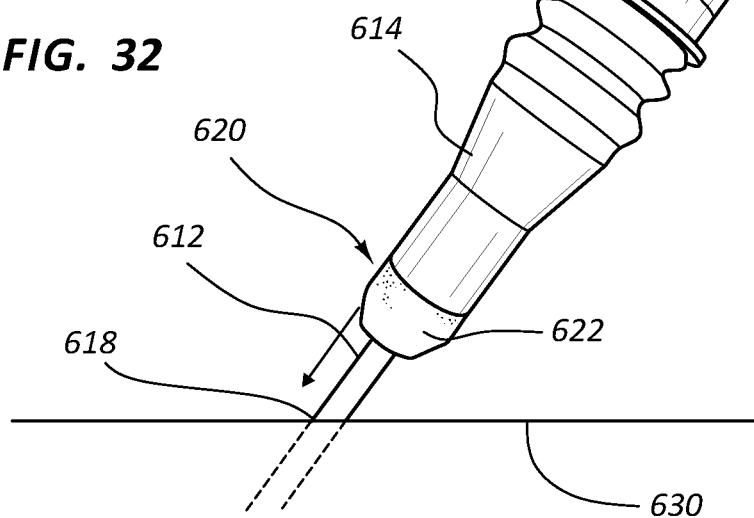
FIG. 31 is a side view of a catheter including an interface pad according to one embodiment.

FIGS. 31 and 32 depict details of another embodiment of the interface pad 620, wherein the pad is produced from a foam strip 640 that includes a pattern of spaced-apart teeth 642, as seen in FIG. 32. During pad manufacture, the foam strip 640 is rolled about the proximal end 612A of the catheter tube 612 and secured in its rolled configuration (via adhesive or the like) to define the interface pad 620 shown in FIG. 31. The toothed pattern of the foam strip 640 imparts an angled configuration for the pad body, which assists in providing a contact surface for the pad that is relatively more parallel to the skin surface 630 of the patient, as has been discussed. Note that the teeth 642 shown here is just one of a variety of different patterns that can be included in the foam strip 640 from which the pad 620 can be manufactured.

FIGS. 34 and 35 depict details of an interface pad 720 according to one embodiment. As shown, the pad 720 includes a body 722 that defines a cavity 726 so as to form a cap-shaped configuration. So configured, the cavity 726 of the pad body 722 receives a portion of the catheter hub 614 therein such that the distal end of the hub is covered, or capped, by the pad. The pad 720 can be temporarily or permanently secured to the hub 614 along an adhering surface 726 via adhesive or other suitable fixation mode. The pad 720 defines an outer contact surface 724 for deformable contact with the skin surface 630. As before, the pad 720 can include an antimicrobial, haemostatic, or other suitable agent for protecting/healing the insertion site 618 of the catheter 610 and for destroying microbes that may otherwise be present on portions of the catheter tube 612 in contact with the interface pad. Also, in one embodiment, the pad 720 can be scored or include a slit so as to make it readily removable from the catheter hub or other medical device to which it is at least temporarily attached.

Figure 36A:
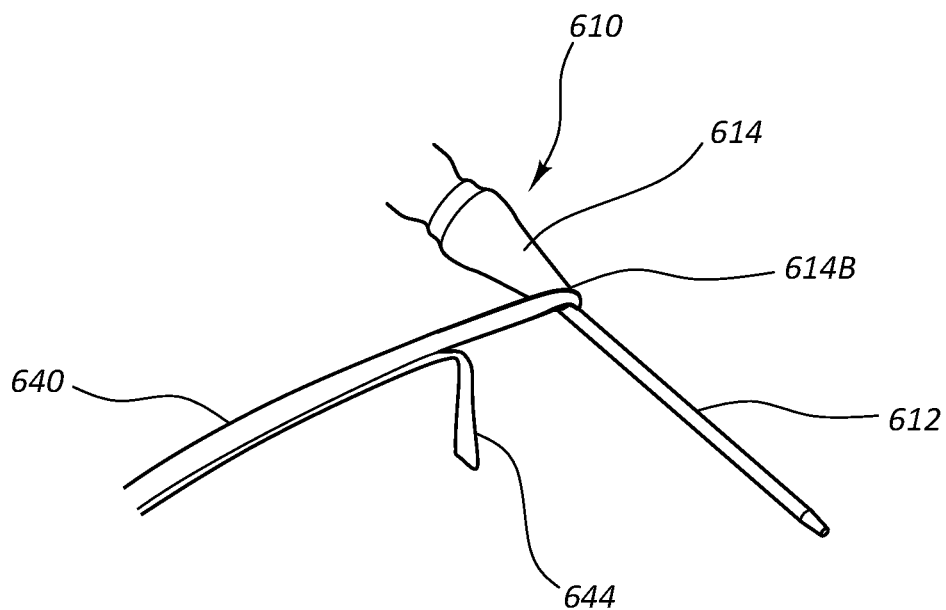
FIGS. 36A and 36B are various views depicting one method for forming an interface pad according to one embodiment.
Figure 36B:
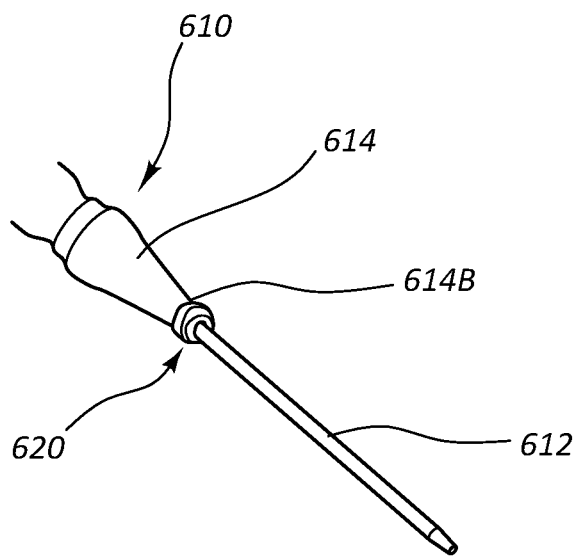

FIGS. 36A and 36B depict details of the interface pad 620 according to one embodiment, wherein the pad is produced from a foam strip, such as the foam strip 640 shown in FIG. 36A. As shown in FIG. 36A, during pad manufacture, the foam strip 640 is rolled about the catheter tube 612. The foam strip 640 can include a liner 644 that is peeled away during rolling such that an adhesive under the liner adheres the pad to the catheter tube 612 and/or hub 614. Once the foam strip 640 has fully encircled the catheter tube 612/hub 614, it can be cut to define the pad 620 shown in FIG. 36B. These and other pad manufacturing methods are therefore contemplated. The foam strip 640 can include one of a variety of lengths, thicknesses, compositions, and other configurations.

Figure 37:
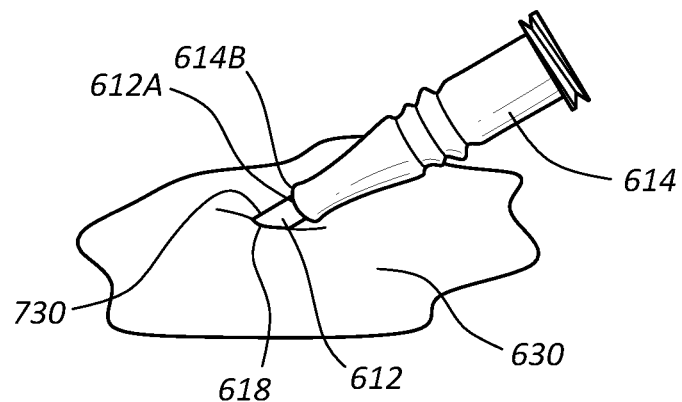
FIG. 37 is a side view of a catheter including an antimicrobial interface according to one embodiment.

FIG. 37 shows yet another embodiment for providing an antimicrobial/haemostatic interface for the catheter 610, wherein a proximal portion of the catheter tube 612 adjacent the proximal end 612A thereof is coated to provide a coated portion 730 that includes an antimicrobial, haemostatic, and/or other suitable agent for protecting and/or healing the insertion site of the catheter 610 through the skin 630 of the patient. The amount of the proximal portion of the catheter tube that is coated to form the coated portion 230 can vary according to need, catheter size, amount of the catheter to remain outside the patient body, etc., but in one embodiment, the coated portion 730 extends distally from about one to about five millimeters from the distal end 614B of the hub 614.

Figure 38:
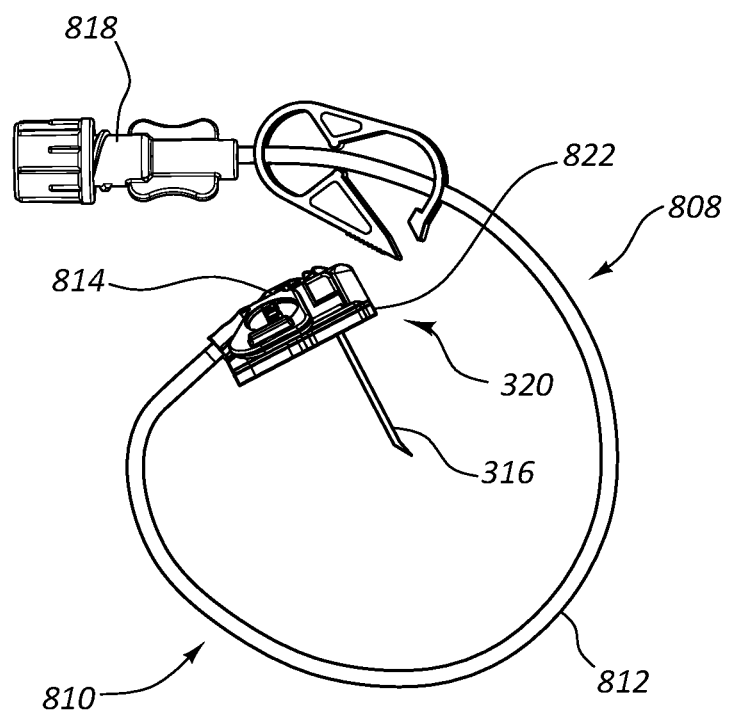
FIG. 38 is a perspective view of an infusion set including an interface pad according to one embodiment.
Figure 39B:
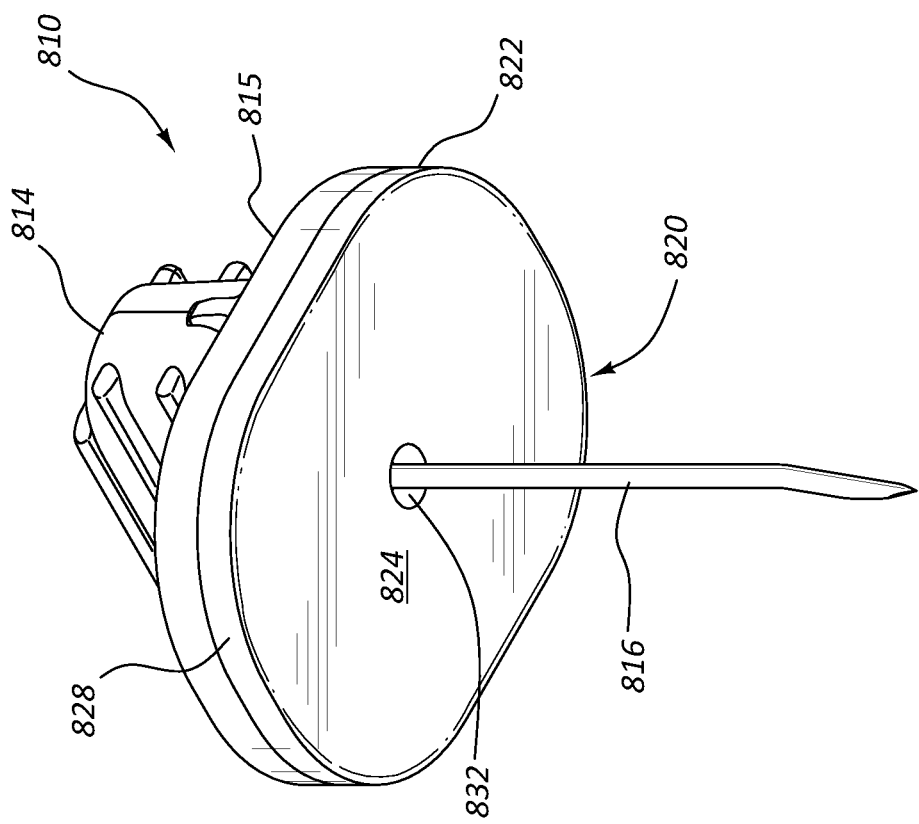
FIGS. 39A-39D are various views of portions of the infusion set of FIG. 38.
Figure 39A:
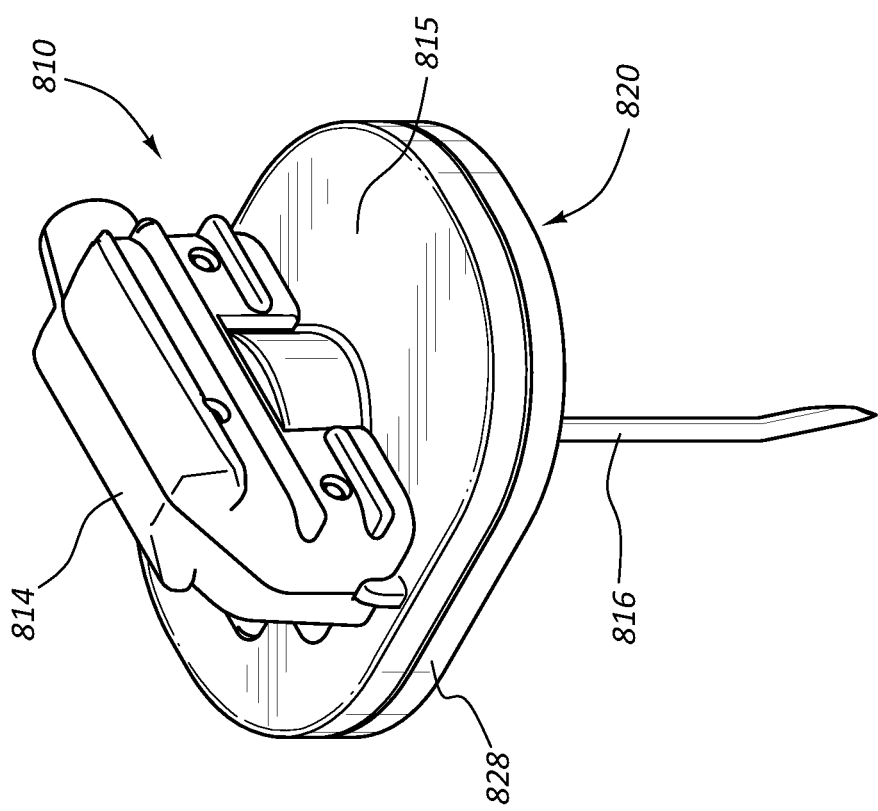
Figure 39D:
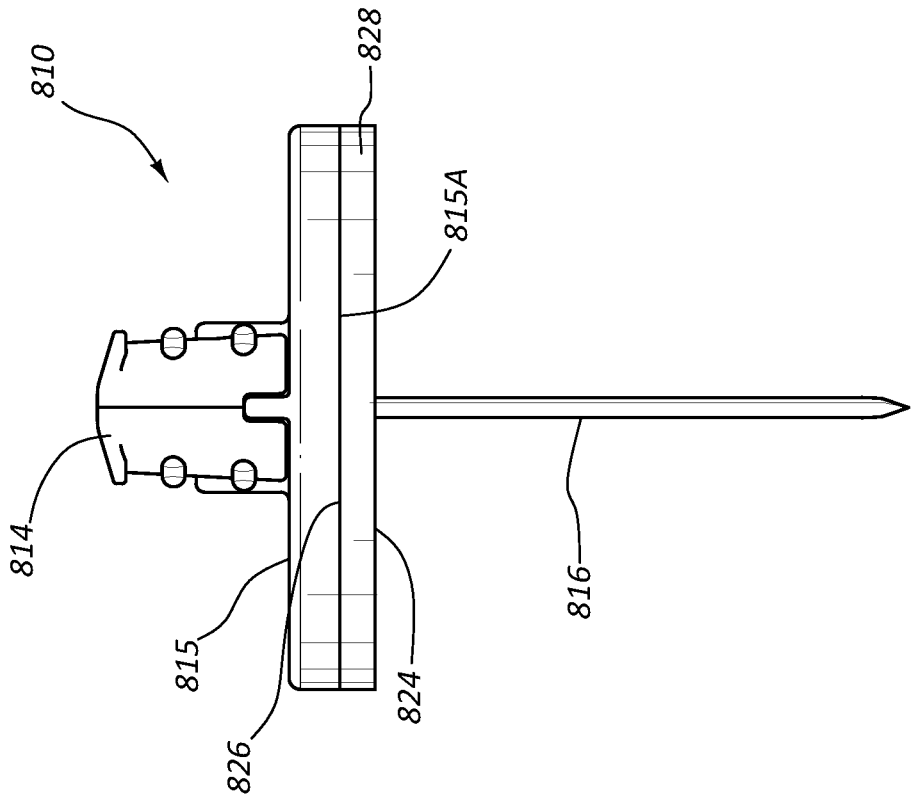
Figure 39C:
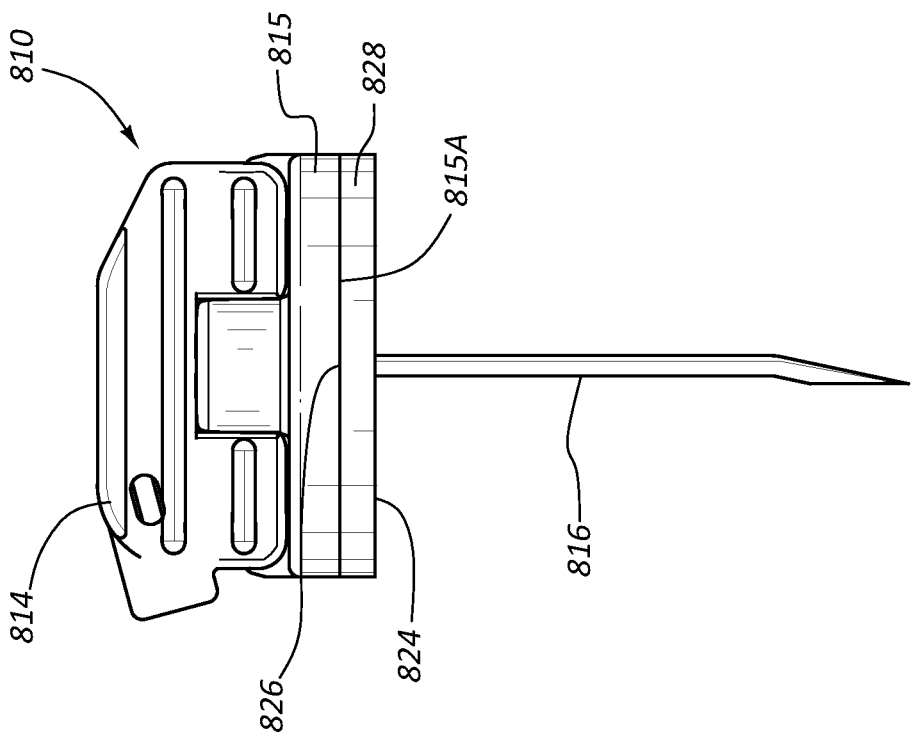

FIGS. 38-39D depict various details of an interface pad for use with yet another type of percutaneous device, according to example embodiments. In particular, FIGS. 38-39D show a safety needle infusion set ("infusion set") 808, typically used to provide percutaneous access to a subcutaneously implanted access port. As shown, the infusion set 808 includes a needle assembly 810 from which extends tubing 812. The tubing 812 is operably connected with a needle hub 814 of the needle assembly 810 so as to be in fluid communication with a needle 816 that extends from the needle hub. The needle hub 814 includes an extensible base 815 that in turn defines a bottom surface 815A. The base is included as part of a needle safety component to prevent needle sticks to the user by the distal tip of the needle, in one embodiment. A connector 818 is included on the opposite end of the tubing 812. As mentioned, the needle 816 is configured to percutaneously pierce the patient's skin via an insertion site so as to access a subcutaneously implanted access port.

In accordance with one embodiment, the needle assembly 810 includes an interface pad 820 included on the bottom surface 815A of the needle hub base 815. As seen in FIGS. 39A-39D, the interface pad includes a body 822 and a hole 832 through which the needle 816 extends. The composition of the pad body 822 and the antimicrobial/haemostatic agents it contains is similar to what has been described in the embodiments above.

The body 822 of the interface pad 820 in the present embodiment defines a perimeter 828 that is shaped to correspond to the perimeter shape of the needle hub base 815. The interface pad body 822 further includes an adhering surface 826 where the pad body attaches to the bottom surface 815A of the needle hub base 815, and a contact surface 824. In the present embodiment, the adhering surface 826 of the pad body 822 is permanently attached to the bottom surface 815A of the needle hub base 815 via a suitable adhesive or other mode as discussed herein. In another embodiment, the pad body 822 is removably attached. The contact surface 824 rests against the skin when the infusion set needle 816 is percutaneously disposed within the patient. As has been described, this enables the antimicrobial/haemostatic agents included with the interface pad 820 to be in contact with and protect the needle insertion site.

FIGS. 40A-40E shows an infusion set 908 and interface pad 920 according to another embodiment. As with the previous embodiment, a safety needle infusion set ("infusion set") 908 is shown and includes a needle assembly 910 from which extends tubing 912. The tubing 912 is operably connected with a needle hub 914 of the needle assembly 910 so as to be in fluid communication with a needle 916 that extends from the needle hub. The needle hub 914 includes an extensible base 915 that in turn defines a bottom surface 915A. The needle hub 914 further includes a pair of wings 917 for grasping the needle assembly 910. The base 915 includes a pair of extensions 919 to assist with using the infusion set 908. Note that the particular shape and configuration of the needle assembly can vary from what is shown and described herein. One or more connectors 918 are included on the opposite end of the tubing 912. As mentioned, the needle 916 is configured to percutaneously pierce the patient's skin via an insertion site so as to access a subcutaneously implanted access port.

In accordance with one embodiment, the needle assembly 910 includes an interface pad 920 included on the bottom surface 915A of the needle hub base 915. As seen in FIGS. 40A-40E, the interface pad includes a body 922 and a hole 932 through which the needle 916 extends. The composition of the pad body 822 and the antimicrobial/haemostatic agents it contains is similar to what has been described in the embodiments above.

The body 922 of the interface pad 920 in the present embodiment defines a perimeter 928 that is shaped to correspond to the perimeter shape of the needle hub base 915, including the shape of the extensions 919 of the needle hub base. The interface pad body 922 further includes an adhering surface 926 where the pad body attaches to the bottom surface 915A of the needle hub base 915, and a contact surface 924. In the present embodiment, the adhering surface 926 of the pad body 922 is permanently attached to the bottom surface 915A of the needle hub base 915 via a suitable adhesive or other mode as discussed herein. In another embodiment, the pad body 922 is removably attached.

Figure 41:
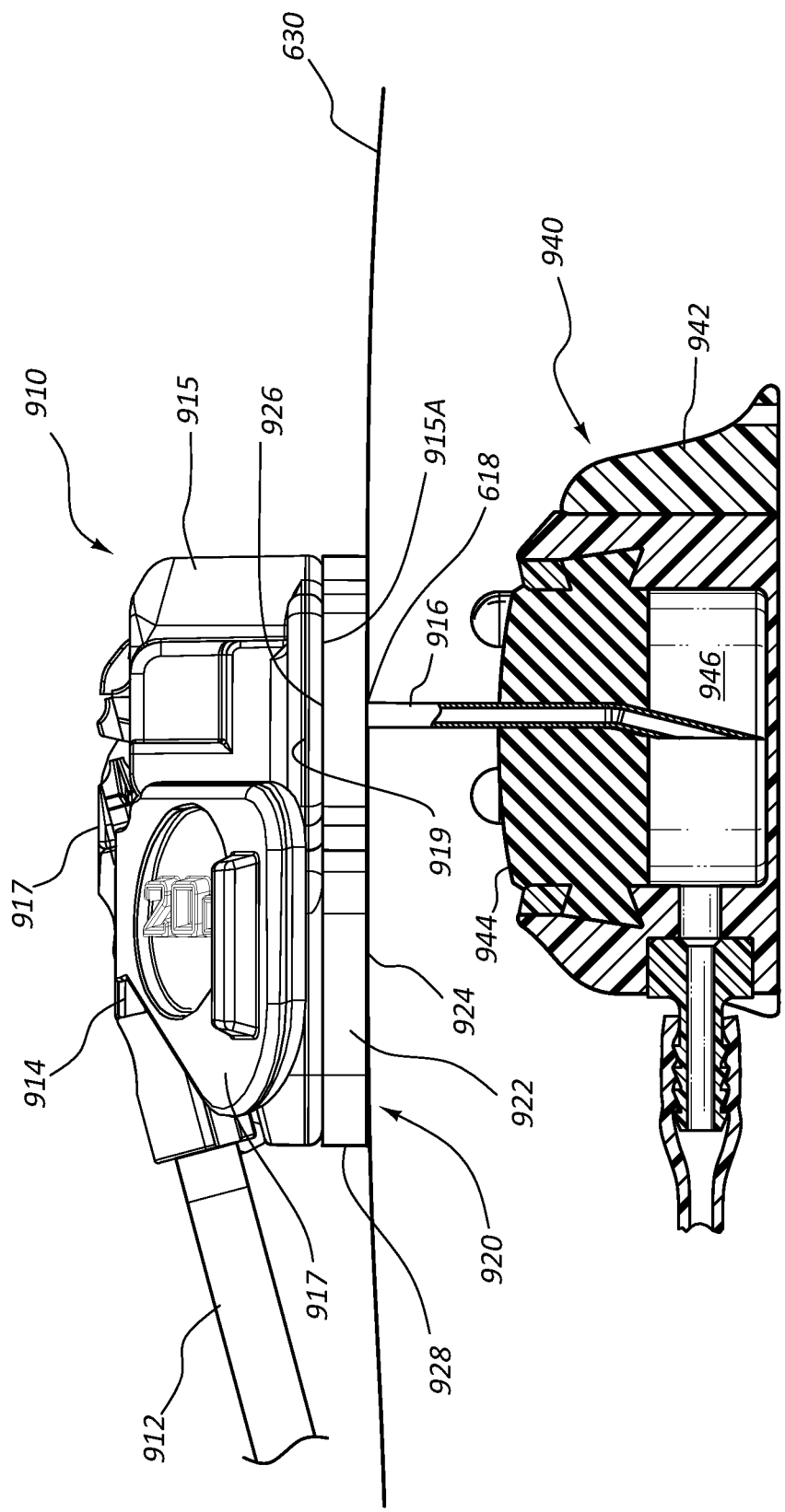
FIG. 41 is a partial cross-sectional side view of the infusion set of FIGS. 40A-40E operably connected to an implanted access port according to one embodiment.

As seen in FIG. 41, the needle assembly 910 of the infusion set 908 can be employed to access a subcutaneously implanted access port 940. As shown, the access port 940 includes a body 942 and a septum 944 that cooperate to define a reservoir 946.

As has been described, the contact surface 924 of the pad 920 of the infusion set needle assembly 910 rests against the skin 630 when the needle 916 of the needle assembly 910 is percutaneously disposed within the patient, such as in accessing the access port 940 shown in FIG. 41. This enables the antimicrobial/haemostatic agents included with the interface pad 920 to be in contact with and treat/protect the needle insertion site 618.

Figure 40A:
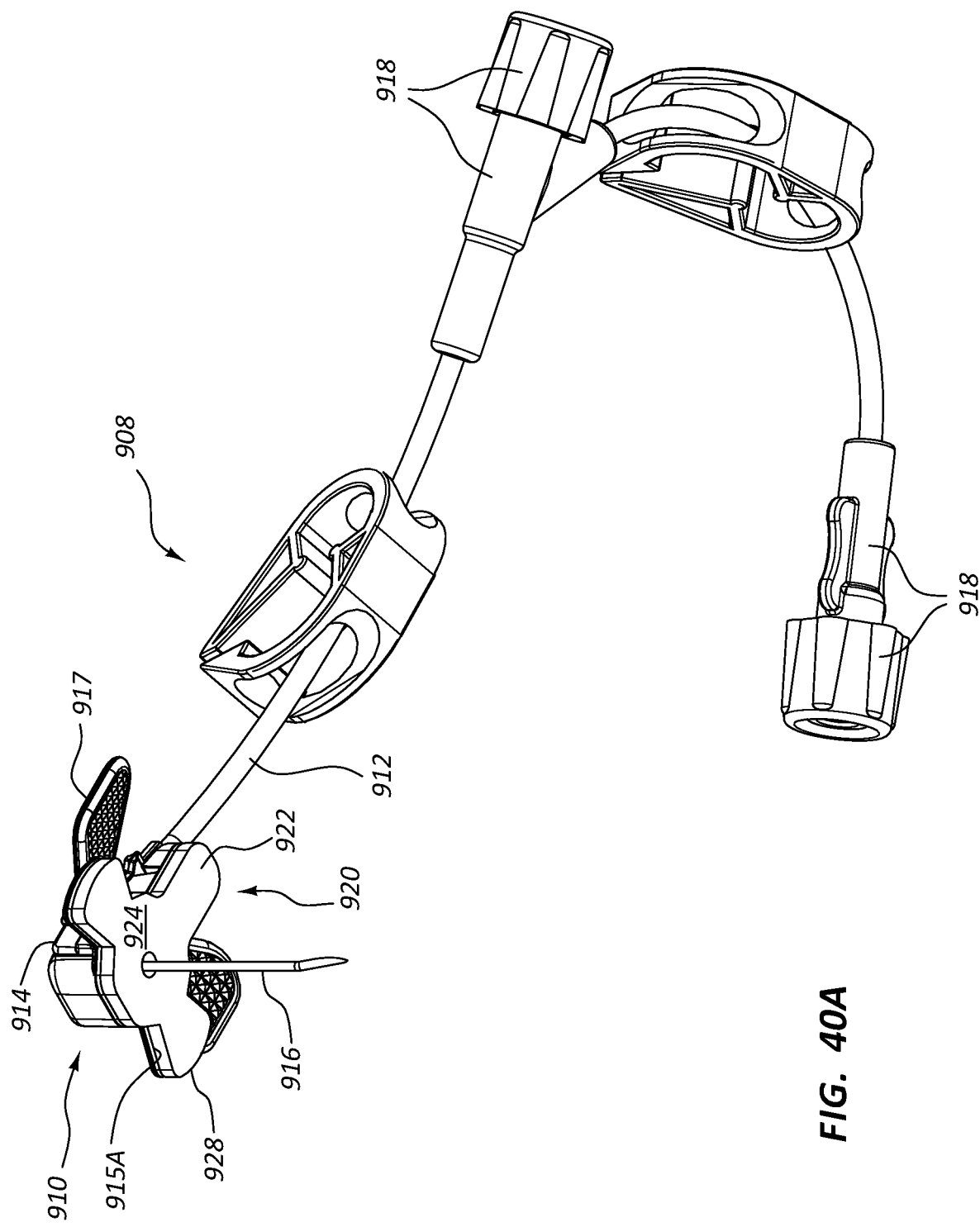
FIGS. 40A-40E are various views of an infusion set including an interface pad according to one embodiment.
Figure 40B:
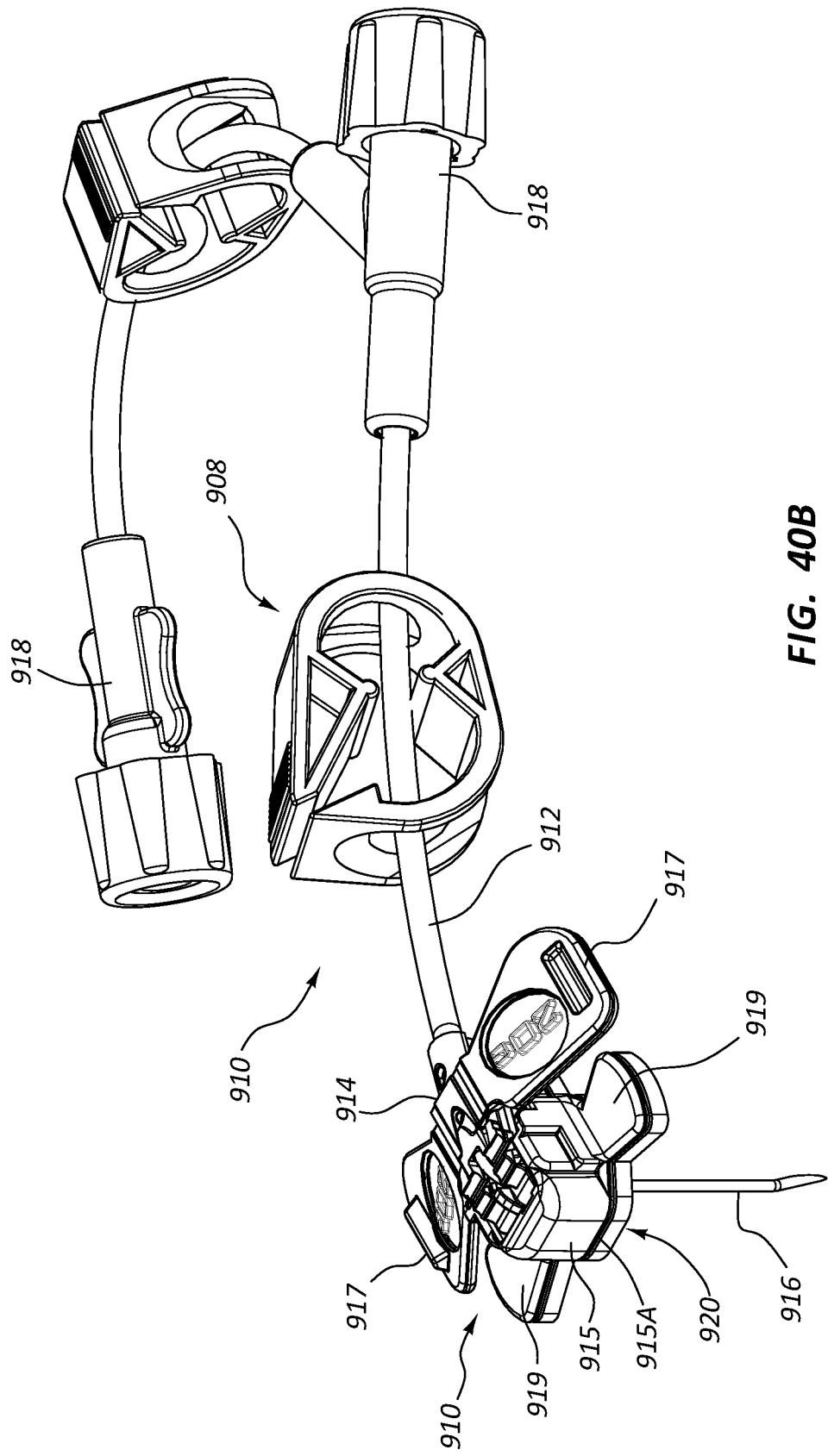
Figure 40C:
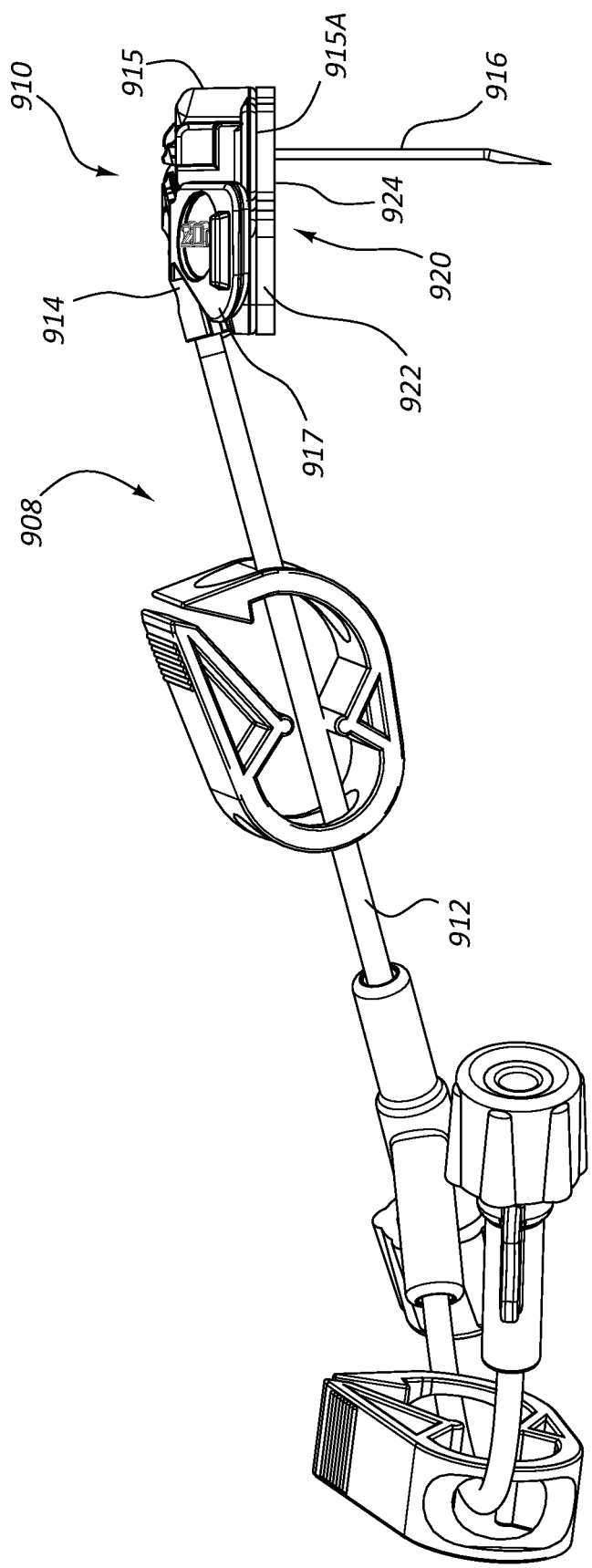
Figure 40D:
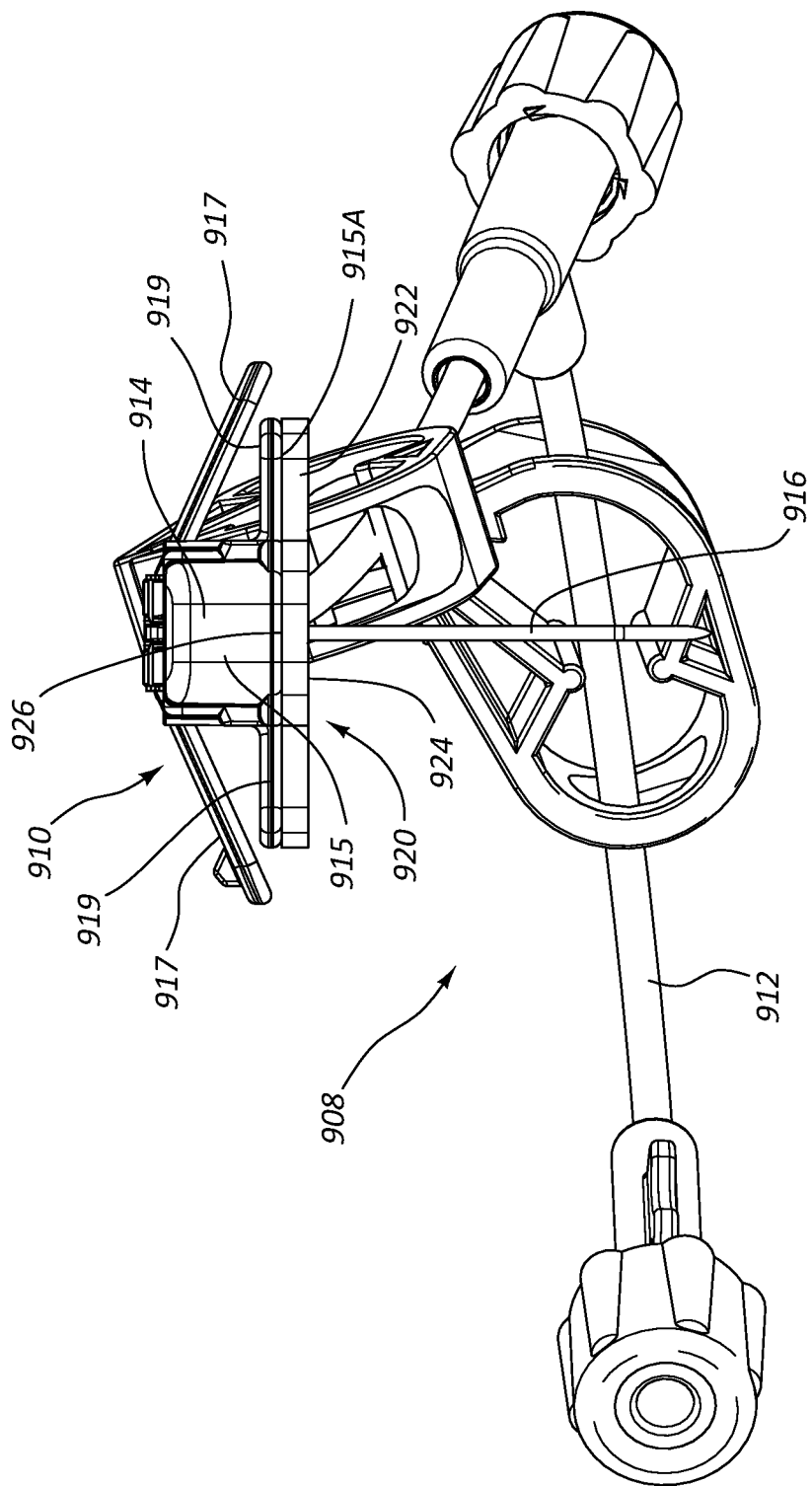
Figure 40E:
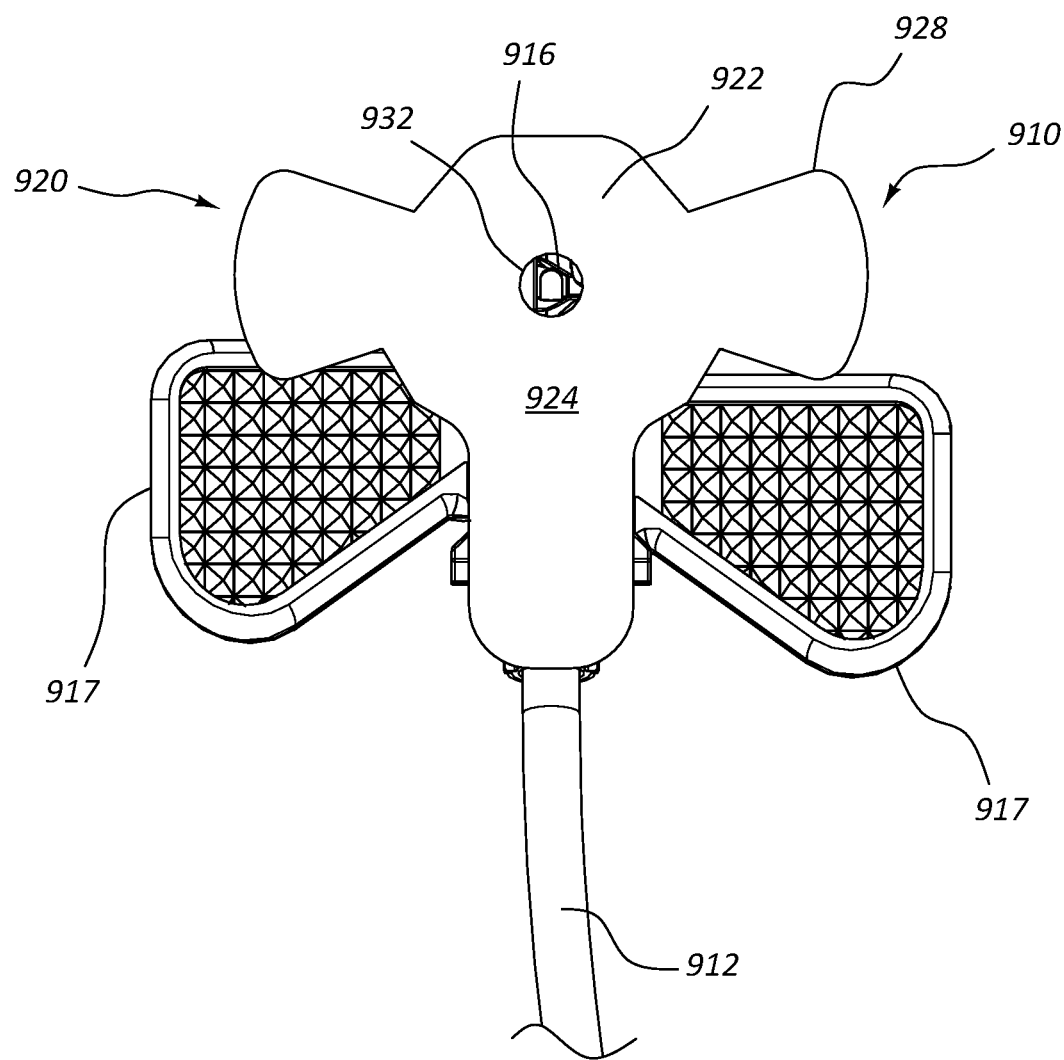

In another embodiment, it is appreciated that the hole of the interface pad, such as the hole 932 shown in FIG. 40E, can be sized larger than what is required for passage of the needle 916. Note that the shape of the interface pad can be formed a number of ways, including die-cut. Thus, it is appreciated that the interface pad can include one of a variety of shapes, sizes, and configurations, and can be employed on a variety of percutaneous medical devices. In one embodiment, for example, the size of the interface pad is selected so as to not obscure the view of the clinician placing the medical device into the patient.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method of manufacturing an insertion assembly, comprising:
    forming a catheter assembly including a catheter hub and a catheter;
    inserting a needle into the catheter assembly such that a distal tip of the needle extends distal of a distal end of the catheter; and
    permanently adhering an interface pad to the catheter hub, the interface pad including:
        a foam material including a haemostatic agent; and
        a proximal end having an outer diameter substantially similar to a distal end of the catheter hub.

2. The method of manufacturing according to claim 1, wherein permanently adhering comprises wrapping a foam strip about the distal end of the catheter hub.

3. The method of manufacturing according to claim 2, wherein the foam strip includes a plurality of spaced-apart teeth.

4. The method of manufacturing according to claim 1, wherein permanently adhering comprises adhering the interface pad such that the catheter extends through a hole defined in the interface pad.

5. The method of manufacturing according to claim 1, wherein the foam material includes polyurethane, and wherein the haemostatic agent includes negatively charged sulfonate groups that are added to a soft segment of the polyurethane.

6. The method of manufacturing according to claim 1, wherein the foam material further includes an antimicrobial agent comprising chlorhexidine gluconate.

7. The method of manufacturing according to claim 1, wherein permanently adhering comprises penetrating the interface pad with the distal tip of the needle and sliding the interface pad over the catheter to the distal end of the catheter hub.

8. The method of manufacturing according to claim 1, further comprising including with the insertion assembly an infusion set for accessing an implanted access port.

9. The method of manufacturing according to claim 1, wherein the haemostatic agent includes a hydrocolloid.

10. The method of manufacturing according to claim 1, wherein the haemostatic agent includes microdispersed oxidized cellulose.

11. The method of manufacturing according to claim 1, wherein the interface pad includes a compliant material to provide patient comfort when the catheter assembly is disposed on a patient's skin.

12. The method of manufacturing according to claim 1, wherein the foam material includes an aromatic polyether polyurethane.

13. The method of manufacturing according to claim 1, wherein the foam material is absorptive.

14. The method of manufacturing according to claim 1, wherein the foam material includes a compressed foam that expands when contacted by blood.

15. The method of manufacturing according to claim 1, wherein the interface pad includes about 11 percent by weight of chlorhexidine gluconate and about 8 percent by weight of microdispersed oxidized cellulose.

16. The method of manufacturing according to claim 1, wherein the interface pad includes a silicone adhesive including an antimicrobial agent.

17. The method of manufacturing according to claim 1, wherein a first side of the interface pad is angled toward the needle such that a distal end of the interface pad has a diameter less than the distal end of the catheter hub.

* * * * *